United States Patent
Maliga et al.

(10) Patent No.: US 10,563,212 B2
(45) Date of Patent: Feb. 18, 2020

(54) INTERCELLULAR TRANSFER OF ORGANELLES IN PLANT SPECIES FOR CONFERRING CYTOPLASMIC MALE STERILITY

(71) Applicant: Rutgers, The State University of New Jersey, New Brunswick, NJ (US)

(72) Inventors: Pal Maliga, East Brunswick, NJ (US); Zora S. Maliga, East Brunswick, NJ (US); Csanad Gurdon, El Cerrito, CA (US); Gregory N. Thyssen, New Orleans, LA (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 479 days.

(21) Appl. No.: 15/043,184

(22) Filed: Feb. 12, 2016

(65) Prior Publication Data
US 2016/0272981 A1   Sep. 22, 2016

Related U.S. Application Data

(63) Continuation-in-part of application No. PCT/US2015/011033, filed on Jan. 12, 2015, and a continuation-in-part of application No. 13/930,378, filed on Jun. 28, 2013, now abandoned, which is a continuation-in-part of application No. PCT/US2011/068153, filed on Dec. 30, 2011.

(60) Provisional application No. 61/926,315, filed on Jan. 11, 2014, provisional application No. 62/021,599, filed on Jul. 7, 2014, provisional application No. 61/428,672, filed on Dec. 30, 2010.

(51) Int. Cl.
*C12N 15/82* (2006.01)
*A01G 2/30* (2018.01)

(52) U.S. Cl.
CPC .......... *C12N 15/8214* (2013.01); *A01G 2/30* (2018.02); *C12N 15/8289* (2013.01)

(58) Field of Classification Search
None
See application file for complete search history.

(56) References Cited

PUBLICATIONS

Melnyk et al. 2015, Current Biology vol. 25, Issue 5, Mar. 2, 2015, p. R183-R188. (Year: 2015).*
Zelcer, et al. Zeitschrift fü Pflanzenphysiologie 90.5 (1978): 397-407. (Year: 1978).*
Aviv, et al. Theor. AppL Genet. 58, 121-127 (1980). (Year: 1980).*
Gurdon, et al. Proceedings of the National Academy of Sciences 113.12 (2016): 3395-3400. (Year: 2016).*
Stegemann et al. (Science 324.5927 (2009): 649-651). (Year: 2009).*

* cited by examiner

*Primary Examiner* — Charles Logsdon
(74) *Attorney, Agent, or Firm* — Kathleen D. Rigaut; Howson & Howson LLP

(57) ABSTRACT

Compositions and methods for effecting the transfer of the CMS trait in plants are disclosed.

5 Claims, 23 Drawing Sheets
Specification includes a Sequence Listing.

Graft transfer of mitochondria

Fertile GT-19-1C flower

CMS GT-19-1C flower

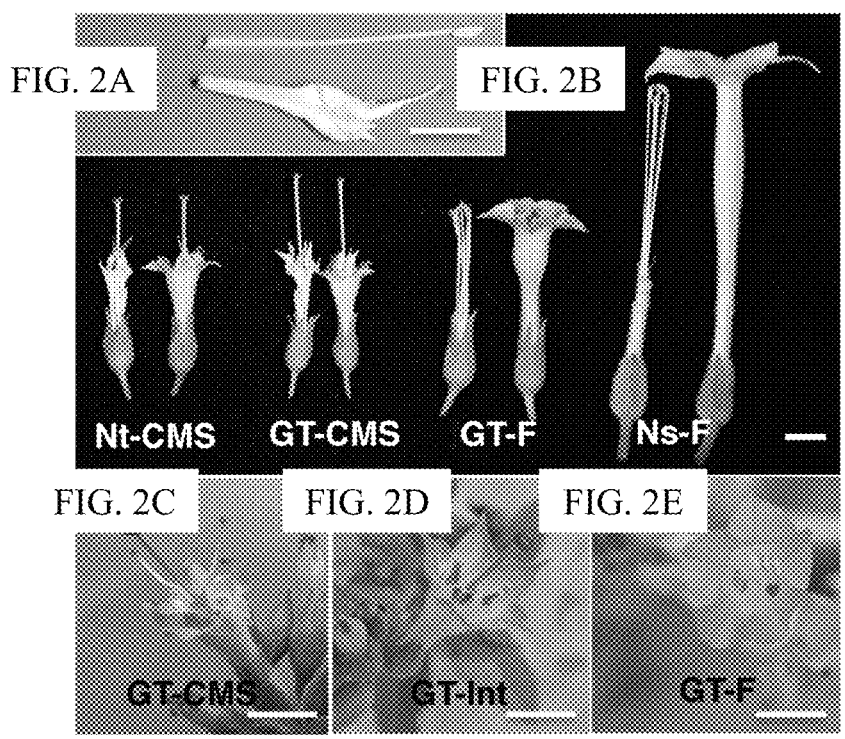

FIG. 3A
FIG. 3B
FIG. 3C
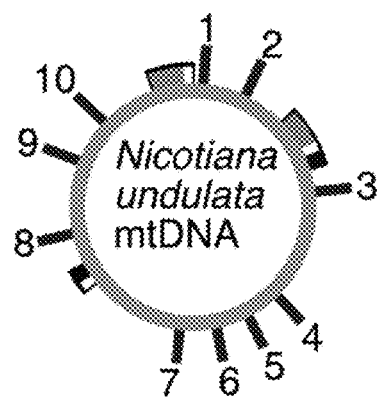
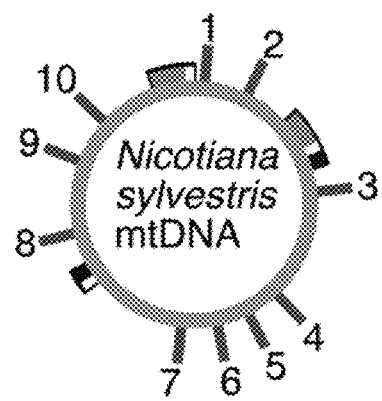
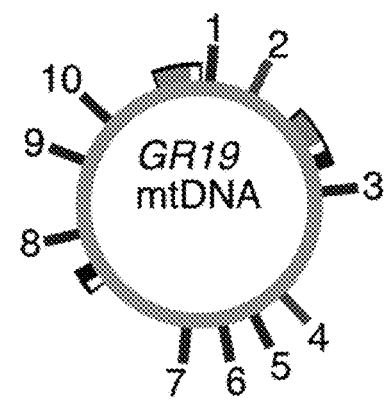
FIG. 3D
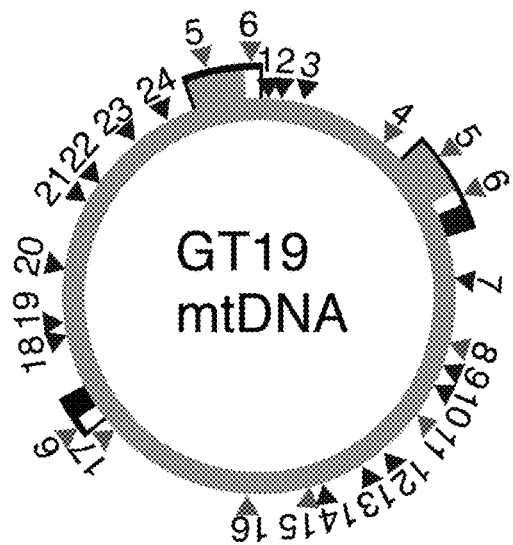

FIG. 4D

```
              3,573                  5,501
     und AGAAGCAAGGA --- TTAACTTCCCC
     syl AGAAGGAAGGA --- TTAACCTCCCC
     RF1 AGAAGCAAGGA --- TTAACCTCCCC
     RF2 AGAAGCAAGGA --- TTAACCTCCCC
     RS2 AGAAGCAAGGA --- TTAACCTCCCC 113,931                114,285
     und AATTCGACTCT --- AAAGTATTACC
     syl AATTCTACTCT --- AAAGTCTTACC
     RF1 AATTCGACTCT --- AAAGTCTTACC
     RF2 AATTCGACTCT --- AAAGTCTTACC
     RS3 AATTCGACTCT --- AAAGTCTTACC
     RS4 AATTCGACTCT --- AAAGTCTTACC 124,966                125,774
     und CGCTTCGCCTG --- GGCCTTCTCGT
     syl CGCTTTGCCTG --- GGCCTCCTCGT
     RF1 CGCTTCGCCTG --- GGCCTCCTCGT
     RF2 CGCTTCGCCTG --- GGCCTCCTCGT
     RS3 CGCTTCGCCTG --- GGCCTCCTCGT
     RS4 CGCTTCGCCTG --- GGCCTCCTCGT 135,505                135,740
     und TATAGTGGTTC --- CCGTCTAGGTT
     syl TATAGCGGTTC --- CCGTCGAGGTT
     RF1 TATAGCGGTTC --- CCGTCTAGGTT
     RF2 TATAGCGGTTC --- CCGTCTAGGTT
     RS3 TATAGCGGTTC --- CCGTCTAGGTT
     RS4 TATAGCGGTTC --- CCGTCTAGGTT 395,427                395,845
     und CCTGTAAACTC --- ACAAACAGGCA
     syl CCTGTGAACTC --- ACAAAGAGGCA
     RF1 CCTGTAAACTC --- ACAAAGAGGCA
     RF2 CCTGTAAACTC --- ACAAAGAGGCA
     RS3 CCTGTAAACTC --- ACAAAGAGGCA
     RS4 CCTGTAAACTC --- ACAAAGAGGCA
```

FIG. 6A 6,013 nt CMS region in *N.undulata* mtDNA: fragment ends are homologous to 262,816 nt and 393,200 nt in the *N. tabacum* mtDNA (NC_006581).

```
TTAAATAAAAGCTAAAGCACTTTCTTTTAAGAATGTATCTGGTTCCATCTTTCTTTCGTTAGTTAAGCCACCTTTTTCTAAAAAGGATTGTAGTAATTCTG
GTTTGACACTATTTGGAATGGCTCTCTCATATTGAGAAATTCTGTCTAGTGGCATTCGATCACAGAATCCATTGACAGCTGCATAAATGACTAGAATTT
GTTTTTCAATTGGCAGTGGTGCATATTGTGGTTGTTCGGTACTTCTGTCAGCCTTGCACCTCTATTGAGTAATGCCTGAGTCGCAGCATCAAGGTCTGA
GCCAAATTGAGCAAGGGCGGCCACTTCGCGATATTGTGCCAATTCCAGTTTTGAACTACCGCAGACTTGTTTCATAGTTTTCAACTGAGCGGCAGACCC
GACGCGACTGACAGATAAGCCGACGTTAATCGCAGGTCTAATTCCGCGATAAAAGAGCTCTGTTTCCAAACAGATTTGTCCATCAGTAATGGGGATCA
CATTGGTGGGAATATAGGCCGATACGTCTCCAGCTTGTGTTTCAATGACGGGTAAGGCGGTCAAGCTACCTGCGCCTGTCTGGTCCGATCGTTTAGCCG
CTCTTTCTAAGAGACGGGAATGTAAATAGAAAACATCCCCTGGGAAAGCCTCACGACCTGGTGGTCGGCGTAACAATAATGACATTTGTCGATATGCT
ACCGCCTGTTTACTAAGATCATCATAGATTATTAATGCGTGCATTCCATTATCGCGGAAATATTCCCCCATGGCACACCCAGAATATGGGGCCAAAAAT
TGTAGAGGAGCAGGATCCGAAGCGGTGGCTGCTACAAGAATAGAATATTCCAAAGCATTCGCTTCTGAAAGAATTTGAACTAATTGTGCCACAGTTGA
GCGTTTCTGTCCAATCGCTACATAGACACAATACAATGTCTCACTCTCAGAGGTGGCCCTTGAGTTCAGTTGCTTTTGGTTTAATATGGTATCGATAGCA
ATAGCAGTTTTTCCAGTTTGTCGGTCCCCGATTATAAGTTCTCGTTGACCACGACCTATAGGAACCAGGCTATCTACCGCTTTTAACCCTGTTTGCATAG
GCTCGTGCACAGATTTACGTTCAATAATACCAGGGGCTTTCACTTCGACACGTCTTCGCTCGTGATCGCTTAGAGCCCCCCTTCCATCAATAGGTACTCC
CAAGCCATCGACCACACGCCCTAGCATAGCCTTTCCCGCAGGAACATCCACAATAGATCCAGTGCGCTTGACAAGATCTCCTTCTTTAATAGCAGTATC
ACTACCAAAGACAACAATCCCTACATTCTCATTCTCAAGATTCAAGGCTATTCCTTTCACACCGCTGGCAAATTCAACCATTTCCCCAGCTTGAATCTCG
TTCAATCCATAAACACGTGCAATTCCATCTCCAACTGAGACCACTCGACCGATCTCATCCACTTGAAAATTGGTGTAAAAGTTGCTAATTCGACTTTCTA
ATAGACTTGTTAGTTCCGCAGCTCGGGGAGAAAGTTCCATAATTCAATTAAAGATAGATAGAAGGGAGAATGCCGCTTTAGAAAAAAAGAAAAATCAT
AAGGAAACATTCTCTATATACTCACCTTAAATTACCCCCCAAATATAATATTGATATAAAGTGAGTTCGGCCCATCTCTCGTCAGATCGTGTGAAAGTA
GACCCAAAAAGCGGAGCTCTTTTCCTGTCTCTTACGAAGACAGCCCCGCCTTGTAGGTCAAGTTCACTTCGTTTCTCATTCAAAAAGTCGCAAAAGGCTT
CTTGTGGGTTGGAATCGGCATTTTCGGCCACGGCAGGGTGCGCAGTCAGTATTTCTTGATAAATCGAATAGCATGAATGCCTTTTCTCACGGATCTGAA
GATCCCTATTCTCGAACTCGAGCAATCGGTTGTATTCCCTTTGCGAGGGACAATTGTCGAGTTGAGTCTTTACTTCCGCCCAATTCGACCCCCTCTCTTC
AGAGAGAAGAAAAGGGCTCTTTTCCTGTTCCAGTGCCAATAGCCTATTTCTCATCGATGCCTCCAAGGCTACATTGTGAGTCACGGGCCAAGGCTCCGA
CAGGACCTGGAGCTCGAATGAATCCTCCGAGGAGGAGTTTGATGGGGTGGAAGGGCCCGGAAGAGGAAGTGGCTGCCCCCCCCCGAAACAACACTG
AAAACAGCAAAAAAGAAAAAAGATCTAGAAAATAAACACACAAGTTAGATAGAAAATAGGTGCGTAAACAACACCCAAATAAGGAGATGGAAAAA
AGAATAGATATATATGATATAGAGAAGTCGAAAGCCAGATTTTTGATTCAAACGAAAACGATTTCTACGAACGATAAAGGTCAGGGAAAAAGAA
GGATTCCAAAAAGTACGAGATTTCCACCCGTGGTCATTATAGCGGTTCCTTCTTTTCCTAGAAAATGATAAAAAAAAAAGGCGGTAACAAAGGGCACA
AAATAACGAATGAGACCCATGGCAAACATAAAATTGGGGTACCTCGGTACGACCTGCGCGGTTGTTCCTATTTCATTTTCTTCTTCCAAGTTCTTTCGCG
CACTGAGTTACTTACGGAATCTCAGACCCCCCTCGGCAGGACCACAGGCCCGTGTAAACACCTCAACGAACTCATGTGGACACTCCTCAGCACCGAGG
ACAATCTCTCAAATACACATGTTGATGTTGTTGACCCGTTTTTCTTTTCTTTGCTACGATTACGCTACGATCTTTCTTCTCTTATGATATTTTTTGATAAGT
CGAGCCTTCGCTCTTGCCTATAATAAGAGGTCAAGGATCGAGTCGTCTGTTCATAGTTTCACTTCGCTTCTGCCATTCTGTTCCCCTCGGACTATTAAGG
GAAAGCAAGGCAAGGAACCCTTGGTATGCACGAGACAAGCATAAGACACCAACCAAAAGTACTCTTTCGGAATCAGGTGAGTCAAAGGTCAGGAGCT
CAATCAAAACTAGCTACACTTCCCTCTCAGCCTGCCTGCAATCCGGTGAAACTGTTAGACGAAGAGGACTCGTCTTTCATGCGGAAAGCGACCCACGG
AAGTCTTCTCACTTGGAATAGAGCTCACCAGAAAAAAGACAGGTTCAAGTACGAAGGCTATTCCGTGAGTTTAGACGGAAGCAAATAACTGATAGTTG
TCTGTGCCCAAGGTCAGATTATCGACATCGGTATTGGGGTAGCAAGAAGATGCATTGGCTGATAACATATCCATCGCCCTTCCTCGGTCCGTCCCCATA
GCAAGCTTCCTATTGGCTTCTCACCCCGGACTGAGACTCGCTCTTCTCGTCCAGAAGAATAGTTGTCTTCCTGGTTAACTAGTCATTGGTCTTTGGCACC
AAAGAAAGTCGAGAAGGTTGGGACGCAAGGTGGTTGTCGCTCAAGCAACTGTGGAAGCAGACTCCGTGAAAAAGTCGTGTGCATCAAAGAAAGGGAA
GGGCTCTCCCTCTCTATCTTGAACCTAGCTCTGCCCAGCTTGGATGAACAAAGTGTGCAATGCGTGGAGTGAGATCACTACCATACCTTTTTCCATTTTT
CTAGTGAACATAGGCTTCGAGTGCGTACCAGGCGAGACTATGACTGAGTCAAGCGGACACCCGCTAATCCGCGCTTCCATTCGCGACCTGAAGCCAAG
CCATTGACGAGCCTCGAAGGACCTTTCAAGCCTCCCCGCTTCGATTCGTTTGCTTTCCCTTTCTCACTCTGAAAGAAAGAAGAAAGCCTTGCTTTGCCTC
CTTCCTTCTTCGCTAATTGAAAGCTAGACTCACACGTCTGCTTATGAAGATTAGTGGCTTCCTCACTTGTTTGATTTGAAATGGCACGATGCTTAACACAT
GTAATTGGAGTCTGTTTCGGGGCTTACAGAAGCTCGTGCAAAGAAGATTTATAGGAGAGAAGTTCCCCATCTCTCTTAGGCCTTCTGTCTCTTGAAAAA
TATTGTATTCTTATGTTTGAGATCGCCTCTGTGTGATTCATCCTAAGTAGCTAACCGAAAAGGAACTGACTGAAAGGACTGATAAGAGAAGAGGCTCTA
ACTGTTTAAAGGTAAAGGAAAGGAAGCCAGGTGAAATCACCCTTGATAAAGGAAGGCTCCTACAAAGAGTCGACCAGGCCTTGTAGAAGCGAAGAT
CGATGTCCGTCCCATTCGGCGAAGCAATCTTGGACCCTCTTGGCTGCGCTGTGCTTGGATGCACTAGTCTTCCACACGCCAGCGATGAGATGAAAACTG
CCCCCATTCAGTGGTTCCCGTGCCACCAAAATGGCATAGCATCGAAAGAGTGACCGGAACCTGTCCCTGACCAGCTCGTAAGTAGCATCCCGCTGCTG
GTCGGCACAGCGGGGCGTCAAAAGCAAGTCTTTTTTGATTGCCCCGCTGACCTTTTCTAAAAGCACCTTGGGTCGGAGGCTGGTTGTAAAGTAAAGAA
GGGTGGTGCGCTTTCGAATTCGATTAATTTTGATAGAAAGAAGAACCAGAATTGGTCCTGGGTCGTATCGTTTTTCAACTGTCCGCTGGTAAATCTGGT
CTAGCACTACAATGTCTCCATTGTGCGGCGCTATGAAAGAGAAAAGAAATTCTGCCTCGCTAGCCTTTTCACCTCTTCTCTTCCGTCGGTCTTGTACTGA
GCCATCAGAATAGGGATGGTGCCAAGAAAGGCAGTTTAATCTATATCTGTAGAACGAACAAAGCAAAGATATTCAAATAAAGAATTTGTGAGGGAAT
GACTATTCATCTATTGTATTTTCATCCAGGCAAGAAAAAGATCGTGTATATGTCGCAGCCTTCTTCTTCTTAAAGAAAATGAACGAAG
GCCCAAGGGCTTTTATCCATCAGACATGAATGAAAGGGGATGACACCACTCTAATGATTGGAAAAATCCTTAATATCATAAAGGAAAGGTCTTTTCTT
AAAAGCTTCAGTAATAGCAAAAGCAGCCTATCTGGAATGGCCTACTCCTTACTCAAGCAAAGCTGTATGCAACCGCATAGAGGAAGTTAAGCCAATCC
CTCTATTTTCATCTTGAAAGATTCGGAAAAATAGAACATGCTCCACCCCTTCCTTCGATTGCTTTCATTTTTGGCCCGATCAGGCTTCACCTTCTTATCGG
GATAGCCATTTAGCTTGCTTCTTGGGACTAGCCTTGAATACTAGCCATTTTCTCATCGCATCAAGAGGGCTTTCAGAGAGAGGGCTCCAACCCTCTATA
ATCGAGTGATGGTGGAATGACCAATCCAGTTCCCTCAGGCTGGCTTTCTCCAAGGGCAGTTTTGTCCTGTCCGCTAGGACTGGTCTAAATGTGCGGGAT
CGATACATCGGTAGGGAGGCTCGGCCAAGCATCACGGTAGCAGAGCCATAGGGCTCTAAAGAGCTGAGAACAACCGCACTCAGCACACCTCTGAATT
CTTCTTGACACGTGGCAGTCATTGACTTGATGTGGTAACTTTACATTCTTAAAGCTTTAGGCGAACTAAACGATTGACTAGAATAAATTACCTTATTGCG
CTCTTCGCCTTCTTTCTATCTAGCAAACCTAAGAAAGGAAAGGGACAAAAAGTGGGATTAATCCTGATTTCTTTGGTTAGTTCTTGTCATCACACAAAA
CTAGCGTTCGCCTTCTATGAGTAAAATCCATTCTCTAGCGGATTCCCCGGAGATAGTCCGATTAATCCAGATGATAAGGGAATGACTGATGAGACTACC
GACACCTTTTATCGAGTAAGTCATACCGAGCTTGGTGAAAGAAAAAAATGGTACTAGCTAAAGAGAAGGATCAGACAAATTTCTTTAAACTCTCATA
CAAAGGGGAAAAAGCTACGGTTGAAAGATCACTGGGTTTAGGAGGAGGCTAGGTTAGCCGAAAGATGGTTATCGGTTCAAGAACGTAAGGTGTCCC
CCCCTTATATAATATAAGGAAGTCACTTTTTCTACGATGTTCGAGATCTTTGTCTCGCAGAGGGTGAAATGGCGATCTGTTA
```

FIG. 6B
1,567 nt *N. sylvestris* mtDNA region homologous to nucleotides 262,816 to 261,250 (complement strand) in the *N. tabacum* mtDNA (NC_006581). This is the fertile homolog of 1-1,567 nt of the CMS region in *N. undulata* mtDNA.

```
TTAAATAAAAGCTAAAGCACTTTCTTTTAAGAATGTATCTGGTTCCATCTTTCTTTCGTTAGTTAAGCCACCTTTTTCTAAAAAGGATTGTAGTAATTCTG
GTTTGACACTATTTGGAATGGCTCTCTCATATTGAGAAATTCTGTCTAGTGGCATTCGATCACAGAATCCATTGACAGCTGCATAAATGACTAGAATTT
GTTTTTCAATTGGCAGTGGTGCATATTGTGGTTGTTTCGGTACTTCTGTCAGCCTTGCACCTCTATTGAGTAATGCCTGAGTCGCAGCATCAAGGTCTGA
GCCAAATTGAGCAAGGGCGGCCACTTCGCGATATTGTGCCAATTCCAGTTTTGAACTACCGCAGACTTGTTTCATAGTTTTCAACTGAGCGGCAGACCC
GACGCGACTGACAGATAAGCCGACGTTAATCGCAGGTCTAATTCCGCGATAAAAGAGCTCTGTTTCCAAACAGATTTGTCCATCAGTAATGGGGATCA
CATTGGTGGGAATATAGGCCGATACGTCTCCAGCCTGTGTTTCAATGACGGGTAAGGCGGTCAAGCTACCTGCGCCTGTCTGGTCCGATCGTTAGCCG
CTCTTTCTAAGAGACGGGAATGTAAATAGAAAACATCCCCTGGGAAAGCCTCACGACCTGGTGGTCGGCGTAACAATAATGACATTTGTCGATATGCT
ACCGCCTGTTTACTAAGATCATCATAGATTATTAATGCGTGCATTCCATTATCGCGGAAATATTCCCCCATGGCACACCCAGAATATGGGGCCAAAAAT
TGTAGAGGAGCAGGATCCGAAGCGGTGGCTGCTACAAGAATAGAATATTCCAAAGCATTCGCTTCTGAAAGAATTTGAACTAATTGTGCCACAGTTGA
GCGTTTCTGTCCAATCGCTACATAGACACAATACAATGTCTCACTCTCAGAGGTGGGCCCTTGAGTTCAGTTGCTTTTGGTTTAATATGGTATCGATAGCA
ATAGCAGTTTTTCCAGTTTGTCGGTCCCCGATTATAAGTTCTCGTTGACCACGACCTATAGGAACCAGGCTATCTACCGCTTTTAACCCTGTTTGCATAG
GCTCGTGCACAGATTTACGTTCAATAATACCAGGGGCTTTCACTTCGACACGTCTTCGCTCGTGATCGCTTAGAGCCCCCTTCCATCAATAGGTACTCC
CAAGCCATCGACCACACGCCCTAGCATAGCCTTTCCCGCAGGAACATCCACAATAGATCCAGTGCGCTTGACAAGATCTCCTTCTTTAATAGCAGTATC
ACTACCAAAGACAACAATCCCTACATTCTCATTCTCAAGATTCAAGGCTATTCCTTTCACACCGCTGGCAAATTCAACCATTTCCCCAGCTTGAATCTCG
TTCAATCCATAAACACGTGCAATCCCATCTCCAACTGAGACCACTCGACCGATCTCATCCACTTGAAAATTGGTGTAAAAGTTGCTAATTCGACTTTCT
AATAGACTTGTTAGTTCCGCAGCTCGGGGAGAAAGTTCCATAATTCAATTCAAGATAGATAGAAGGGAGAATGCCGCT
```

FIG. 6C
3,515 nt *N. sylvestris* mtDNA region homologous to nucleotides 389,686 to 393,200 in the *N. tabacum* mtDNA (NC_006581). This is the fertile homolog of 2,743-6,013 nt of the CMS region in *N. undulata* mtDNA.

```
TTTCTTCTCTTATGATATTTATTGAAAATTCGAGCCTTCGCTCTTGCCTATAATTATAATAAGAGGTCAAGGATCGAGTCGTCTGTTCTTTCACTTCGCTT
CTGCCATTCTGTGCTTTCCCCTCGTACTATTAAGGGAAAGCAAGGCAAGGAAACCTTGGTATGCACGAGAAAGCATATGACACCAACCAAAAGTACG
CTTTCGGAATCAGGTGAGTCAAAGGTCAGGAGCTCAATCAAAACTAGCTACACTTCCCTCTCAGCCTGCCTGCAATCCGGTGAAACTGTTAGACGAAG
AGGACTTGTCTTTCATGCGGAAAGCGACCCACGGAAGTCTTCTCACTTGGAATAGAGCTCACCAGAAAAAAGAGGGTTCAAGTACGAAGGCTATTCC
GTGAGTTTAGACGGAAGCAAATAACTGATAGTTGTCTGTGCCCAAGGTCAGATTTATCGACATCTGTATTGGGGTAGCAAGAAGATGCATTGGCTGATA
ACATATCCATCGCCCTTCCTTGGTCCGTCCCCATAGCAAGCTTCCTATTGGCTTCTCACCCCGGACGGAGACTCGCTCTTCTCGTCCAGAAGAATAGTTG
TCTTCCTGGTTAACTAGTCATTGGTCTTTGGCACCAAAGAAAGTCGAGAAGGTTGGGACGCAAGGTGGTTGTCGCTCAAGCAACTGTGGAAGCAGACT
CCGTGAAAAAGTCGTGTGCATCAAAGAAAAGAAAGCTCTCCCTCTCATCTTGAACCTAGCTCTGCCCAGTTGGATGAACAAAGTGCGCA
ATGCGTGGAGTGAGATCACTACCATACCTTTTTCAATTTTTCTAGTGAACATAGGCTTCGAGTGCGTACCAGGCGAGACTATGACTGAGTCAAGCGGAC
ACCCGCTAATCCGCGCTTCCATTCGCAACCTGAAGCCAAGCCATTGACGAGCCCCGAAGGACCTTTCAAGCCTCCCCGCTTCGATTCGTTTGCTTTCCCT
TTCTCACTCTCGAAAGAAAGAAGAAAAGCCTTGCTTCGCCTCCTTCCCTTCTTCGCTAATTGAAAGCTAGACTCACACGTCTGCTTATGAAGATTATGGCTTC
CTCACTTGACCTTCTTTCTAGCCTTTTATTTTTATTTGAAATGGCACGATGCTTAACACATGTAATTGGAGTCTGTTTCGGGGCTTACAGAAGCTCGTGC
AAAGAAGATTTATAGGAGAGAAGTTCCCCATCTCTCTTAGGCCTTCTGTCTCTTGAAAAATATTGTATTCTTTGAGATCGCCTCTGTGTGATTCATCCTA
AGTAGCTAACCGAAAAGGAACTGACTGAAAGGACTGATAAGAGAAGAGGCTCTAACTGTTTAAAGGTAAAGGAAAGGAAGCCAGGTGAAATCACCCC
TTGATAAAGGAAGACTCCTACAAAGAGTCGACCAGGCCTTGTAGAAGCGAAGATCGATGTCCGTCCCATTCGACGAAGCAATCTTGGACCCTCTTGGT
TGCGCTGTGCTTGGATGCACTAGTCTTCCACACGCCAGCGATGAGATGAAAACTGCCCCCATTCAGTGGTTCCCGTGCCACCACAATGGCATGGCATCT
AAAGAGTGACCGGAACCTGTCCCTGACCAGCTCGTAAGTAGCATCCCGCTGCTGGTCGGCACAGCGGGGCGTCAAAAGCAAGTCTTTTTTGATTGCCC
CGCGGACCTTTTCTAAAAGCACCTTGGGTCGGAGGCTGGTTGTAAAGTAAAGAAGGGTGGTGCGCTTTCGAATTCGATTTCTTTTGATAGAAAGAAGA
ACCCCGTCCCACGAGCGGAGGGAGGTCCTGGGTCGTATCGTTTTTCAACTGTCCGCTGGTAAATCTGGTCTAGCACTACAATGTCTCGATTGTGCGGCG
CTATGAAAGAGAAAAGAATTCTGCCTCGCTAGCCTTTCACCTCTTCTCTTCCGTCGGTCTTGTACTGAGCCATCAGAATAGGGATGGTGCCAAGAAA
GGAAGTTTAATCTATATCTGTAGAACGAACAAAGCAAAAATATTCAAATAAAGAATTTGTGAGGGAATGACTATTCATCTATTGTATTTTCATCCAGGC
AAGAAAAAGTCTATGGAAAGATGCTGTATATGTCGCAGCCTTCTTAAACAAAATGAACGAAGGCCCAAGGGCTATAATTGGTGTACTATCCAAAGACA
GAATAGAAAAATACAAATAAGAGAGGCTTTCCCAGAGCCTTCTTTTCTATGGGGTGGGAATCCAATAGGGATTCGATTCCTCCTCTCCCGAGTGCCTGA
ACGCGCTATTTAACCTCTCAGGTAGGTCAAATGGCATTCCGCTTACTGACCTAATCGACTGTTAGGCCTACGGGCTTTTATCCATCAGACATGAATGAA
AGGGGATGACACCACTCTAATGATTGGAAAAATCCTTAATATCATAAAGCAACATATCATAAAGGAAAGGTCTTTTTCTTAAAAGCTTCAGTAATAGC
AAAAGCAGCCTATCTGGAATGGCCTACTCGTTACTCAAGCAAAGCTGTATGCAACCGCATAGAGGAAGTTAAGCCAATCCCTCTATTTTCATCTTTTAA
GATTCGGAAAAATAGAACATGCTCTACCCCCTTCCTTCGATTGCTTTCATTTTTGGCCCGATCAGGCTTCATCTTCTTATCGGGATAGCCATTTAGCTTGG
TTTCTTGGGACTAGCCTTGAATACTAGCCATTTTATCATCGCATCAAGAGGGCTTTCAGAGAGAGGGCTCCAACCCTCTATAATCGAGTGATGGTGGAA
TGACCAATCCAGTTCCCTCAGGCTGGCTTTCTTCAAGGGAAGTTTTGTCCTGTCCGTCTAAATGTGCGGGATCGATACATCGGTAGGGA
GGCTCGGCCAAGCATCACGGTAGCAGAGCCATAGGGCGCTAAAGAGCTGAGAACAACCGCACTCAGCACACCTCTGAATTCTTCTTGACACGTGGCAG
TCATTGACTTGATGTGGTAACTTTACATTCTTTAAGCTTTAGGCGAACTAAACGATTGACTAGAATCAATTACCTTATTGCGCTCTTCGCCTTCTTTCTAT
CTAGCAAACCTAAGAAAGGAAAAGGGACAAAAAGTGGGATTAATCCTGATTTCTTTGGTTAGTTCTTGTCATCACATAAAACTAGCGTTCTATGAGTAA
AATCCATTCTCTAGCGGATTCCCATATGCTGAGATAGTCCGATTAATCCAGATGATAAGGGAATGACTGATGAGACTACCGATACCTTTTATCGAGTAA
GTCATACCGAGCTTGGTGAAAGATAAAAAATGGTACTAGCTAAAGAGAAGGATCAGAGAAATTTCTTTAAACTCTCATACAAAGGGGAAAAAAGCTA
CGGTTGAAAGATCACTGGGTTTAGGAGGAGGCTAGGTTAGCCGAAAGATGGTTATCGGTTCAAGAACGTAAGGTGTCCCCCCCTTATATAAGGAAGTA
ACTTTTTCTACGATGTTAGAGATCTTTGTCTCGCAGAGGGTGAAATGGCGATCTGTTA
```

```
CLUSTAL 2.1 multiple sequence alignment und_orf102      MTATCQEEFRGVLSAVVLSSLEPYGSATVMLGRASLPMYRSRTFRPVLADRTKLPLEKAS 60
sylv_orf102     MTATCQEEFRGVLSAVVLSSLAPYGSATVMLGRASLPMYRSRTFRPVLADRTKLPLKKAS 60
                *******************:******************************:* und_orf102      LRELDWSFHHHSIIEGWSPLSESPLDAMRKWLVFKASPKKAS 102
sylv_orf102     LRELDWSFHHHSIIEGWSPLSESPLDAMIKWLVFKASPKKPS 102
                ****************************:**********.*
```

Figure 7

|  | P1 | G1 | P2 |
|---|---|---|---|
| Nucleus | N. tabacum Gent[R] | N. tabacum Gent[R] | N. sylvestris |
| Plastids | N. tabacum | N. undulata aadA+bar[Au] | N. undulata aadA+bar[Au] |
| Mitochondria | N. tabacum Fertile | N. tabacum Fertile | N. undulata CMS |

FIG. 11A

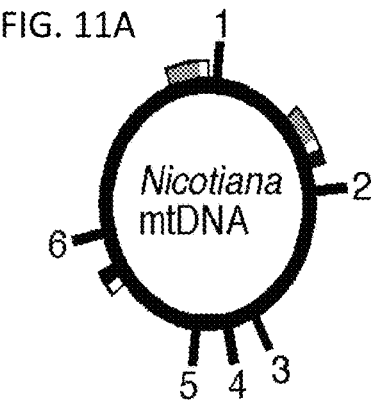

FIG. 11C

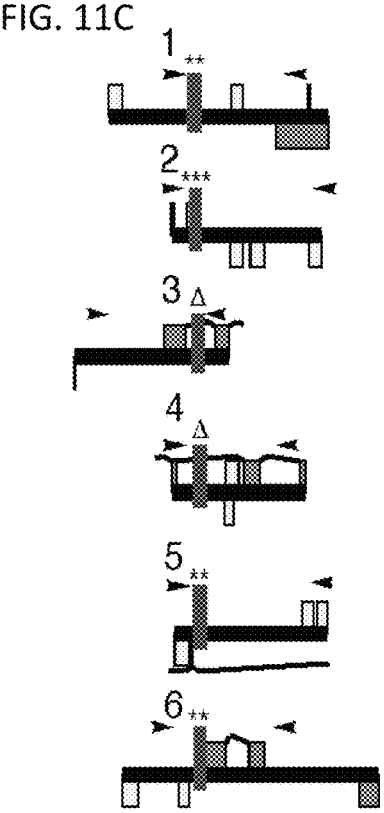

FIG. 11B

| | Gene | Mitochondrial DNA Sequences |
|---|---|---|
| 1 | orf125a | N.t.   aaaaccaat A tcataacttt 1027<br>N.u.   aaaaccaat C tcataacttt<br>G1-4   aaaaccaat A tcataacttt<br><br>N.t.   gaaacgaag T ggagcgaggg 1078<br>N.u.   gaaacgaag C ggagcgaggg<br>G1-4   gaaacgaag T ggagcgaggg |
| 2 | orf129b | N.t.   aaaaaattt A tctcttttta 100418<br>N.u.   aaaaaattt C tctcttttta<br>G1-4   aaaaaattt A tctcttttta<br><br>N.t.   ctttgttct G tagtctttca 100531<br>N.u.   ctttgttct C tagtctttca<br>G1-4   ctttgttct G tagtctttca<br><br>N.t.   ctcccattt G aaagattatt 100821<br>N.u.   ctcccattt T aaagattatt<br>G1-4   ctcccattt G aaagattatt |
| 3 | nad4 intron | N.t.   tgcac CTCCGTACAA gtgct 183637<br>N.u.   tgcac ---------- gtgct<br>G1-4   tgcac CTCCGTACAA gtgct |
| 4 | nad2 intron | N.t.   ttccg GCTGTTTCCG tcatt 202083<br>N.u.   ttccg ---------- tcatt<br>G1-4   ttccg GCTGTTTCCG tcatt |
| 5 | nad5 intron | N.t.   aagaaaaaa GA aaagtcgag 222506<br>N.u.   aagaaaaaa TC aaagtcgag<br>G1-4   aagaaaaaa GA aaagtcgag |
| 6 | orf115-ccmFc spacer | N.t.   ggatcagac T actcctggtg 306939<br>N.u.   ggatcagac C actcctggtg<br>G1-4   ggatcagac T actcctggtg<br><br>N.t.   agcaaaact C gaacggatag 307051<br>N.u.   agcaaaact A gaacggatag<br>G1-4   agcaaaact C gaacggatag |

FIG. 12B

| | Gene | Plastid Sequence Polymorphism |
|---|---|---|
| *1 | atpF intron | N.t. taga G aatcaaaat T gatttacc<br>N.u. taga A aatcaaaat C gatttacc<br>G    taga A aatcaaaat C gatttacc |
| *2 | rpoB-trnC spacer | N.t. t C tgttatggatttcgttg CtA a<br>N.u. t A tgttatggatttcgttg TtC a<br>G    t A tgttatggatttcgttg TtC a |
| *3 | trnL intron | N.t. tca AAATCA aat...aatc T gta<br>N.u. tca ------ aat...aatc C gta<br>G    tca ------ aat...aatc C gta |
| *4 | accD | N.t. caa C gccta C attgcatttgcag<br>N.u. caa T gccta T attgcatttgcag<br>G    caa T gccta T attgcatttgcag |
| *5 | rpl16-rps3 spacer | N.t. tta G aaatgtt T cccttgattga<br>N.u. tta T aaatgtt C cccttgattga<br>G    tta T aaatgtt C cccttgattga |
| *6 | ndhF | N.t. agt A aattcag...ccaac T aag<br>N.u. agt C aattcag...ccaac A aag<br>G    agt C aattcag...ccaac A aag |
| *7 | ndhE-ndhG spacer | N.t. atc T cgactcctttc ----- aat<br>N.u. atc G cgactcctttc CTTTC aat<br>G    atc G cgactcctttc CTTTC aat |

SEQUENCE LISTING

<160> NUMBER OF SEQ ID NOS: 281

<210> SEQ ID NO 1
<211> LENGTH: 6013
<212> TYPE: DNA
<213> ORGANISM: Notonecta undulata

<400> SEQUENCE: 1

```
ttaaataaaa gctaaagcac tttcttttaa gaatgtatct ggttccatct ttctttcgtt      60
agttaagcca ccttttcta aaaggattg tagtaattct ggtttgacac tatttggaat       120
ggctctctca tattgagaaa ttctgtctag tggcattcga tcacagaatc cattgacagc      180
tgcataaatg actagaattt gttttcaat tggcagtggt gcatattgtg gttgtttcgg       240
tacttctgtc agccttgcac ctctattgag taatgcctga gtcgcagcat caaggtctga      300
gccaaattga gcaagggcgg ccacttcgcg atattgtgcc aattccagtt ttgaactacc      360
gcagacttgt ttcatagttt tcaactgagc ggcagacccg acgcgactga cagataagcc      420
gacgttaatc gcaggtctaa ttccgcgata aaagagctct gttccaaac agatttgtcc       480
atcagtaatg gggatcacat tggtgggaat ataggccgat acgtctccag cttgtgtttc      540
aatgacgggt aaggcggtca agctacctgc gcctgtctgg tccgatcgtt tagccgctct      600
ttctaagaga cgggaatgta aatagaaaac atccctgggg aaagcctcac gacctggtgg      660
tcggcgtaac aataatgaca tttgtcgata tgctaccgcc tgtttactaa gatcatcata      720
gattattaat gcgtgcattc cattatcgcg gaaatattcc cccatggcac acccagaata      780
tggggccaaa aattgtagag gagcaggatc cgaagcggtg gctgctacaa gaatagaata      840
ttccaaagca ttcgcttctg aaagaatttg aactaattgt gccacagttg agcgtttctg      900
tccaatcgct acatagacac aatacaatgt ctcactctca gaggtggccc ttgagttcag      960
ttgcttttgg tttaatatgg tatcgatagc aatagcagtt tttccagttt gtcggtcccc     1020
gattataagt tctcgttgac cacgacctat aggaaccagg ctatctaccg cttttaaccc     1080
tgtttgcata ggctcgtgca cagatttacg ttcaataata ccagggcttt cacttcgac      1140
acgtcttcgc tcgtgatcgc ttagagcccc ccttccatca ataggtactc caagccatc      1200
gaccacacgc cctagcatag ccttccccgc aggaacatcc acaatagatc cagtgcgctt     1260
gacaagatct ccttctttaa tagcagtatc actaccaaag acaacaatcc ctacattctc     1320
attctcaaga ttcaaggcta ttcctttcac accgctggca aattcaacca tttccccagc     1380
ttgaatctcg ttcaatccat aaacacgtgc aattccatct ccaactgaga ccactcgacc     1440
gatctcatcc acttgaaaat tggtgtaaaa gttgctaatt cgactttcta atagacttgt     1500
tagttccgca gctcggggag aaagttccat aattcaatta agatagata gaagggagaa     1560
tgccgcttta gaaaaaaaga aaatcataa ggaaacattc tctatatact caccttaaat      1620
tacccccccaa atataatatt gatataaagt gagttcggcc catctctcgt cagatcgtgt    1680
gaaagtagac ccaaaaagcg gagctctctc tggtctctta cgaagacagc cccgccttgt     1740
aggtcaagtt cacttcgttt ctcattcaaa aagtcgcaaa aggcttcttg tgggttggaa     1800
tcggcatttt cggccacggc agggtgcgca gtcagtattt cttgataaat cgaatagcat     1860
gaatgccttt tctcacggat ctgaagatcc ctattctcga actcgagcaa tcggttgtat    1920
tcccttttgcg agggacaatt gtcgagttga gtctttactt ccgcccaatt cgaccccctc   1980
tcttcagaga gaagaaaagg gctcttttcc tgttccagtg ccaatagcct atttctcatc    2040
gatgcctcca aggctacatt gtgagtcacg gccaaggct ccgacaggac ctggagctcg     2100
aatgaatcct ccgaggagga gtttgatggg gtggaagggc ccggaagagg aagtggctgc    2160
ccccccccg aaacaacact gaaaacagca aaaaagaaa aagatctag aaaataaaca       2220
cacaagttag atagaaaata ggtgcgtaaa caacacccaa ataaggagat ggaaaaaga     2280
```

```
atagatatat atatgatata gagaagtcga aagccagatt tttgattcaa acgaaaacga    2340
tttctacgaa cgataaaggt cagggaaaaa agaaggattc caaaaagtac gagatttcca    2400
cccgtggtca ttatagcggt tccttctttt cctagaaaat gataaaaaaa aaaggcggta    2460
acaaagggca caaataacg aatgagagcc atggcaaaca taaaattggg gtacctcggt     2520
acgacctgcg cggttgttcc tatttcattt tcttcttcca agttctttcg cgcactgagt    2580
tacttacgga atctcagacc cccctcggca ggaccacagg cccgtgtaaa cacctcaacg    2640
aactcatgtg gacactcctc agcaccgagg acaatctctc aaatacacat gttgatgttg    2700
ttgacccgtt tttctttttct ttgctacgat tacgctacga tctttcttct cttatgatat    2760
tttttgataa gtcgagcctt cgctcttgcc tataataaga ggtcaaggat cgagtcgtct    2820
gttcatagtt tcacttcgct tctgccattc tgttcccctc ggactattaa gggaaagcaa    2880
ggcaaggaac ccttggtatg cacgagacaa gcataagaca ccaaccaaaa gtactctttc    2940
ggaatcaggt gagtcaaagg tcaggagctc aatcaaaact agctacactt ccctctcagc    3000
ctgcctgcaa tccggtgaaa ctgttagacg aagaggactc gtctttcatg cggaaagcga    3060
cccacggaag tcttctcact tggaatagag ctcaccagaa aaagacagg ttcaagtacg      3120 aaggctattc cgtgagttta gacggaagca ataactgat agttgtctgt gcccaaggtc      3180
agattatcga catcggtatt ggggtagcaa gaagatgcat tggctgataa catatccatc    3240
gcccttcctc ggtccgtccc catagcaagc ttcctattgg cttctcaccc cggactgaga    3300
ctcgctcttc tcgtccagaa gaatagttgt cttcctggtt aactagtcat tggtctttgg    3360
caccaaagaa agtcgagaag gttgggacgc aaggtggttg tcgctcaagc aactgtggaa    3420
gcagactccg tgaaaaagtc gtgtgcatca agaaaggga agggctctcc ctctctatct      3480
tgaacctagc tctgcccagc ttggatgaac aaagtgtgca atgcgtggag tgagatcact    3540 accataccttt tttccatttt tctagtgaac ataggcttcg agtgcgtacc aggcgagact    3600
atgactgagt caagcggaca cccgctaatc cgcgcttcca ttcgcgacct gaagccaagc    3660
cattgacgag cctcgaagga ccttttcaagc ctccccgctt cgattcgttt gctttcccttt    3720 tctcactctg aaagaaagaa gaaagccttg ctttgcctcc ttccttcttc gctaattgaa    3780
agctagactc acacgtctgc ttatgaagat tatggcttcc tcacttgttt gatttgaaat    3840
ggcacgatgc ttaacacatg taattggagt ctgtttcggg gcttacagaa gctcgtgcaa    3900
agaagattta taggagagaa gttccccatc tctcttaggc cttctgtctc ttgaaaaata    3960
ttgtattctt atgtttgaga tcgcctctgt gtgattcatc ctaagtagct aaccgaaaag    4020
gaactgactg aaaggactga taagagaaga ggctctaact gtttaaaggt aaaggaaagg    4080
aagccaggtg aaatcacccc ttgataaagg aaggctccta caaagagtcg accaggcctt    4140
gtagaagcga agatcgatgt ccgtcccatt cggcgaagca atcttggacc ctcttggctg    4200
cgctgtgctt ggatgcacta gtcttccaca cgccagcgat gagatgaaaa ctgcccccat    4260
tcagtggttc ccgtgccacc aaaatggcat agcatcgaaa gagtgaccgg aacctgtccc    4320
tgaccagctc gtaagtagca tcccgctgct ggtcggcaca gcgggcgtc aaaagcaagt       4380 ctttttgat tgcccgctg accttttcta aaagcacctt gggtcggagg ctggttgtaa       4440
agtaaagaag ggtggtgcgc tttcgaattc gattaatttt gatagaaaga agaaccagaa    4500
ttggtcctgg gtcgtatcgt ttttcaactg tccgctggta aatctggtct agcactacaa    4560
tgtctccatt gtgcggcgct atgaaagaga aaaagaattc tgcctcgcta gcctttttcac    4620 ctcttctctt ccgtcggtct tgtactgagc catcagaata gggatggtgc caagaaaggc    4680
```

| | | | | |
|---|---|---|---|---|
| agtttaatct | atatctgtag | aacgaacaaa | gcaaagatat tcaaataaag | aatttgtgag | 4740 |
| ggaatgacta | ttcatctatt | gtattttcat | ccaggcaaga aaaagtctat | ggaaagatgc | 4800 |
| tgtatatgtc | gcagccttct | tcttcttaaa | gaaaatgaac gaaggcccaa | gggcttttat | 4860 |
| ccatcagaca | tgaatgaaag | gggatgacac | cactctaatg attggaaaaa | tccttaatat | 4920 |
| cataaaggaa | aggtcttttt | cttaaaagct | tcagtaatag caaaagcagc | ctatctggaa | 4980 |
| tggcctactc | cttactcaag | caaagctgta | tgcaaccgca tagaggaagt | taagccaatc | 5040 |
| cctctatttt | catcttgaaa | gattcggaaa | aatagaacat gctccacccc | ttccttcgat | 5100 |
| tgctttcatt | tttggcccga | tcaggcttca | ccttcttatc gggatagcca | tttagcttgc | 5160 |
| tttcttggga | ctagccttga | atactagcca | ttttctcatc gcatcaagag | ggctttcaga | 5220 |
| gagagggctc | caaccctcta | taatcgagtg | atggtggaat gaccaatcca | gttccctcag | 5280 |
| gctggctttc | tccaagggca | gttttgtcct | gtccgctagg actggtctaa | atgtgcggga | 5340 |
| tcgatacatc | ggtagggagg | ctcggccaag | catcacggta gcagagccat | agggctctaa | 5400 |
| agagctgaga | acaaccgcac | tcagcacacc | tctgaattct tcttgacacg | tggcagtcat | 5460 |
| tgacttgatg | tggtaacttt | acattcttaa | agctttaggc gaactaaacg | attgactaga | 5520 |
| ataaattacc | ttattgcgct | cttcgccttc | tttctatcta gcaaacctaa | gaaaggaaag | 5580 |
| ggacaaaaag | tgggattaat | cctgatttct | ttggttagtt cttgtcatca | cacaaaacta | 5640 |
| gcgttcgcct | tctatgagta | aaatccattc | tctagcggat tccccggaga | tagtccgatt | 5700 |
| aatccagatg | ataagggaat | gactgatgag | actaccgaca cctttttatcg | agtaagtcat | 5760 |
| accgagcttg | gtgaaagaaa | aaaaatggta | ctagctaaag agaaggatca | gacaaatttc | 5820 |
| tttaaactct | catacaaagg | ggaaaaaagc | tacggttgaa agatcactgg | gtttaggagg | 5880 |
| aggctaggtt | agccgaaaga | tggttatcgg | ttcaagaacg taaggtgtcc | ccccttata | 5940 |
| taatataagg | aagtcacttt | ttctacgatg | ttcgagatct ttgtctcgca | gagggtgaaa | 6000 |
| tggcgatctg | tta | | | | 6013 |

<210> SEQ ID NO 2
<211> LENGTH: 1567
<212> TYPE: DNA
<213> ORGANISM: Nicotiana sylvestris

<400> SEQUENCE: 2

| | | | | |
|---|---|---|---|---|
| ttaaataaaa | gctaaagcac | tttcttttaa | gaatgtatct ggttccatct | ttctttcgtt | 60 |
| agttaagcca | ccttttttcta | aaaggattg | tagtaattct ggtttgacac | tatttggaat | 120 |
| ggctctctca | tattgagaaa | ttctgtctag | tggcattcga tcacagaatc | cattgacagc | 180 |
| tgcataaatg | actagaattt | gttttttcaat | tggcagtggt gcatattgtg | gttgtttcgg | 240 |
| tacttctgtc | agccttgcac | ctctattgag | taatgcctga gtcgcagcat | caaggtctga | 300 |
| gccaaattga | gcaagggcgg | ccacttcgcg | atattgtgcc aattccagtt | ttgaactacc | 360 |
| gcagacttgt | ttcatagttt | tcaactgagc | ggcagacccg acgcgactga | cagataagcc | 420 |
| gacgttaatc | gcaggtctaa | ttccgcgata | aaagagctct gtttccaaac | agatttgtcc | 480 |
| atcagtaatg | gggatcacat | tggtgggaat | ataggccgat acgtctccag | cctgtgtttc | 540 |
| aatgacgggt | aaggcggtca | agctacctgc | gcctgtctgg tccgatcgtt | tagccgctct | 600 |
| ttctaagaga | cgggaatgta | aatagaaaac | atcccctggg aaagcctcac | gacctggtgg | 660 |
| tcggcgtaac | aataatgaca | tttgtcgata | tgctaccgcc tgtttactaa | gatcatcata | 720 |

```
gattattaat gcgtgcattc cattatcgcg gaaatattcc cccatggcac acccagaata    780
tggggccaaa aattgtagag gagcaggatc cgaagcggtg gctgctacaa gaatagaata    840
ttccaaagca ttcgcttctg aaagaatttg aactaattgt gccacagttg agcgtttctg    900
tccaatcgct acatagacac aatacaatgt ctcactctca gaggtggccc ttgagttcag    960
ttgcttttgg tttaatatgg tatcgatagc aatagcagtt tttccagttt gtcggtcccc   1020
gattataagt tctcgttgac cacgacctat aggaaccagg ctatctaccg cttttaaccc   1080
tgtttgcata ggctcgtgca cagatttacg ttcaataata ccaggggctt tcacttcgac   1140
acgtcttcgc tcgtgatcgc ttagagcccc ccttccatca ataggtactc caagccatc    1200 gaccacacgc cctagcatag cctttcccgc aggaacatcc acaatagatc cagtgcgctt   1260
gacaagatct ccttctttaa tagcagtatc actaccaaag acaacaatcc ctacattctc   1320
attctcaaga ttcaaggcta ttcctttcac accgctggca aattcaacca tttccccagc   1380
ttgaatctcg ttcaatccat aaacacgtgc aatcccatct ccaactgaga ccactcgacc   1440
gatctcatcc acttgaaaat tggtgtaaaa gttgctaatt cgactttcta atagacttgt   1500
tagttccgca gctcggggag aaagttccat aattcaattc aagatagata gaagggagaa   1560
tgccgct                                                             1567

<210> SEQ ID NO 3
<211> LENGTH: 3515
<212> TYPE: DNA
<213> ORGANISM: Nicotiana sylvestris

<400> SEQUENCE: 3
tttcttctct tatgatattt attgaaaatt cgagccttcg ctcttgccta taattataat     60
aagaggtcaa ggatcgagtc gtctgttctt tcacttcgct tctgccattc tgtgctttcc    120
cctcgtacta ttaagggaaa gcaaggcaag gaaaccttgg tatgcacgag aaaagcatat    180
gacaccaacc aaaagtacgc tttcggaatc aggtgagtca aggtcagga gctcaatcaa    240 aactagctac acttccctct cagcctgcct gcaatccggt gaaactgtta gacgaagagg    300
acttgtcttt catgcggaaa gcgacccacg gaagtcttct cacttggaat agagctcacc    360
agaaaaaaga gaggttcaag tacgaaggct attccgtgag tttagacgga agcaaataac    420
tgatagttgt ctgtgcccaa ggtcagatta tcgacatctg tattgggta gcaagaagat    480 gcattggctg ataacatatc catcgccctt ccttggtccg tccccatagc aagcttccta    540
ttggcttctc accccggacg gagactcgct cttctcgtcc agaagaatag ttgtcttcct    600
ggttaactag tcattggtct ttggcaccaa agaaagtcga gaaggttggg acgcaaggtg    660
gttgtcgctc aagcaactgt ggaagcagac tccgtgaaaa agtcgtgtgc atcaaagaaa    720
agaaatggaa gggctctccc tctctatctt gaacctagct ctgcccagtt tggatgaaca    780
aagtgcgcaa tgcgtggagt gagatcacta ccatacccttt ttcaattttt ctagtgaaca    840
taggcttcga gtgcgtacca ggcgagacta tgactgagtc aagcggacac ccgctaatcc    900
gcgcttccat tcgcaacctg aagccaagcc attgacgagc cccgaaggac ctttcaagcc    960
tccccgcttc gattcgtttg ctttcccttt ctcactctga aagaaagaag aaagccttgc   1020
tttgcctcct tccttcttcg ctaattgaaa gctagactca cacgtctgct tatgaagatt   1080
atggcttcct cacttgacct tctttctagc cttttatttt tatttgaaat ggcacgatgc   1140
ttaacacatg taattggagt ctgttcgggg cttacagaa gctcgtgcaa agaagattta    1200
taggagagaa gttccccatc tctcttaggc cttctgtctc ttgaaaaata ttgtattctt   1260
```

```
tgagatcgcc tctgtgtgat tcatcctaag tagctaaccg aaaaggaact gactgaaagg    1320
actgataaga gaagaggctc taactgttta aaggtaaagg aaaggaagcc aggtgaaatc    1380 acccttgat aaaggaagac tcctacaaag agtcgaccag gccttgtaga agcgaagatc    1440
gatgtccgtc ccattcgacg aagcaatctt ggaccctctt ggttgcgctg tgcttggatg    1500
cactagtctt ccacacgcca gcgatgagat gaaaactgcc cccattcagt ggttcccgtg    1560
ccaccacaat ggcatggcat ctaaagagtg accggaacct gtccctgacc agctcgtaag   1620
tagcatcccg ctgctggtcg gcacagcggg gcgtcaaaag caagtctttt ttgattgccc    1680
cgcggacctt ttctaaaagc accttgggtc ggaggctggt tgtaaagtaa agaagggtgg    1740
tgcgctttcg aattcgattt cttttgatag aaagaagaac cccgtcccac gagcggaggg    1800
aggtcctggg tcgtatcgtt tttcaactgt ccgctggtaa atctggtcta gcactacaat    1860
gtctcgattg tgcggcgcta tgaaagagaa aaagaattct gcctcgctag ccttttcacc    1920
tcttctcttc cgtcggtctt gtactgagcc atcagaatag gatggtgcc aagaaaggaa     1980 gtttaatcta tatctgtaga acgaacaaag caaaaatatt caaataaaga atttgtgagg    2040
gaatgactat tcatctattg tattttcatc caggcaagaa aaagtctatg gaaagatgct    2100
gtatatgtcg cagccttctt aaacaaaatg aacgaaggcc caagggctat aattggtgta    2160
ctatccaaag acagaataga aaaatacaaa taagagaggc tttcccagag ccttcttttc    2220
tatggggtgg gaatccaata gggattcgat tcctcctctc ccgagtgcct gaacgcgcta    2280
tttaacctct caggtaggtc aaatggcatt ccgcttactg acctaatcga ctgttaggcc    2340
tacgggcttt tatccatcag acatgaatga aggggatga caccactcta atgattggaa      2400
aaatccttaa tatcataaag caacatatca taaggaaag gtctttttct taaaagcttc     2460
agtaatagca aaagcagcct atctggaatg gcctactcgt tactcaagca aagctgtatg    2520
caaccgcata gaggaagtta agccaatccc tctattttca tcttttaaga ttcggaaaaa    2580
tagaacatgc tctaccccctt ccttcgattg ctttcatttt tggcccgatc aggcttcatc   2640
ttcttatcgg gatagccatt tagcttggtt tcttgggact agccttgaat actagccatt    2700
ttatcatcgc atcaagaggg cttttcagaga gagggctcca accctctata atcgagtgat   2760
ggtggaatga ccaatccagt tccctcaggc tggctttctt caagggaagt tttgtcctgt    2820
ccgctaggac tggtctaaat gtgcgggatc gatacatcgg tagggaggct cggccaagca    2880
tcacggtagc agagccatag ggcgctaaag agctgagaac aaccgcactc agcacacctc    2940
tgaattcttc ttgacacgtg gcagtcattg acttgatgtg gtaactttac attctttaag    3000
ctttaggcga actaaacgat tgactagaat caattacctt attgcgctct tcgccttctt    3060
tctatctagc aaacctaaga aaggaaaggg acaaaaagtg ggattaatcc tgatttcttt    3120
ggttagttct tgtcatcaca taaaactagc gttctatgag taaaatccat tctctagcgg    3180
attcccatat gctgagatag tccgattaat ccagatgata agggaatgac tgatgagact    3240
accgatacct tttatcgagt aagtcatacc gagcttggtg aaagataaaa aatggtacta    3300
gctaaagaga aggatcagag aaatttcttt aaactctcat acaaaggga aaaaagctac     3360 ggttgaaaga tcactgggtt taggaggagg ctaggttagc cgaaagatgg ttatcggttc    3420
aagaacgtaa ggtgtccccc ccttatataa ggaagtaact ttttctacga tgttagagat    3480
ctttgtctcg cagagggtga aatggcgatc tgtta                               3515
```

<210> SEQ ID NO 4

```
<211> LENGTH: 102
<212> TYPE: PRT
<213> ORGANISM: Notonecta undulata

<400> SEQUENCE: 4

Met Thr Ala Thr Cys Gln Glu Glu Phe Arg Gly Val Leu Ser Ala Val
1               5                   10                  15

Val Leu Ser Ser Leu Glu Pro Tyr Gly Ser Ala Thr Val Met Leu Gly
            20                  25                  30

Arg Ala Ser Leu Pro Met Tyr Arg Ser Arg Thr Phe Arg Pro Val Leu
        35                  40                  45

Ala Asp Arg Thr Lys Leu Pro Leu Glu Lys Ala Ser Leu Arg Glu Leu
    50                  55                  60

Asp Trp Ser Phe His His His Ser Ile Ile Glu Gly Trp Ser Pro Leu
65                  70                  75                  80

Ser Glu Ser Pro Leu Asp Ala Met Arg Lys Trp Leu Val Phe Lys Ala
                85                  90                  95

Ser Pro Lys Lys Ala Ser
            100

<210> SEQ ID NO 5
<211> LENGTH: 102
<212> TYPE: PRT
<213> ORGANISM: Nicotiana sylvestris

<400> SEQUENCE: 5

Met Thr Ala Thr Cys Gln Glu Glu Phe Arg Gly Val Leu Ser Ala Val
1               5                   10                  15

Val Leu Ser Ser Leu Ala Pro Tyr Gly Ser Ala Thr Val Met Leu Gly
            20                  25                  30

Arg Ala Ser Leu Pro Met Tyr Arg Ser Arg Thr Phe Arg Pro Val Leu
        35                  40                  45

Ala Asp Arg Thr Lys Leu Pro Leu Lys Lys Ala Ser Leu Arg Glu Leu
    50                  55                  60

Asp Trp Ser Phe His His His Ser Ile Ile Glu Gly Trp Ser Pro Leu
65                  70                  75                  80

Ser Glu Ser Pro Leu Asp Ala Met Ile Lys Trp Leu Val Phe Lys Ala
                85                  90                  95

Ser Pro Lys Lys Pro Ser
            100

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
ttgctttgcc tccttccttc ttc                                     23

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
tctgtaagcc ccgaaacaga ctc                                     23
```

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
tcttacttag aataggtcgt cgattcagca                                              30

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ccactgattt ctgccgcttc cgtt                                                    24

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
acacattcca acctgcttga atacca                                                  26

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
tcttccgccc ccttccacaa ctat                                                    24

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
gagacattcc tccgctttca ggcg                                                    24

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
tggaaccgct aaggaaaggg ggtc                                                    24

<210> SEQ ID NO 14
<211> LENGTH: 24
<212> TYPE: DNA
<213> ORGANISM: Artificial Sequence
<220> FEATURE:

<223> OTHER INFORMATION: Primer

<400> SEQUENCE: 14
aacggcattc ccgtagcaat tggg                                    24

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
ggatgagatt gggtcccagc ggat                                    24

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
tttccaccac gacgtgcatt tcgt                                    24

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
tacaaattgc ggggcgtatc gacg                                    24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
tcggaagaaa ggtgggatcc ggac                                    24

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
tggtatgggg tcttatcgaa gcgc                                    24

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ccccgcccag tagtgcctct                                         20

-continued

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
ccgcgggcat cgcgataagt                                               20

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
cggccatcct ggtcctcagg a                                             21

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
tggggactcg cacgaggagg                                               20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ggcaggagcg caacgacctt                                               20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
agtcgggttg ctcacgcagc                                               20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tggtgtgctt cctgctcgcg                                               20

<210> SEQ ID NO 27
<211> LENGTH: 20
<212> TYPE: DNA
<213> ORGANISM: Artificial Sequence
<220> FEATURE:
<223> OTHER INFORMATION: Primer

```
<400> SEQUENCE: 27
tttctccgtg cccgttccgc                                              20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
aggtgcccgt agtaggccgg                                              20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
ttgggcttgg ctctgctcgc                                              20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
cacgactccc cctctccccg                                              20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tgcccgattc cccgacccat                                              20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
acgggaattg aacccgcgca                                              20

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
cgggttgcta actcaacgg                                               19

<210> SEQ ID NO 34
<211> LENGTH: 24
```

```
<212> TYPE: DNA
<213> ORGANISM: Artificial Sequence
<220> FEATURE:
<223> OTHER INFORMATION: Primer

<400> SEQUENCE: 34
tcaaatgata catagtgcga taca                                              24

<210> SEQ ID NO 35
<211> LENGTH: 18
<212> TYPE: DNA
<213> ORGANISM: Artificial Sequence
<220> FEATURE:
<223> OTHER INFORMATION: Primer

<400> SEQUENCE: 35
cgaatccctc tctttccg                                                    18

<210> SEQ ID NO 36
<211> LENGTH: 26
<212> TYPE: DNA
<213> ORGANISM: Artificial Sequence
<220> FEATURE:
<223> OTHER INFORMATION: Primer

<400> SEQUENCE: 36
gcctttgttt ggcaagctgc tgtaag                                            26

<210> SEQ ID NO 37
<211> LENGTH: 25
<212> TYPE: DNA
<213> ORGANISM: Artificial Sequence
<220> FEATURE:
<223> OTHER INFORMATION: Primer

<400> SEQUENCE: 37
ggcattgctc gtattcacgg tcttg                                             25

<210> SEQ ID NO 38
<211> LENGTH: 23
<212> TYPE: DNA
<213> ORGANISM: Artificial Sequence
<220> FEATURE:
<223> OTHER INFORMATION: Primer

<400> SEQUENCE: 38
ccactctgga aacggagata ccc                                               23

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
ctcgtttttt atcagaagct tgtg                                              24

<210> SEQ ID NO 40
<211> LENGTH: 22
<212> TYPE: DNA
<213> ORGANISM: Artificial Sequence
<220> FEATURE:
<223> OTHER INFORMATION: Primer

<400> SEQUENCE: 40
```
gatggccctc catggattca cc                                          22

<210> SEQ ID NO 41
<211> LENGTH: 25
<212> TYPE: DNA
<213> ORGANISM: Artificial Sequence
<220> FEATURE:
<223> OTHER INFORMATION: Primer

<400> SEQUENCE: 41
gaggattaat gtcagatcct caagg                                       25

<210> SEQ ID NO 42
<211> LENGTH: 23
<212> TYPE: DNA
<213> ORGANISM: Artificial Sequence
<220> FEATURE:
<223> OTHER INFORMATION: Primer

<400> SEQUENCE: 42
gatagacatc ggtactccag tgc                                         23

<210> SEQ ID NO 43
<211> LENGTH: 23
<212> TYPE: DNA
<213> ORGANISM: Artificial Sequence
<220> FEATURE:
<223> OTHER INFORMATION: Primer

<400> SEQUENCE: 43
gttacacaac aaccccttag agg                                         23

<210> SEQ ID NO 44
<211> LENGTH: 23
<212> TYPE: DNA
<213> ORGANISM: Artificial Sequence
<220> FEATURE:
<223> OTHER INFORMATION: Primer

<400> SEQUENCE: 44
gcacaaattc cgcttttat agg                                          23

<210> SEQ ID NO 45
<211> LENGTH: 26
<212> TYPE: DNA
<213> ORGANISM: Artificial Sequence
<220> FEATURE:
<223> OTHER INFORMATION: Primer

<400> SEQUENCE: 45
gcccaagcaa gacttactat atccat                                      26

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
ccagttcaaa tccgggtgtc                                             20

<210> SEQ ID NO 47
<211> LENGTH: 19
<212> TYPE: DNA
<213> ORGANISM: Artificial Sequence

```
<220> FEATURE:
<223> OTHER INFORMATION: Primer

<400> SEQUENCE: 47
taccaagggc tatagtcat                                                    19

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
gcccttttaa ctcagtggta                                                   20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
aacccgcatc ttctccttgg                                                   20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
gagagagagg gattcgaacc                                                   20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
ttcgttcgcc ggaaccagaa                                                   20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
aagaatgccc atgttgtggc                                                   20

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
cctattacag agatggtgcg attt                                              24
```

```
<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
cgatgcatat gtagaaagcc                                                    20

<210> SEQ ID NO 55
<211> LENGTH: 23
<212> TYPE: DNA
<213> ORGANISM: Artificial Sequence
<220> FEATURE:
<223> OTHER INFORMATION: Primer

<400> SEQUENCE: 55
tttttatgaa atacaagatg ctc                                                23

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
cgaaatcggt agacgctacg                                                    20

<210> SEQ ID NO 57
<211> LENGTH: 26
<212> TYPE: DNA
<213> ORGANISM: Artificial Sequence
<220> FEATURE:
<223> OTHER INFORMATION: Primer

<400> SEQUENCE: 57
gaaggaagga gacaaaaaat tgaggc                                             26

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
cgaaccgtag accttctcgg                                                    20

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
gtaaaatcaa gtccaccgcg                                                    20

<210> SEQ ID NO 60
<211> LENGTH: 23
<212> TYPE: DNA
<213> ORGANISM: Artificial Sequence
<220> FEATURE:
<223> OTHER INFORMATION: Primer
```

<400> SEQUENCE: 60
tctaggattt acatatacaa cat                                            23

<210> SEQ ID NO 61
<211> LENGTH: 22
<212> TYPE: DNA
<213> ORGANISM: Artificial Sequence
<220> FEATURE:
<223> OTHER INFORMATION: Primer

<400> SEQUENCE: 61
ctaataagaa gcctaatgaa cc                                             22

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
gcaggtaaaa gagtaattga ac                                             22

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
tactcatttt tgtacttgct gt                                             22

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
gcatctgtta ttttggcaca                                                20

<210> SEQ ID NO 65
<211> LENGTH: 24
<212> TYPE: DNA
<213> ORGANISM: Artificial Sequence
<220> FEATURE:
<223> OTHER INFORMATION: Primer

<400> SEQUENCE: 65
accatagaaa cgaaggaacc cact                                           24

<210> SEQ ID NO 66
<211> LENGTH: 23
<212> TYPE: DNA
<213> ORGANISM: Artificial Sequence
<220> FEATURE:
<223> OTHER INFORMATION: Primer

<400> SEQUENCE: 66
gctcgtattt tatctttgtt acc                                            23

<210> SEQ ID NO 67

```
<211> LENGTH: 26
<212> TYPE: DNA
<213> ORGANISM: Artificial Sequence
<220> FEATURE:
<223> OTHER INFORMATION: Primer

<400> SEQUENCE: 67
ccccttggac tgctacgaaa aacacc                                          26

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
tgccttggta tcgtgttcat ac                                              22

<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
cccagaaata ccttgtttac g                                               21

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
tggggaacta ctcctttgat                                                 20

<210> SEQ ID NO 71
<211> LENGTH: 22
<212> TYPE: DNA
<213> ORGANISM: Artificial Sequence
<220> FEATURE:
<223> OTHER INFORMATION: Primer

<400> SEQUENCE: 71
cgaggtataa tgacagaccg ag                                              22

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
attctacgtg caccttacg                                                  20

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
```

```
gggcatctac cattataccc                                               20

<210> SEQ ID NO 74
<211> LENGTH: 24
<212> TYPE: DNA
<213> ORGANISM: Artificial Sequence
<220> FEATURE:
<223> OTHER INFORMATION: Primer

<400> SEQUENCE: 74
agtctgaaac caagtggatt tatt                                          24

<210> SEQ ID NO 75
<211> LENGTH: 26
<212> TYPE: DNA
<213> ORGANISM: Artificial Sequence
<220> FEATURE:
<223> OTHER INFORMATION: Primer

<400> SEQUENCE: 75
gaagatacag gagcgaaaca atcaac                                        26

<210> SEQ ID NO 76
<211> LENGTH: 23
<212> TYPE: DNA
<213> ORGANISM: Artificial Sequence
<220> FEATURE:
<223> OTHER INFORMATION: Primer

<400> SEQUENCE: 76
gcttatgacc tccccctcta tgc                                           23

<210> SEQ ID NO 77
<211> LENGTH: 26
<212> TYPE: DNA
<213> ORGANISM: Artificial Sequence
<220> FEATURE:
<223> OTHER INFORMATION: Primer

<400> SEQUENCE: 77
tcttctagag aatctcctaa ttgttc                                        26

<210> SEQ ID NO 78
<211> LENGTH: 26
<212> TYPE: DNA
<213> ORGANISM: Artificial Sequence
<220> FEATURE:
<223> OTHER INFORMATION: Primer

<400> SEQUENCE: 78
cttcgaatat ggaattcaaa gggatc                                        26

<210> SEQ ID NO 79
<211> LENGTH: 24
<212> TYPE: DNA
<213> ORGANISM: Artificial Sequence
<220> FEATURE:
<223> OTHER INFORMATION: Primer

<400> SEQUENCE: 79
ctcaaacaag catgaaacgt atgc                                          24

<210> SEQ ID NO 80
<211> LENGTH: 22
<212> TYPE: DNA
```

```
<213> ORGANISM: Artificial Sequence
<220> FEATURE:
<223> OTHER INFORMATION: Primer

<400> SEQUENCE: 80
gagattttga gtctcgcgtg tc                                              22

<210> SEQ ID NO 81
<211> LENGTH: 26
<212> TYPE: DNA
<213> ORGANISM: Artificial Sequence
<220> FEATURE:
<223> OTHER INFORMATION: Primer

<400> SEQUENCE: 81
tcactgctta tatcccggt attggc                                           26

<210> SEQ ID NO 82
<211> LENGTH: 26
<212> TYPE: DNA
<213> ORGANISM: Artificial Sequence
<220> FEATURE:
<223> OTHER INFORMATION: Primer

<400> SEQUENCE: 82
gtgcaaaagc tctatttgcc tctgcc                                          26

<210> SEQ ID NO 83
<211> LENGTH: 26
<212> TYPE: DNA
<213> ORGANISM: Artificial Sequence
<220> FEATURE:
<223> OTHER INFORMATION: Primer

<400> SEQUENCE: 83
atcgaaagtt ggatctacat tggatc                                          26

<210> SEQ ID NO 84
<211> LENGTH: 26
<212> TYPE: DNA
<213> ORGANISM: Artificial Sequence
<220> FEATURE:
<223> OTHER INFORMATION: Primer

<400> SEQUENCE: 84
cgacactgac actgagagac gaaagc                                          26

<210> SEQ ID NO 85
<211> LENGTH: 26
<212> TYPE: DNA
<213> ORGANISM: Artificial Sequence
<220> FEATURE:
<223> OTHER INFORMATION: Primer

<400> SEQUENCE: 85
cgctacctta ggaccgttat agttac                                          26

<210> SEQ ID NO 86
<211> LENGTH: 26
<212> TYPE: DNA
<213> ORGANISM: Artificial Sequence
<220> FEATURE:
<223> OTHER INFORMATION: Primer

<400> SEQUENCE: 86
gaaactaagt ggaggtccga accgac                                          26
```

```
<210> SEQ ID NO 87
<211> LENGTH: 26
<212> TYPE: DNA
<213> ORGANISM: Artificial Sequence
<220> FEATURE:
<223> OTHER INFORMATION: Primer

<400> SEQUENCE: 87
agtggatccc tcttgttcct gtttag                                          26

<210> SEQ ID NO 88
<211> LENGTH: 25
<212> TYPE: DNA
<213> ORGANISM: Artificial Sequence
<220> FEATURE:
<223> OTHER INFORMATION: Primer

<400> SEQUENCE: 88
acagccgacc gctctaccac tgagc                                           25

<210> SEQ ID NO 89
<211> LENGTH: 25
<212> TYPE: DNA
<213> ORGANISM: Artificial Sequence
<220> FEATURE:
<223> OTHER INFORMATION: Primer

<400> SEQUENCE: 89
ggatcatacc tttcattcca cttcc                                           25

<210> SEQ ID NO 90
<211> LENGTH: 26
<212> TYPE: DNA
<213> ORGANISM: Artificial Sequence
<220> FEATURE:
<223> OTHER INFORMATION: Primer

<400> SEQUENCE: 90
atttcatctt tggaccaaaa acaagc                                          26

<210> SEQ ID NO 91
<211> LENGTH: 23
<212> TYPE: DNA
<213> ORGANISM: Artificial Sequence
<220> FEATURE:
<223> OTHER INFORMATION: Primer

<400> SEQUENCE: 91
gctaaacaaa ttgcttctgc tcc                                             23

<210> SEQ ID NO 92
<211> LENGTH: 26
<212> TYPE: DNA
<213> ORGANISM: Artificial Sequence
<220> FEATURE:
<223> OTHER INFORMATION: Primer

<400> SEQUENCE: 92
ggtcaatctt ttaggaatag ggttac                                          26

<210> SEQ ID NO 93
<211> LENGTH: 26
<212> TYPE: DNA
<213> ORGANISM: Artificial Sequence
<220> FEATURE:
```

<223> OTHER INFORMATION: Primer

<400> SEQUENCE: 93
ggacttctta tgtcgggata tggatc                                    26

<210> SEQ ID NO 94
<211> LENGTH: 26
<212> TYPE: DNA
<213> ORGANISM: Artificial Sequence
<220> FEATURE:
<223> OTHER INFORMATION: Primer

<400> SEQUENCE: 94
ctgcgcttcc actatatcaa ctgtac                                    26

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
tgaaaccttg gcatatatct                                           20

<210> SEQ ID NO 96
<211> LENGTH: 22
<212> TYPE: DNA
<213> ORGANISM: Artificial Sequence
<220> FEATURE:
<223> OTHER INFORMATION: Primer

<400> SEQUENCE: 96
aatttcgagg ttcttattta ct                                        22

<210> SEQ ID NO 97
<211> LENGTH: 21
<212> TYPE: DNA
<213> ORGANISM: Artificial Sequence
<220> FEATURE:
<223> OTHER INFORMATION: Primer

<400> SEQUENCE: 97
gacgatactg tagggtaggt c                                         21

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
ccatagaata cgaccctaat                                           20

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
ctagcactga aaaccgtctt                                           20

<210> SEQ ID NO 100
<211> LENGTH: 21
<212> TYPE: DNA
<213> ORGANISM: Artificial Sequence
<220> FEATURE:
<223> OTHER INFORMATION: Primer

<400> SEQUENCE: 100
aaagaagcac ggtcaaatag g                                              21

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
gcaacaacaa ggtgtcatgg                                                20

<210> SEQ ID NO 102
<211> LENGTH: 21
<212> TYPE: DNA
<213> ORGANISM: Artificial Sequence
<220> FEATURE:
<223> OTHER INFORMATION: Primer

<400> SEQUENCE: 102
tgtgtactac cggcctactg c                                              21

<210> SEQ ID NO 103
<211> LENGTH: 20
<212> TYPE: DNA
<213> ORGANISM: Artificial Sequence
<220> FEATURE:
<223> OTHER INFORMATION: Primer

<400> SEQUENCE: 103
ttctgctaaa ccgatcgtgg                                                20

<210> SEQ ID NO 104
<211> LENGTH: 21
<212> TYPE: DNA
<213> ORGANISM: Artificial Sequence
<220> FEATURE:
<223> OTHER INFORMATION: Primer

<400> SEQUENCE: 104
ggtcgatcca caatttaaac g                                              21

<210> SEQ ID NO 105
<211> LENGTH: 20
<212> TYPE: DNA
<213> ORGANISM: Artificial Sequence
<220> FEATURE:
<223> OTHER INFORMATION: Primer

<400> SEQUENCE: 105
gcacttgctc ctttgtaccc                                                20

<210> SEQ ID NO 106
<211> LENGTH: 20
<212> TYPE: DNA
<213> ORGANISM: Artificial Sequence
<220> FEATURE:
<223> OTHER INFORMATION: Primer

<400> SEQUENCE: 106
gaacctaacc tcgctccaca                                               20

<210> SEQ ID NO 107
<211> LENGTH: 20
<212> TYPE: DNA
<213> ORGANISM: Artificial Sequence
<220> FEATURE:
<223> OTHER INFORMATION: Primer

<400> SEQUENCE: 107
aaatggtagc tgcgaggaga                                               20

<210> SEQ ID NO 108
<211> LENGTH: 20
<212> TYPE: DNA
<213> ORGANISM: Artificial Sequence
<220> FEATURE:
<223> OTHER INFORMATION: Primer

<400> SEQUENCE: 108
gtctgtacct tcgccaaagc                                               20

<210> SEQ ID NO 109
<211> LENGTH: 20
<212> TYPE: DNA
<213> ORGANISM: Artificial Sequence
<220> FEATURE:
<223> OTHER INFORMATION: Primer

<400> SEQUENCE: 109
tcctcagaga actccagcgt                                               20

<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 110
cttcttccta agccgagggt                                               20

<210> SEQ ID NO 111
<211> LENGTH: 21
<212> TYPE: DNA
<213> ORGANISM: Artificial Sequence
<220> FEATURE:
<223> OTHER INFORMATION: Primer

<400> SEQUENCE: 111
ttgatgatag aacgcaactc g                                             21

<210> SEQ ID NO 112
<211> LENGTH: 20
<212> TYPE: DNA
<213> ORGANISM: Artificial Sequence
<220> FEATURE:
<223> OTHER INFORMATION: Primer

<400> SEQUENCE: 112
agttgcagga ttgttcgctt                                               20

<210> SEQ ID NO 113
<211> LENGTH: 20

```
<212> TYPE: DNA
<213> ORGANISM: Artificial Sequence
<220> FEATURE:
<223> OTHER INFORMATION: Primer

<400> SEQUENCE: 113
cgactgcaag agttggcaat                                              20

<210> SEQ ID NO 114
<211> LENGTH: 23
<212> TYPE: DNA
<213> ORGANISM: Artificial Sequence
<220> FEATURE:
<223> OTHER INFORMATION: Primer

<400> SEQUENCE: 114
tgatacagaa tatggcgaac ttt                                          23

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
ccgcttcatc attgaggttt                                              20

<210> SEQ ID NO 116
<211> LENGTH: 20
<212> TYPE: DNA
<213> ORGANISM: Artificial Sequence
<220> FEATURE:
<223> OTHER INFORMATION: Primer

<400> SEQUENCE: 116
aagatggcat atgggattgg                                              20

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
tgaatcggag gaagtgaatg                                              20

<210> SEQ ID NO 118
<211> LENGTH: 20
<212> TYPE: DNA
<213> ORGANISM: Artificial Sequence
<220> FEATURE:
<223> OTHER INFORMATION: Primer

<400> SEQUENCE: 118
cttctctctc caccgcagac                                              20

<210> SEQ ID NO 119
<211> LENGTH: 20
<212> TYPE: DNA
<213> ORGANISM: Artificial Sequence
<220> FEATURE:
<223> OTHER INFORMATION: Primer

<400> SEQUENCE: 119
```
acagttggat atggtggcgt                                            20

<210> SEQ ID NO 120
<211> LENGTH: 20
<212> TYPE: DNA
<213> ORGANISM: Artificial Sequence
<220> FEATURE:
<223> OTHER INFORMATION: Primer

<400> SEQUENCE: 120
cgttgcttag tctcgcactg                                            20

<210> SEQ ID NO 121
<211> LENGTH: 22
<212> TYPE: DNA
<213> ORGANISM: Artificial Sequence
<220> FEATURE:
<223> OTHER INFORMATION: Primer

<400> SEQUENCE: 121
ggttgatccg acactattac ga                                         22

<210> SEQ ID NO 122
<211> LENGTH: 22
<212> TYPE: DNA
<213> ORGANISM: Artificial Sequence
<220> FEATURE:
<223> OTHER INFORMATION: Primer

<400> SEQUENCE: 122
ttgttgctct ctcgagttct tt                                         22

<210> SEQ ID NO 123
<211> LENGTH: 18
<212> TYPE: DNA
<213> ORGANISM: Artificial Sequence
<220> FEATURE:
<223> OTHER INFORMATION: Primer

<400> SEQUENCE: 123
gcagtcgact cattggca                                              18

<210> SEQ ID NO 124
<211> LENGTH: 24
<212> TYPE: DNA
<213> ORGANISM: Artificial Sequence
<220> FEATURE:
<223> OTHER INFORMATION: Primer

<400> SEQUENCE: 124
gacaacaatc agtaaaggaa acga                                       24

<210> SEQ ID NO 125
<211> LENGTH: 20
<212> TYPE: DNA
<213> ORGANISM: Artificial Sequence
<220> FEATURE:
<223> OTHER INFORMATION: Primer

<400> SEQUENCE: 125
aatgcaagac cctgtcaacc                                            20

<210> SEQ ID NO 126
<211> LENGTH: 20
<212> TYPE: DNA
<213> ORGANISM: Artificial Sequence

```
<220> FEATURE:
<223> OTHER INFORMATION: Primer

<400> SEQUENCE: 126
aacaaaccgc tttccattct                                               20

<210> SEQ ID NO 127
<211> LENGTH: 20
<212> TYPE: DNA
<213> ORGANISM: Artificial Sequence
<220> FEATURE:
<223> OTHER INFORMATION: Primer

<400> SEQUENCE: 127
gaattaggcg ctttgggaat                                               20

<210> SEQ ID NO 128
<211> LENGTH: 20
<212> TYPE: DNA
<213> ORGANISM: Artificial Sequence
<220> FEATURE:
<223> OTHER INFORMATION: Primer

<400> SEQUENCE: 128
ttaggcggcg gtattcttat                                               20

<210> SEQ ID NO 129
<211> LENGTH: 20
<212> TYPE: DNA
<213> ORGANISM: Artificial Sequence
<220> FEATURE:
<223> OTHER INFORMATION: Primer

<400> SEQUENCE: 129
tatgcctcaa tcccttacgc                                               20

<210> SEQ ID NO 130
<211> LENGTH: 20
<212> TYPE: DNA
<213> ORGANISM: Artificial Sequence
<220> FEATURE:
<223> OTHER INFORMATION: Primer

<400> SEQUENCE: 130
aagctgccct agctcaatca                                               20

<210> SEQ ID NO 131
<211> LENGTH: 23
<212> TYPE: DNA
<213> ORGANISM: Artificial Sequence
<220> FEATURE:
<223> OTHER INFORMATION: Primer

<400> SEQUENCE: 131
aacatcacca tttccacaag ttt                                           23

<210> SEQ ID NO 132
<211> LENGTH: 20
<212> TYPE: DNA
<213> ORGANISM: Artificial Sequence
<220> FEATURE:
<223> OTHER INFORMATION: Primer

<400> SEQUENCE: 132
catttagccg ggaacattca                                               20
```

```
<210> SEQ ID NO 133
<211> LENGTH: 20
<212> TYPE: DNA
<213> ORGANISM: Artificial Sequence
<220> FEATURE:
<223> OTHER INFORMATION: Primer

<400> SEQUENCE: 133
catgggatac acacgcaaag                                              20

<210> SEQ ID NO 134
<211> LENGTH: 27
<212> TYPE: DNA
<213> ORGANISM: Artificial Sequence
<220> FEATURE:
<223> OTHER INFORMATION: Primer

<400> SEQUENCE: 134
tgacagctaa gctaataaca gtaaatg                                      27

<210> SEQ ID NO 135
<211> LENGTH: 21
<212> TYPE: DNA
<213> ORGANISM: Artificial Sequence
<220> FEATURE:
<223> OTHER INFORMATION: Primer

<400> SEQUENCE: 135
ggactttgga gtgtcaaatg c                                            21

<210> SEQ ID NO 136
<211> LENGTH: 20
<212> TYPE: DNA
<213> ORGANISM: Artificial Sequence
<220> FEATURE:
<223> OTHER INFORMATION: Primer

<400> SEQUENCE: 136
agccagccac caaatttatc                                              20

<210> SEQ ID NO 137
<211> LENGTH: 20
<212> TYPE: DNA
<213> ORGANISM: Artificial Sequence
<220> FEATURE:
<223> OTHER INFORMATION: Primer

<400> SEQUENCE: 137
ggaacattgc tcaagcccta                                              20

<210> SEQ ID NO 138
<211> LENGTH: 24
<212> TYPE: DNA
<213> ORGANISM: Artificial Sequence
<220> FEATURE:
<223> OTHER INFORMATION: Primer

<400> SEQUENCE: 138
tttctttctg tctgatgctt caat                                         24

<210> SEQ ID NO 139
<211> LENGTH: 20
<212> TYPE: DNA
<213> ORGANISM: Artificial Sequence
<220> FEATURE:
<223> OTHER INFORMATION: Primer
```

<400> SEQUENCE: 139
ttgtccatct cacttgctgc                                                    20

<210> SEQ ID NO 140
<211> LENGTH: 18
<212> TYPE: DNA
<213> ORGANISM: Artificial Sequence
<220> FEATURE:
<223> OTHER INFORMATION: Primer

<400> SEQUENCE: 140
acgctagagc atccaaca                                                      18

<210> SEQ ID NO 141
<211> LENGTH: 18
<212> TYPE: DNA
<213> ORGANISM: Artificial Sequence
<220> FEATURE:
<223> OTHER INFORMATION: Primer

<400> SEQUENCE: 141
tagtgaaagg caagcagg                                                      18

<210> SEQ ID NO 142
<211> LENGTH: 20
<212> TYPE: DNA
<213> ORGANISM: Artificial Sequence
<220> FEATURE:
<223> OTHER INFORMATION: Primer

<400> SEQUENCE: 142
tcaaatgagg gttgtagcca                                                    20

<210> SEQ ID NO 143
<211> LENGTH: 21
<212> TYPE: DNA
<213> ORGANISM: Artificial Sequence
<220> FEATURE:
<223> OTHER INFORMATION: Primer

<400> SEQUENCE: 143
tgcaatggct acacaagaag a                                                  21

<210> SEQ ID NO 144
<211> LENGTH: 20
<212> TYPE: DNA
<213> ORGANISM: Artificial Sequence
<220> FEATURE:
<223> OTHER INFORMATION: Primer

<400> SEQUENCE: 144
ttgaacacca attgcggtaa                                                    20

<210> SEQ ID NO 145
<211> LENGTH: 20
<212> TYPE: DNA
<213> ORGANISM: Artificial Sequence
<220> FEATURE:
<223> OTHER INFORMATION: Primer

<400> SEQUENCE: 145
aaattcttgg gtcatggtgg                                                    20

<210> SEQ ID NO 146

```
<211> LENGTH: 20
<212> TYPE: DNA
<213> ORGANISM: Artificial Sequence
<220> FEATURE:
<223> OTHER INFORMATION: Primer

<400> SEQUENCE: 146
aggaggcgaa gaaagaggag                                                    20

<210> SEQ ID NO 147
<211> LENGTH: 20
<212> TYPE: DNA
<213> ORGANISM: Artificial Sequence
<220> FEATURE:
<223> OTHER INFORMATION: Primer

<400> SEQUENCE: 147
cccatgaatt cgtaacagca                                                    20

<210> SEQ ID NO 148
<211> LENGTH: 20
<212> TYPE: DNA
<213> ORGANISM: Artificial Sequence
<220> FEATURE:
<223> OTHER INFORMATION: Primer

<400> SEQUENCE: 148
aatgtctgcc caatcgaaag                                                    20

<210> SEQ ID NO 149
<211> LENGTH: 20
<212> TYPE: DNA
<213> ORGANISM: Artificial Sequence
<220> FEATURE:
<223> OTHER INFORMATION: Primer

<400> SEQUENCE: 149
cgaataacga cactcgaacg                                                    20

<210> SEQ ID NO 150
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 150
aaaaccaata tcataacttt                                                    20

<210> SEQ ID NO 151
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 151
aaaaccaatc tcataacttt                                                    20

<210> SEQ ID NO 152
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 152
```
gaaacgaagt ggagcgaggg                                              20

<210> SEQ ID NO 153
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 153
gaaacgaagc ggagcgaggg                                              20

<210> SEQ ID NO 154
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 154
aaaaaattta tctcttttta                                              20

<210> SEQ ID NO 155
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 155
aaaaaatttc tctcttttta                                              20

<210> SEQ ID NO 156
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 156
ctttgttctg tagtctttca                                              20

<210> SEQ ID NO 157
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 157
ctttgttctc tagtctttca                                              20

<210> SEQ ID NO 158
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 158
ctcccatttg aaagattatt                                              20

<210> SEQ ID NO 159
<211> LENGTH: 20
<212> TYPE: DNA

```
<213> ORGANISM: Artificial Sequence
<220> FEATURE:
<223> OTHER INFORMATION: Mitochondrial DNA sequence

<400> SEQUENCE: 159
ctcccatttt aaagattatt                                                20

<210> SEQ ID NO 160
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 160
tgcacctccg tacaagtgct                                                20

<210> SEQ ID NO 161
<211> LENGTH: 10
<212> TYPE: DNA
<213> ORGANISM: Artificial Sequence
<220> FEATURE:
<223> OTHER INFORMATION: Mitochondrial DNA sequence

<400> SEQUENCE: 161
tgcacgtgct                                                           10

<210> SEQ ID NO 162
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 162
ttccggctgt ttccgtcatt                                                20

<210> SEQ ID NO 163
<211> LENGTH: 10
<212> TYPE: DNA
<213> ORGANISM: Artificial Sequence
<220> FEATURE:
<223> OTHER INFORMATION: Mitochondrial DNA sequence

<400> SEQUENCE: 163
ttccgtcatt                                                           10

<210> SEQ ID NO 164
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 164
aagaaaaaag aaaagtcgag                                                20

<210> SEQ ID NO 165
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 165
aagaaaaaat caaagtcgag                                                20
```

-continued

<210> SEQ ID NO 166
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 166
ggatcagact actcctggtg                                              20

<210> SEQ ID NO 167
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 167
ggatcagacc actcctggtg                                              20

<210> SEQ ID NO 168
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 168
agcaaaactc gaacggatag                                              20

<210> SEQ ID NO 169
<211> LENGTH: 20
<212> TYPE: DNA
<213> ORGANISM: Artificial Sequence
<220> FEATURE:
<223> OTHER INFORMATION: Mitochondrial DNA sequence

<400> SEQUENCE: 169
agcaaaacta gaacggatag                                              20

<210> SEQ ID NO 170
<211> LENGTH: 23
<212> TYPE: DNA
<213> ORGANISM: Artificial Sequence
<220> FEATURE:
<223> OTHER INFORMATION: Plastid sequence polymorphism

<400> SEQUENCE: 170
tagagaatca aaattgattt acc                                          23

<210> SEQ ID NO 171
<211> LENGTH: 23
<212> TYPE: DNA
<213> ORGANISM: Artificial Sequence
<220> FEATURE:
<223> OTHER INFORMATION: Plastid sequence polymorphism

<400> SEQUENCE: 171
tagaaaatca aaatcgattt acc                                          23

<210> SEQ ID NO 172
<211> LENGTH: 23
<212> TYPE: DNA
<213> ORGANISM: Artificial Sequence
<220> FEATURE:

<223> OTHER INFORMATION: Plastid sequence polymorphism

<400> SEQUENCE: 172
tctgttatgg atttcgttgc taa                                    23

<210> SEQ ID NO 173
<211> LENGTH: 23
<212> TYPE: DNA
<213> ORGANISM: Artificial Sequence
<220> FEATURE:
<223> OTHER INFORMATION: Plastid sequence polymorphism

<400> SEQUENCE: 173
tatgttatgg atttcgttgt tca                                    23

<210> SEQ ID NO 174
<211> LENGTH: 20
<212> TYPE: DNA
<213> ORGANISM: Artificial Sequence
<220> FEATURE:
<223> OTHER INFORMATION: Plastid sequence polymorphism

<400> SEQUENCE: 174
tcaaaatcaa ataatctgta                                        20

<210> SEQ ID NO 175
<211> LENGTH: 14
<212> TYPE: DNA
<213> ORGANISM: Artificial Sequence
<220> FEATURE:
<223> OTHER INFORMATION: Plastid sequence polymorphism

<400> SEQUENCE: 175
tcaaataatc cgta                                              14

<210> SEQ ID NO 176
<211> LENGTH: 23
<212> TYPE: DNA
<213> ORGANISM: Artificial Sequence
<220> FEATURE:
<223> OTHER INFORMATION: Plastid sequence polymorphism

<400> SEQUENCE: 176
caacgcctac attgcatttg cag                                    23

<210> SEQ ID NO 177
<211> LENGTH: 23
<212> TYPE: DNA
<213> ORGANISM: Artificial Sequence
<220> FEATURE:
<223> OTHER INFORMATION: Plastid sequence polymorphism

<400> SEQUENCE: 177
caatgcctat attgcatttg cag                                    23

<210> SEQ ID NO 178
<211> LENGTH: 23
<212> TYPE: DNA
<213> ORGANISM: Artificial Sequence
<220> FEATURE:
<223> OTHER INFORMATION: Plastid sequence polymorphism

<400> SEQUENCE: 178
ttagaaatgt ttcccttgat tga                                    23

```
<210> SEQ ID NO 179
<211> LENGTH: 23
<212> TYPE: DNA
<213> ORGANISM: Artificial Sequence
<220> FEATURE:
<223> OTHER INFORMATION: Plastid sequence polymorphism

<400> SEQUENCE: 179
ttataaatgt tccccttgat tga                                              23

<210> SEQ ID NO 180
<211> LENGTH: 20
<212> TYPE: DNA
<213> ORGANISM: Artificial Sequence
<220> FEATURE:
<223> OTHER INFORMATION: Plastid sequence polymorphism

<400> SEQUENCE: 180
agtaaattca gccaactaag                                                  20

<210> SEQ ID NO 181
<211> LENGTH: 20
<212> TYPE: DNA
<213> ORGANISM: Artificial Sequence
<220> FEATURE:
<223> OTHER INFORMATION: Plastid sequence polymorphism

<400> SEQUENCE: 181
agtcaattca gccaacaaag                                                  20

<210> SEQ ID NO 182
<211> LENGTH: 18
<212> TYPE: DNA
<213> ORGANISM: Artificial Sequence
<220> FEATURE:
<223> OTHER INFORMATION: Plastid sequence polymorphism

<400> SEQUENCE: 182
atctcgactc ctttcaat                                                    18

<210> SEQ ID NO 183
<211> LENGTH: 23
<212> TYPE: DNA
<213> ORGANISM: Artificial Sequence
<220> FEATURE:
<223> OTHER INFORMATION: Plastid sequence polymorphism

<400> SEQUENCE: 183
atcgcgactc ctttcctttc aat                                              23

<210> SEQ ID NO 184
<211> LENGTH: 14
<212> TYPE: DNA
<213> ORGANISM: Artificial Sequence
<220> FEATURE:
<223> OTHER INFORMATION: mitochondrial DNA

<400> SEQUENCE: 184
cttattgact caag                                                        14

<210> SEQ ID NO 185
<211> LENGTH: 11
<212> TYPE: DNA
<213> ORGANISM: Artificial Sequence
<220> FEATURE:
<223> OTHER INFORMATION: mitochondrial DNA
```

```
<400> SEQUENCE: 185
cctccgtaca a                                                              11

<210> SEQ ID NO 186
<211> LENGTH: 11
<212> TYPE: DNA
<213> ORGANISM: Artificial Sequence
<220> FEATURE:
<223> OTHER INFORMATION: mitochondrial DNA

<400> SEQUENCE: 186
agtttccggc t                                                              11

<210> SEQ ID NO 187
<211> LENGTH: 14
<212> TYPE: DNA
<213> ORGANISM: Artificial Sequence
<220> FEATURE:
<223> OTHER INFORMATION: mitochondrial DNA

<400> SEQUENCE: 187
cttattgact caag                                                           14

<210> SEQ ID NO 188
<211> LENGTH: 10
<212> TYPE: DNA
<213> ORGANISM: Artificial Sequence
<220> FEATURE:
<223> OTHER INFORMATION: mitochondrial DNA

<400> SEQUENCE: 188
ggggtgtcac                                                                10

<210> SEQ ID NO 189
<211> LENGTH: 11
<212> TYPE: DNA
<213> ORGANISM: Artificial Sequence
<220> FEATURE:
<223> OTHER INFORMATION: mitochondrial DNA

<400> SEQUENCE: 189
agaaaaatcc c                                                              11

<210> SEQ ID NO 190
<211> LENGTH: 11
<212> TYPE: DNA
<213> ORGANISM: Artificial Sequence
<220> FEATURE:
<223> OTHER INFORMATION: mitochondrial DNA

<400> SEQUENCE: 190
cctccgtaca a                                                              11

<210> SEQ ID NO 191
<211> LENGTH: 10
<212> TYPE: DNA
<213> ORGANISM: Artificial Sequence
<220> FEATURE:
<223> OTHER INFORMATION: mitochondrial DNA

<400> SEQUENCE: 191
gggaatgagt                                                                10

<210> SEQ ID NO 192
<211> LENGTH: 11
```

```
<212> TYPE: DNA
<213> ORGANISM: Artificial Sequence
<220> FEATURE:
<223> OTHER INFORMATION: mitochondrial DNA

<400> SEQUENCE: 192
agtttccggc t                                                            11

<210> SEQ ID NO 193
<211> LENGTH: 11
<212> TYPE: DNA
<213> ORGANISM: Artificial Sequence
<220> FEATURE:
<223> OTHER INFORMATION: mitochondrial DNA

<400> SEQUENCE: 193
agaaaaatcc c                                                            11

<210> SEQ ID NO 194
<211> LENGTH: 31
<212> TYPE: DNA
<213> ORGANISM: Artificial Sequence
<220> FEATURE:
<223> OTHER INFORMATION: mitochondrial DNA

<400> SEQUENCE: 194
ggctcctctg cttacagtca agtggctttc a                                      31

<210> SEQ ID NO 195
<211> LENGTH: 39
<212> TYPE: DNA
<213> ORGANISM: Artificial Sequence
<220> FEATURE:
<223> OTHER INFORMATION: mitochondrial DNA

<400> SEQUENCE: 195
tcccctctcc tctgaggccg atcgcatcca cttttggag                              39

<210> SEQ ID NO 196
<211> LENGTH: 22
<212> TYPE: DNA
<213> ORGANISM: Artificial Sequence
<220> FEATURE:
<223> OTHER INFORMATION: mitochondrial DNA

<400> SEQUENCE: 196
gaccttcttt ctagcctttt at                                                22

<210> SEQ ID NO 197
<211> LENGTH: 11
<212> TYPE: DNA
<213> ORGANISM: Artificial Sequence
<220> FEATURE:
<223> OTHER INFORMATION: mitochondrial DNA

<400> SEQUENCE: 197
acgagcggag g                                                            11

<210> SEQ ID NO 198
<211> LENGTH: 16
<212> TYPE: DNA
<213> ORGANISM: Artificial Sequence
<220> FEATURE:
<223> OTHER INFORMATION: mitochondrial DNA

<400> SEQUENCE: 198
```

-continued

```
aatatcataa agcaac                                              16

<210> SEQ ID NO 199
<211> LENGTH: 13
<212> TYPE: DNA
<213> ORGANISM: Artificial Sequence
<220> FEATURE:
<223> OTHER INFORMATION: mitochondrial DNA

<400> SEQUENCE: 199
agtcctcgat tcg                                                 13

<210> SEQ ID NO 200
<211> LENGTH: 10
<212> TYPE: DNA
<213> ORGANISM: Artificial Sequence
<220> FEATURE:
<223> OTHER INFORMATION: mitochondrial DNA

<400> SEQUENCE: 200
ggggtgtcac                                                     10

<210> SEQ ID NO 201
<211> LENGTH: 11
<212> TYPE: DNA
<213> ORGANISM: Artificial Sequence
<220> FEATURE:
<223> OTHER INFORMATION: mitochondrial DNA

<400> SEQUENCE: 201
agaaaaatcc c                                                   11

<210> SEQ ID NO 202
<211> LENGTH: 22
<212> TYPE: DNA
<213> ORGANISM: Artificial Sequence
<220> FEATURE:
<223> OTHER INFORMATION: Primer

<400> SEQUENCE: 202
agtgatctca ctccacgcat tg                                       22

<210> SEQ ID NO 203
<211> LENGTH: 22
<212> TYPE: DNA
<213> ORGANISM: Artificial Sequence
<220> FEATURE:
<223> OTHER INFORMATION: Primer

<400> SEQUENCE: 203
ttccgtgagt ttagacggaa gc                                       22

<210> SEQ ID NO 204
<211> LENGTH: 21
<212> TYPE: DNA
<213> ORGANISM: Artificial Sequence
<220> FEATURE:
<223> OTHER INFORMATION: Primer

<400> SEQUENCE: 204
acagtttcac cggattgcag g                                        21

<210> SEQ ID NO 205
<211> LENGTH: 22
<212> TYPE: DNA
<213> ORGANISM: Artificial Sequence
```

```
<220> FEATURE:
<223> OTHER INFORMATION: Primer

<400> SEQUENCE: 205
gttctttcgc gcactgagtt ac                                              22

<210> SEQ ID NO 206
<211> LENGTH: 26
<212> TYPE: DNA
<213> ORGANISM: Artificial Sequence
<220> FEATURE:
<223> OTHER INFORMATION: Primer

<400> SEQUENCE: 206
tcgtagaaat cgttttcgtt tgaatc                                          26

<210> SEQ ID NO 207
<211> LENGTH: 23
<212> TYPE: DNA
<213> ORGANISM: Artificial Sequence
<220> FEATURE:
<223> OTHER INFORMATION: Primer

<400> SEQUENCE: 207
agcatgaatg cctttttctca cgg                                            23

<210> SEQ ID NO 208
<211> LENGTH: 20
<212> TYPE: DNA
<213> ORGANISM: Artificial Sequence
<220> FEATURE:
<223> OTHER INFORMATION: Primer

<400> SEQUENCE: 208
gacctgcgat taacgtcggc                                                 20

<210> SEQ ID NO 209
<211> LENGTH: 26
<212> TYPE: DNA
<213> ORGANISM: Artificial Sequence
<220> FEATURE:
<223> OTHER INFORMATION: Primer

<400> SEQUENCE: 209
tccatctttc tttcgttagt taagcc                                          26

<210> SEQ ID NO 210
<211> LENGTH: 24
<212> TYPE: DNA
<213> ORGANISM: Artificial Sequence
<220> FEATURE:
<223> OTHER INFORMATION: Primer

<400> SEQUENCE: 210
aggacgagtg tcctacctaa ttca                                            24

<210> SEQ ID NO 211
<211> LENGTH: 22
<212> TYPE: DNA
<213> ORGANISM: Artificial Sequence
<220> FEATURE:
<223> OTHER INFORMATION: Primer

<400> SEQUENCE: 211
atcttggcca aatgccaatc ct                                              22
```

```
<210> SEQ ID NO 212
<211> LENGTH: 22
<212> TYPE: DNA
<213> ORGANISM: Artificial Sequence
<220> FEATURE:
<223> OTHER INFORMATION: Primer

<400> SEQUENCE: 212
attcctggag tcctacgcta cg                                              22

<210> SEQ ID NO 213
<211> LENGTH: 22
<212> TYPE: DNA
<213> ORGANISM: Artificial Sequence
<220> FEATURE:
<223> OTHER INFORMATION: Primer

<400> SEQUENCE: 213
ttattcactt gtgctggtgg cg                                              22

<210> SEQ ID NO 214
<211> LENGTH: 24
<212> TYPE: DNA
<213> ORGANISM: Artificial Sequence
<220> FEATURE:
<223> OTHER INFORMATION: Primer

<400> SEQUENCE: 214
agaagctgtg atcgaggaag cccc                                            24

<210> SEQ ID NO 215
<211> LENGTH: 24
<212> TYPE: DNA
<213> ORGANISM: Artificial Sequence
<220> FEATURE:
<223> OTHER INFORMATION: Primer

<400> SEQUENCE: 215
gctctgaagg gagagttgag cgga                                            24

<210> SEQ ID NO 216
<211> LENGTH: 23
<212> TYPE: DNA
<213> ORGANISM: Artificial Sequence
<220> FEATURE:
<223> OTHER INFORMATION: Primer

<400> SEQUENCE: 216
ttgagcgttt gaagtggacg aac                                             23

<210> SEQ ID NO 217
<211> LENGTH: 23
<212> TYPE: DNA
<213> ORGANISM: Artificial Sequence
<220> FEATURE:
<223> OTHER INFORMATION: Primer

<400> SEQUENCE: 217
agatcgggct gtctgtacct ttg                                             23

<210> SEQ ID NO 218
<211> LENGTH: 28
<212> TYPE: DNA
<213> ORGANISM: Artificial Sequence
<220> FEATURE:
<223> OTHER INFORMATION: Primer
```

```
<400> SEQUENCE: 218
ccgctaatga gataacttca atttcgac                                        28

<210> SEQ ID NO 219
<211> LENGTH: 26
<212> TYPE: DNA
<213> ORGANISM: Artificial Sequence
<220> FEATURE:
<223> OTHER INFORMATION: Primer

<400> SEQUENCE: 219
tggatttctc tacaagttga tcgctg                                          26

<210> SEQ ID NO 220
<211> LENGTH: 23
<212> TYPE: DNA
<213> ORGANISM: Artificial Sequence
<220> FEATURE:
<223> OTHER INFORMATION: Primer

<400> SEQUENCE: 220
gttccaagtg actagcttgg ctg                                             23

<210> SEQ ID NO 221
<211> LENGTH: 23
<212> TYPE: DNA
<213> ORGANISM: Artificial Sequence
<220> FEATURE:
<223> OTHER INFORMATION: Primer

<400> SEQUENCE: 221
agctagaaaa aggaaagcgg cac                                             23

<210> SEQ ID NO 222
<211> LENGTH: 26
<212> TYPE: DNA
<213> ORGANISM: Artificial Sequence
<220> FEATURE:
<223> OTHER INFORMATION: Primer

<400> SEQUENCE: 222
tgaaaccctt gcttgtttat cccgcc                                          26

<210> SEQ ID NO 223
<211> LENGTH: 23
<212> TYPE: DNA
<213> ORGANISM: Artificial Sequence
<220> FEATURE:
<223> OTHER INFORMATION: Primer

<400> SEQUENCE: 223
tagatttagc caattcgggt gcg                                             23

<210> SEQ ID NO 224
<211> LENGTH: 24
<212> TYPE: DNA
<213> ORGANISM: Artificial Sequence
<220> FEATURE:
<223> OTHER INFORMATION: Primer

<400> SEQUENCE: 224
gggcgaagga tattcatgat atcc                                            24

<210> SEQ ID NO 225
```

```
<211> LENGTH: 23
<212> TYPE: DNA
<213> ORGANISM: Artificial Sequence
<220> FEATURE:
<223> OTHER INFORMATION: Primer

<400> SEQUENCE: 225
aggtccgcta ccaaagaatt agg                                              23

<210> SEQ ID NO 226
<211> LENGTH: 24
<212> TYPE: DNA
<213> ORGANISM: Artificial Sequence
<220> FEATURE:
<223> OTHER INFORMATION: Primer

<400> SEQUENCE: 226
gcttcgatga tcaacccctg gcac                                             24

<210> SEQ ID NO 227
<211> LENGTH: 24
<212> TYPE: DNA
<213> ORGANISM: Artificial Sequence
<220> FEATURE:
<223> OTHER INFORMATION: Primer

<400> SEQUENCE: 227
ccaaatacaa gggagcgggc actg                                             24

<210> SEQ ID NO 228
<211> LENGTH: 24
<212> TYPE: DNA
<213> ORGANISM: Artificial Sequence
<220> FEATURE:
<223> OTHER INFORMATION: Primer

<400> SEQUENCE: 228
atcagaagca tccagcagca ccac                                             24

<210> SEQ ID NO 229
<211> LENGTH: 24
<212> TYPE: DNA
<213> ORGANISM: Artificial Sequence
<220> FEATURE:
<223> OTHER INFORMATION: Primer

<400> SEQUENCE: 229
gctctgctgc atgacggagt gatc                                             24

<210> SEQ ID NO 230
<211> LENGTH: 23
<212> TYPE: DNA
<213> ORGANISM: Artificial Sequence
<220> FEATURE:
<223> OTHER INFORMATION: Primer

<400> SEQUENCE: 230
ggtaccggtt atgagccaca ttc                                              23

<210> SEQ ID NO 231
<211> LENGTH: 23
<212> TYPE: DNA
<213> ORGANISM: Artificial Sequence
<220> FEATURE:
<223> OTHER INFORMATION: Primer

<400> SEQUENCE: 231
```
gtcaagtcaa tagcagccag agc                                          23

<210> SEQ ID NO 232
<211> LENGTH: 26
<212> TYPE: DNA
<213> ORGANISM: Artificial Sequence
<220> FEATURE:
<223> OTHER INFORMATION: Primer

<400> SEQUENCE: 232
gggtagctac aagcataaac cggatt                                       26

<210> SEQ ID NO 233
<211> LENGTH: 23
<212> TYPE: DNA
<213> ORGANISM: Artificial Sequence
<220> FEATURE:
<223> OTHER INFORMATION: Primer

<400> SEQUENCE: 233
ttcggactgt cttgttttca ggc                                          23

<210> SEQ ID NO 234
<211> LENGTH: 23
<212> TYPE: DNA
<213> ORGANISM: Artificial Sequence
<220> FEATURE:
<223> OTHER INFORMATION: Primer

<400> SEQUENCE: 234
agtacggaac gagccttgtc tac                                          23

<210> SEQ ID NO 235
<211> LENGTH: 23
<212> TYPE: DNA
<213> ORGANISM: Artificial Sequence
<220> FEATURE:
<223> OTHER INFORMATION: Primer

<400> SEQUENCE: 235
ctccataagc atccaaagct gcc                                          23

<210> SEQ ID NO 236
<211> LENGTH: 23
<212> TYPE: DNA
<213> ORGANISM: Artificial Sequence
<220> FEATURE:
<223> OTHER INFORMATION: Primer

<400> SEQUENCE: 236
tgtactgtgc cgtatcagac cag                                          23

<210> SEQ ID NO 237
<211> LENGTH: 23
<212> TYPE: DNA
<213> ORGANISM: Artificial Sequence
<220> FEATURE:
<223> OTHER INFORMATION: Primer

<400> SEQUENCE: 237
gggtttacag gagatcccag agg                                          23

<210> SEQ ID NO 238
<211> LENGTH: 24
<212> TYPE: DNA

```
<213> ORGANISM: Artificial Sequence
<220> FEATURE:
<223> OTHER INFORMATION: Primer

<400> SEQUENCE: 238
acccgaccag ggatggacgt aaac                                                24

<210> SEQ ID NO 239
<211> LENGTH: 24
<212> TYPE: DNA
<213> ORGANISM: Artificial Sequence
<220> FEATURE:
<223> OTHER INFORMATION: Primer

<400> SEQUENCE: 239
aggtgcctct acatgagctt cggg                                                24

<210> SEQ ID NO 240
<211> LENGTH: 24
<212> TYPE: DNA
<213> ORGANISM: Artificial Sequence
<220> FEATURE:
<223> OTHER INFORMATION: Primer

<400> SEQUENCE: 240
cgcctggaag tccgaggacc ttta                                                24

<210> SEQ ID NO 241
<211> LENGTH: 24
<212> TYPE: DNA
<213> ORGANISM: Artificial Sequence
<220> FEATURE:
<223> OTHER INFORMATION: Primer

<400> SEQUENCE: 241
ctccgaaagc gttttccttc cccc                                                24

<210> SEQ ID NO 242
<211> LENGTH: 23
<212> TYPE: DNA
<213> ORGANISM: Artificial Sequence
<220> FEATURE:
<223> OTHER INFORMATION: Primer

<400> SEQUENCE: 242
tacggtgcgt cttatctgaa ggg                                                 23

<210> SEQ ID NO 243
<211> LENGTH: 23
<212> TYPE: DNA
<213> ORGANISM: Artificial Sequence
<220> FEATURE:
<223> OTHER INFORMATION: Primer

<400> SEQUENCE: 243
cacaagtttt gaattcgccg ctg                                                 23

<210> SEQ ID NO 244
<211> LENGTH: 26
<212> TYPE: DNA
<213> ORGANISM: Artificial Sequence
<220> FEATURE:
<223> OTHER INFORMATION: Primer

<400> SEQUENCE: 244
catgcaaatt gatttgtccc cgagat                                              26
```

```
<210> SEQ ID NO 245
<211> LENGTH: 23
<212> TYPE: DNA
<213> ORGANISM: Artificial Sequence
<220> FEATURE:
<223> OTHER INFORMATION: Primer

<400> SEQUENCE: 245 aaagggaga gaagacgata gcc                                              23

<210> SEQ ID NO 246
<211> LENGTH: 27
<212> TYPE: DNA
<213> ORGANISM: Artificial Sequence
<220> FEATURE:
<223> OTHER INFORMATION: Primer

<400> SEQUENCE: 246
atgataaaca ttcctgaggg aaagtgc                                         27

<210> SEQ ID NO 247
<211> LENGTH: 23
<212> TYPE: DNA
<213> ORGANISM: Artificial Sequence
<220> FEATURE:
<223> OTHER INFORMATION: Primer

<400> SEQUENCE: 247
gcatgtttgg gatacgtttg gtg                                             23

<210> SEQ ID NO 248
<211> LENGTH: 24
<212> TYPE: DNA
<213> ORGANISM: Artificial Sequence
<220> FEATURE:
<223> OTHER INFORMATION: Primer

<400> SEQUENCE: 248
tgtatcaccg agacacccga aggg                                            24

<210> SEQ ID NO 249
<211> LENGTH: 24
<212> TYPE: DNA
<213> ORGANISM: Artificial Sequence
<220> FEATURE:
<223> OTHER INFORMATION: Primer

<400> SEQUENCE: 249
cggatcgaat cagagttcac gccg                                            24

<210> SEQ ID NO 250
<211> LENGTH: 23
<212> TYPE: DNA
<213> ORGANISM: Artificial Sequence
<220> FEATURE:
<223> OTHER INFORMATION: Primer

<400> SEQUENCE: 250
atctggagga agcatctggt cac                                             23

<210> SEQ ID NO 251
<211> LENGTH: 23
<212> TYPE: DNA
<213> ORGANISM: Artificial Sequence
<220> FEATURE:
```

<223> OTHER INFORMATION: Primer

<400> SEQUENCE: 251
tctgttgaag gaagaagccc ctc                                            23

<210> SEQ ID NO 252
<211> LENGTH: 24
<212> TYPE: DNA
<213> ORGANISM: Artificial Sequence
<220> FEATURE:
<223> OTHER INFORMATION: Primer

<400> SEQUENCE: 252
agttgctctt tgcccaaagc cctc                                           24

<210> SEQ ID NO 253
<211> LENGTH: 24
<212> TYPE: DNA
<213> ORGANISM: Artificial Sequence
<220> FEATURE:
<223> OTHER INFORMATION: Primer

<400> SEQUENCE: 253
tgttaggcat tgaaccccac ccca                                           24

<210> SEQ ID NO 254
<211> LENGTH: 23
<212> TYPE: DNA
<213> ORGANISM: Artificial Sequence
<220> FEATURE:
<223> OTHER INFORMATION: Primer

<400> SEQUENCE: 254
gaaggagtta ggaggatgga gcg                                            23

<210> SEQ ID NO 255
<211> LENGTH: 23
<212> TYPE: DNA
<213> ORGANISM: Artificial Sequence
<220> FEATURE:
<223> OTHER INFORMATION: Primer

<400> SEQUENCE: 255
gactctttgg cctttagact cgc                                            23

<210> SEQ ID NO 256
<211> LENGTH: 24
<212> TYPE: DNA
<213> ORGANISM: Artificial Sequence
<220> FEATURE:
<223> OTHER INFORMATION: Primer

<400> SEQUENCE: 256
gccattggtt actggttgag ccac                                           24

<210> SEQ ID NO 257
<211> LENGTH: 24
<212> TYPE: DNA
<213> ORGANISM: Artificial Sequence
<220> FEATURE:
<223> OTHER INFORMATION: Primer

<400> SEQUENCE: 257
gatgtcgtga ccgcttaggc ttgg                                           24

```
<210> SEQ ID NO 258
<211> LENGTH: 23
<212> TYPE: DNA
<213> ORGANISM: Artificial Sequence
<220> FEATURE:
<223> OTHER INFORMATION: Primer

<400> SEQUENCE: 258
atagtgctgc taccagagaa ggc                                              23

<210> SEQ ID NO 259
<211> LENGTH: 32
<212> TYPE: DNA
<213> ORGANISM: Artificial Sequence
<220> FEATURE:
<223> OTHER INFORMATION: Primer

<400> SEQUENCE: 259
tcttgtcttg aatttttata gaacggcttg at                                    32

<210> SEQ ID NO 260
<211> LENGTH: 23
<212> TYPE: DNA
<213> ORGANISM: Artificial Sequence
<220> FEATURE:
<223> OTHER INFORMATION: Primer

<400> SEQUENCE: 260
cgccactcct tggacgaaat aag                                              23

<210> SEQ ID NO 261
<211> LENGTH: 23
<212> TYPE: DNA
<213> ORGANISM: Artificial Sequence
<220> FEATURE:
<223> OTHER INFORMATION: Primer

<400> SEQUENCE: 261
ttataacgca tgatagccgg ccc                                              23

<210> SEQ ID NO 262
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 262
agaagcaagg a                                                           11

<210> SEQ ID NO 263
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 263
agaaggaagg a                                                           11

<210> SEQ ID NO 264
<211> LENGTH: 11
<212> TYPE: DNA
<213> ORGANISM: Artificial Sequence
<220> FEATURE:
<223> OTHER INFORMATION: Mitochondrial DNA
```

<400> SEQUENCE: 264
aattcgactc t                                                        11

<210> SEQ ID NO 265
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 265
aattctactc t                                                        11

<210> SEQ ID NO 266
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 266
cgcttcgcct g                                                        11

<210> SEQ ID NO 267
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 267
cgctttgcct g                                                        11

<210> SEQ ID NO 268
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 268
tatagtggtt c                                                        11

<210> SEQ ID NO 269
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 269
tatagcggtt c                                                        11

<210> SEQ ID NO 270
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 270
cctgtaaact c                                                        11

<210> SEQ ID NO 271
<211> LENGTH: 11

```
<212> TYPE: DNA
<213> ORGANISM: Artificial Sequence
<220> FEATURE:
<223> OTHER INFORMATION: Mitochondrial DNA

<400> SEQUENCE: 271
cctgtgaact c                                                          11

<210> SEQ ID NO 272
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 272
ttaacttccc c                                                          11

<210> SEQ ID NO 273
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 273
ttaacctccc c                                                          11

<210> SEQ ID NO 274
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 274
aaagtattac c                                                          11

<210> SEQ ID NO 275
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 275
aaagtcttac c                                                          11

<210> SEQ ID NO 276
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 276 ggcctttctcg t                                                         11

<210> SEQ ID NO 277
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 277
```

```
ggcctcctcg t                                                    11

<210> SEQ ID NO 278
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 278
ccgtctaggt t                                                    11

<210> SEQ ID NO 279
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 279
ccgtcgaggt t                                                    11

<210> SEQ ID NO 280
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 280
acaaacaggc a                                                    11

<210> SEQ ID NO 281
<211> LENGTH: 11
<212> TYPE: DNA
<213> ORGANISM: Artificial Sequence
<220> FEATURE:
<223> OTHER INFORMATION: Mitochondrial DNA

<400> SEQUENCE: 281
acaaagaggc a                                                    11
```

INTERCELLULAR TRANSFER OF ORGANELLES IN PLANT SPECIES FOR CONFERRING CYTOPLASMIC MALE STERILITY

This application is a § 365 Application of PCT/US15/11033 filed Jan. 12, 2015 which claims the benefit of U.S. Provisional Application Nos. 61/926,315 and 62/021,599 filed Jan. 11, 2014 and Jul. 7, 2014 respectively. This application also claims priority to U.S. application Ser. No. 13/930,378 filed Jun. 28, 2013, which is a § 365 Application of PCT/US11/68153 filed Dec. 30, 2011, which claims the benefit of U.S. Provisional Application No. 61/428,672 filed Dec. 30, 2010, the entire disclosures of each of the aforementioned applications being incorporated herein by reference as though set forth in full.

FIELD OF THE INVENTION

The present invention relates to plant genetic engineering and particularly to methods for horizontal transfer of desirable traits in higher plants.

BACKGROUND OF THE INVENTION

Several publications and patent documents are cited throughout the specification in order to describe the state of the art to which this invention pertains. Each of these citations is incorporated herein by reference as though set forth in full.

Cells within a multicellular organism are connected by cytoplasmic bridges, which are termed plasmodesmata in plants (Lucas W J et al., 2009) and tunneling nanotubes in animals (Rustom A et al., 2004). Plasmodesmata were shown to actively and passively regulate intercellular trafficking of viral proteins, transcription factors, phloem proteins, mRNA and sRNA in plants (Lucas W J et al., 2009; Molnar A et al., 2010). An important recent development was the demonstration of the exchange of genetic material between cells in plant tissue grafts (Stegemann S & Bock R, 2009). However, there is no report yet on the intercellular movement of DNA-containing organelles, plastids and mitochondria, between plant cells.

During the past few years, supracellularity has emerged as a trait common to all life. Once thought to be a feature unique to plants, the physical continuity of cytoplasm and plasma membranes between neighboring cells has been observed in animal cells (Rustom A et al., 2004). These tunneling nanotubes were shown to be the conduits of active transport of organelles and cytoplasmic molecules between cells. Particularly relevant for this work, is the direct observation of transport of mitochondria through tunneling nanotubes in animal cells (Koyanagi M et al., 2005; Acquistapace A et al., 2011). Tunneling nanotubes and filopodia-like cytoplasmic bridges have also been observed linking unrelated bacterial cells and therefore may represent a universal mechanism for cellular communication and interdependence (Dubey G P & Ben-Yehuda S, 2011). Modulation of this process would represent an advance in the art in the creation of transplastomic plants.

Because male sterile maternal parental plants avoid the requirement for hand emasculation, such plants are highly desirable in hybrid seed production. Male sterility can either be caused by mitochondrial genes or by nuclear genes alone; the resulting conditions are known as cytoplasmic male sterility (CMS) and genetic male sterility (GMS), respectively. CMS is known to be associated with mitochondrial DNA sequences which have multiple rearrangements giving rise to chimeric mitochondrial genes. The CMS maternal parent is female fertile and produces hybrid seed upon pollination by the pollen of the paternal parent. Fertility of the CMS parent is restored when a restorer gene is incorporated in the nuclear genome. CMS-causing mitochondrial genes and nuclear restorer genes have been extensively reviewed in different crop systems (Carlsson et al., 2008; Chase, 2007; Chen and Liu, 2013; Gillman et al., 2009).

Cultivated tomato, *Solanum lycopersicum* (also known as *Lycopersicon esculentum* and/or *Lycopersicon lycopersicum*) is a crop in which no CMS has been described. One approach for obtaining useful forms of CMS in tomato included protoplast fusion for introduction of *Solanum acaule* or *Solanum tuberosum* mitochondria into tomato cells (EP 03663819 A1; Priority date Oct. 8, 1988). The process comprises the steps of (A) fusing tomato protoplasts that contain inactivated cytoplasmic elements with *Solanum* protoplasts that contain inactivated nuclear elements, to obtain a plurality of fusion products; and (B) regenerating at least one fusion product of said plurality into a whole, male-sterile tomato plant.

Transgenic induction of mitochondrial DNA rearrangements for CMS was described in tomato by the manipulation of the Msh1 nuclear gene that appears to be involved in the suppression of illegitimate recombination in plant mitochondria. Suppression of Msh1 expression by RNAi resulted in reproducible mitochondrial DNA rearrangement and a condition of male sterility (Sandhu et al., 2007).

When chloroplast DNA moves from cell to cell over the graft junction, sequencing of the plastid genome of graft transfer events confirmed the presence of a complete, unmodified incoming ptDNA in the new host. In contrast, the mitochondrial DNA in the graft transmission plants was chimeric, consisting of segments of *N. undulata* mtDNA (from CMS Partner 1) and fertile mitochondrial DNA (from *N. sylvestris*). The plant mitochondrial DNA is present in different size sub genomic circles formed by recombination via repeated sequences (Kubo and Newton, 2008; Logan, 2007; Sugiyama et al., 2005). In somatic cells there may be more mitochondria than mitochondrial genomes and the mitochondria may contain less than a complete mitochondrial genome (Preuten et al., 2010). Plant mitochondria are known to undergo cycles of fusion (Sheahan et al., 2005). Thus, fertility- or sterility-controlling mitochondrial DNA may move from cell to cell protected in intact organelles or as naked DNA.

Transformation of mitochondria with naked DNA has not yet been accomplished in higher plants (Niazi et al., 2013) and U.S. Pat. No. 5,530,191 (1996) entitled "Method for producing cytoplasmic male sterility in plants and use thereof in production of hybrid seed" describes production of CMS plants by the engineering of the chloroplast genome. The patent literature claims hybrid tomato, but the seed in these patents is always obtained by conventional crossing, involving manual removal of anthers and hand pollination. Claims of hybrid tomato patents focus on flavor enhancement (PCT/US2012/041478) or the benefits of seedless tomato obtained by using parthenocarpic genes (PCT/NL2000/000380; EP19990201787; EP2010000012146; US 20130189419).

SUMMARY OF THE INVENTION

In accordance with the present invention, a method for effecting intercellular transfer of organelles in plants for the creation of transgenic plants exhibiting desirable characteristics is provided. An exemplary method entails joining a root stock of a first plant and a scion from a second plant, said first and second plants comprising distinct plastid and nuclear genetic markers; culturing for a suitable period for grafting to occur; fragmenting or slicing the graft region and transferring said fragment or slices to a plant regeneration medium and selecting for cells expressing the nuclear and plastid genetic markers from said first and second plants. In one embodiment, the method entails decapitating the rootstock of a first plant, splitting the stem of said root stock and inserting a wedge shaped stem of scion from a second plant in the opening in the root stock, said first and second plants comprising distinct plastid and nuclear genetic markers; and culturing the graft plant for a suitable period for grafting to occur; then following the protocol above. The method can also comprise characterization of the size and type of DNA transferred. In a preferred embodiment, the organelle is a plastid and the method results in complete transfer of the plastid genome. In a particularly preferred aspect, the transferred plastid genome comprises at least one heterologous or endogenous DNA molecule expressing a protein of interest, e.g., a protein conferring herbicide or drought resistance. Other proteins of interest include without limitation, a fluorescent protein, an antibody, a cytokine, an interferon, a hormone, a selectable marker protein, a coagulation factor and/or an enzyme. Also provided are transgenic plants generated using the foregoing methods.

This invention provides a method for obtaining a plant cell of a multicellular plant, the mitochondria of which have acquired male sterility associated DNA sequences through a graft junction. These sequences are provided in FIG. 6. The method involves bringing two cells in contact such that they form cell to cell channels enabling movement of male sterility causing DNA sequences. The incoming, CMS-causing DNA may incorporate into the host's mitochondrial DNA by homologous recombination, or be maintained as an episomal element. The channel connections may conveniently be established by grafting the partners, one of which carries male-sterility causing DNA sequences and a second, fertile parent, the conversion of which into a male sterile form is desired. The nuclear genome of the fertile parent carries a nuclear marker gene facilitating the recovery of converted male sterile cells.

In one aspect, the creation of CMS plants entails certain steps in tissue culture. These include: (a) Marking the nucleus of the fertile partner with a marker gene via known methods of introducing heterologous sequences into recipient plants. The marker gene confers a selectable tissue culture phenotype, such as resistance to kanamycin or hygromycin, but any nuclear gene that is selectable in tissue culture can be used. (b) Marking the chloroplasts of the CMS plants with a selectable marker, such a resistance to spectinomycin, streptomycin, kanamycin, or chloramphenicol, again using methods known in the art. (c) Establishing contact between the fertile and CMS partners. The preferred embodiment involves a conventional wedge graft. However, alternative methods of establishing contact also results in cell-to-cell movement of mitochondrial DNA, such as wounding the Partners on their stems and tying them together at the wound site, or creating a chimeric tissue by mixing cells or protoplasts. (d) In a preferred embodiment, the wedge containing the graft junction is sliced and transferred in tissue culture to select for the nuclear marker of Partner 1 and chloroplast marker of Partner 2. (e) Regenerating plants from the double-resistant cells. (f) Transferring plants into the greenhouse to visually identify mitochondrial DNA transfer events by the change of flower morphology. (g) Repeatedly regenerating plants from the Graft Transmission tissue to accelerate sorting, and screening the plants by morphology in the greenhouse. (h) In cases where the CMS causing DNA sequence is known, plants can be screened by PCR for the CMS DNA.

An alternative tissue culture-independent method relies on morphological (pigment) traits encoded by nuclear genes (Partner 1) and visual (pigment or GFP) markers encoded by the plastid genome. Such visual markers have been useful to detect plastid marker excision in greenhouse-grown plants (Tungsuchat-Huang and Maliga, 2012; Tungsuchat-Huang et al., 2011). Graft transmission of CMS-causing mitochondrial DNA involves the following steps. (a) Graft Partner 1 (fertile, green) and Partner 2 (CMS mitochondria, visual plastid marker, such as aurea gene). (b) When the graft union has been successfully established, shoot regeneration can be forced from cells at the graft junction. This can most conveniently be achieved by decapitating the scion, so that the graft junction is at the tip of the plants. (c) Shoots developing from the graft area should be inspected for Partner 1 morphology and the presence of visual plastid marker from Partner 2. CMS flowers on branches developing in the graft region will indicate transfer of mitochondrial DNA. (d) In cases where the cytoplasmic male sterility causing DNA sequence is known, shoots can be screened by PCR for the CMS DNA. (e) When graft transmission of CMS-causing mitochondrial sequences is achieved, the visual chloroplast marker can be removed by recombinase-mediated marker excision using established protocols (Tungsuchat-Huang and Maliga, 2012; Tungsuchat-Huang and Maliga, 2014).

BRIEF DESCRIPTION OF THE DRAWINGS

(FIG. 1A) Plant regenerated from the GT-19C graft transmission event and the close-up picture of its (FIG. 1B) fertile flowers with anthers bearing pollen and (FIG. 1C) sterile flowers with anthers converted into petals. (FIG. 1D) Restoration of fertile flower anatomy facilitates identification of mitochondrial graft transmission event. *N. tabacum* Nt-CMS and fertile *N. sylvestris* Ns-F graft partners and GT19-C seed progeny. (FIG. 1E) Grafting tobacco in culture. The scion is Nt-CMS, which carries the nuclear gentamycin resistance marker; and the rootstock is Ns-F, which carries the plastid spectinomycin resistance (aadA) and aurea bar$^{au}$ genes. Arrow points to graft junction. (FIG. 1F) Selection of gentamycin and spectinomycin double-resistant clones. On right are stem slices from the graft region, on the left from above and below. Arrow points to double-resistant clone.

FIGS. 2A-2I: Flowers of graft partners *N. tabacum* Nt-CMS19G (P1) and *Nicotiana sylvestris* Ns137-CK2-2 (P2), and of the seed progeny obtained from fertile and CMS flowers of the GT-19 graft plastid transmission progeny. (FIG. 2A) One isolated anther from a wild type *N. tabacum* flower (above) and the anther after homeotic conversion of the *N. tabacum* alloplasmic substitution line (below). (FIG. 2B) Flower morphology of the graft partners and mixed flower anatomy on the GT19-C graft transmission plant. On the right flowers are shown with corolla, on the left with corolla removed. Note homeotic transformation of anthers into stigmatoid petals in Nt-CMS graft partner and the GT-CMS flowers. GT-F and *N. sylvestris* Ns-F flowers are fertile. The flowers of Nt-CMS graft partner and GT19-C plant (GT-CMS, GT-F) are pink, a nuclear trait; those of the *N. sylvestris* graft partner are white. A close-up of (FIG. 2C)

GT-CMS, (FIG. 2D) GT-intermediate and (FIG. 2E) GT-F flowers. (FIGS. 1A-2H) Scale bars in lower right corners are 10 mm. (FIGS. 2F-2H) Confirmation of plastid movement from fertile *N. sylvestris* (Ns-F) into CMS *N. tabacum* (Nt-CMS). (FIG. 2F) Partial map of the wild type *N. undulata* ptDNA in the CMS *N. tabacum* graft partner and the *N. sylvestris* ptDNA with the aadA spectinomycin resistance and aurea bar$^{au}$ transgenes. (FIG. 2G) DNA gel blots of graft partners and sterile graft transmission plants GT7, GT17 and a sterile and fertile branch of graft transmission plant GT19-C. BamHI digested total cellular DNA was probed with the rrn16, aadA and bar probes. (FIG. 2H) The complete *N. sylvestris* ptDNA is present in the GT19-C plants. Shown are identity plots of the plastid genomes of: Nt-CMS graft partner carrying *N. undulata* ptDNA (NC_016068) and graft transmission plant GT19-C (*N. sylvestris* pCK2-2 ptDNA). The mVISTA alignment was prepared using the *N. sylvestris* ptDNA (NC_007500) as reference with a 300-bp sliding window. (FIG. 2I) Nuclear SSR markers distinguishing *N. tabacum* and *N. sylvestris* chromosomes indicate that three plastid graft transfer plants have the complete *N. tabacum* nuclear genome. Shown are SSR markers distinguishing each of the 24 *N. tabacum* chromosomes from *N. sylvestris* chromosomes. Mw: 50 bp molecular-mass ladder; s: Ns-F graft partner; t: Nt-CMS graft partner; 7: GT7; 17: GT17; 19: GT19. White dots indicate the 200-bp fragment of the 50-bp molecular mass ladder.

FIGS. 3A-3D: The mitochondrial genome of GT-19 graft plastid transmission progeny is a chimera of the fertile *N. sylvestris* and CMS *N. undulata* mitochondrial genomes. Shown are the map positions of DNA polymorphic markers in the (FIG. 3A) *Nicotiana undulata*, (FIG. 3B) *Nicotiana sylvestris* and (FIG. 3C) GT-19 graft plastid transmission progeny on the *N. sylvestris* mtDNA map. (FIG. 3D) Recombinant GT19 mtDNA is composed of segments of CMS *N. undulata* and fertile *N. sylvestris* mtDNA. The origin of 24 markers in the GT19 mtDNA is shown on the *N. sylvestris* (KT997964) mtDNA map. *N. undulata* and *N. sylvestris* markers are in blue and red color, respectively. Note that markers 5 and 6 are located in repeat regions of the mitochondrial genome (Sugiyama Y et al., 2005). For polymorphic loci see Table S5.

FIGS. 4A-4D: The mitochondrial genome of the GT19C seed progeny is a mosaic of the two graft parents. (FIG. 4A and FIG. 4B) DNA sequence was obtained on the Illumina MiSeq platform, using 2×300 bp paired-end sequencing. The coverage of parental and recombinant mtDNAs was between 150-300 fold and 40-100-fold, respectively. Plotted is the fraction of *undulata* SNPs at every position in two recombinant fertile (Fert1, Fert2) and two recombinant CMS (Ster1, Ster2) mitochondrial genomes aligned with the parental *N. sylvestris* mtDNA. Alignment with the *N. undulata* mtDNA SNPs is shown on top. The SNPs from and sylv are on the top and the bottom in the recombinants, respectively. Black horizontal lines mark putative deletions in the *N. undulata* mtDNA. The positions of the mitochondrial repeats are marked as R1, R2 and R3. The general organization of the 430,597 nt *N. sylvestris* mitochondrial genome determined by us is the same as that of the *N. tabacum* mtDNA (Sugiyama et al., 2005) and the two genomes differ only at eight locations (6 SNPs and 2×1 nt indels). (FIG. 4C) As in FIG. 4A and FIG. 4B, parent-specific SNPs in two fertile and two CMS recombinants were aligned using the *N. sylvestris* mtDNA as reference. Red and blue dots identify *N. sylvestris*- and *N. undulata*-specific SNPs, respectively. The mitochondrial repeats are marked as R1, R2 and R3 and a blue bar marks the CMS-associated region between nucleotides 389,706-393,005. Here, deletions in the *N. undulata* mtDNA are identified by numbered black bars (Table S8). Gene maps were created using the Organellar Genome Draw program (Lohse M et al., 2013) based on the *N. sylvestris* mtDNA annotation (KT997964). (FIG. 4D) Homologous recombination between species-specific SNPs does not leave footprints at recombination junctions. Shown are mtDNA sequences at the species-specific SNPs in partner genomes and recombinants. Sequences between SNPs are identical in graft partners and recombinants. The provided sequences for the SNPs are: 3,573: SEQ ID NO: 262 (und, RF1, RF2, RS2) and SEQ ID NO: 263 (syl); 113,391: SEQ ID NO: 264 (und, RF1, RF2, RS3, RS4) and SEQ ID NO: 265 (syl); 124,966: SEQ ID NO: 266 (und, RF1, RF2, RS3, RS4) and SEQ ID NO: 267 (syl); 135,505: SEQ ID NO: 268 (und) and SEQ ID NO: 269 (syl, RF1, RF2, RS3, RS4); 395,427: SEQ ID NO: 270 (und, RF1, RF2, RS3, RS4) and SEQ ID NO: 271 (syl); 5,501: SEQ ID NO: 272 (und) and SEQ ID NO: 273 (syl, RF1, RF2, RS2); 114,285: SEQ ID NO: 274 (und) and SEQ ID NO: 275 (syl, RF1, RF2, RS3, RS4); 125,774: SEQ ID NO: 276 (und) and SEQ ID NO: 277 (syl, RF1, RF2, RS3, RS4); 135,740: SEQ ID NO: 278 (und, RF1, RF2, RS3, RS4) and SEQ ID NO: 279 (syl); 395,845: SEQ ID NO: 280 (und) and SEQ ID NO: 281 (syl, RF1, RF2, RS3, RS4).

FIG. 5A: Shown is the map of the mitochondrial DNA responsible for CMS in the CMS Graft Parent 1 *Nicotiana tabacum* CMS19G with *N. undulata* cytoplasm (und), the fertile Graft Parent 2 *Nicotiana sylvestris* CK2-2 (sylv), two recombinant fertile (R-fert1, R-fert2) and two recombinant CMS (R-ster1, R-ster2) mitochondrial genomes. The CMS region comprises (a) the 1567 nt atp1 gene, (b) a 1175 nt long region unique to CMS plants, and (c) a 3271 nt region that is homologous to the 389,686-393,200 nt region in the *N. tabacum* mtDNA (NC_006581). The und and sylv SNPs are shown in blue and red as individual markers, respectively, and as a continuous line for a fragment with several SNPs (68 markers in 3515 nt fragment). Note that the *N. undulata* mtDNA is rearranged relative to the *N. sylvestris* mtDNA. The maps were drawn to show the *N. undulata* mtDNA as continuous sequence. (FIG. 5B) Mitochondrial orf293 expression correlates with homeotic conversion of anthers and CMS. Shown are partial mtDNA maps of *N. sylvestris* (syl) fertile, *N. tabacum* (und) CMS, and two fertile (RF1, RF2) and two sterile (RS3, RS4) recombinant lines. SNPs derived from the *undulata* or *sylvestris* mitochondrial genomes are blue and red dots, respectively. 60 polymorphisms in the 3.5 kb *N. undulata* region on left are represented by solid blue line. (FIG. 5C) orf293 mRNA accumulates only in CMS plants. RNA gel blots were hybridized with orf293 (P3) and atp1 (P4) probes. Data are shown for the two graft partners and second and third generation seed progeny of GT19-C marked by adding one more digits for each generation separated by a hyphen, such as Nt(RF2) for the 1$^{st}$ generation, Nt(RF2-1) for 2$^{nd}$ and Nt(RF2-2-1) for 3$^{rd}$ generation. (FIG. 5D) Expression of the atp1 and orf293 genes in mitochondria. Top-Partial maps of *N. sylvestris* (syl) fertile, *N. tabacum* (und) CMS and *N. undulata* (und) fertile mitochondrial genomes. Note that orf102 and atp1 genes are not on adjacent regions in the *N. sylvestris* fertile mtDNA. P1 to P6 indicate the position of probes. Bottom-Orf293 mRNA accumulates only in CMS plants. Note that the size of atp1 mRNA is slightly larger in the *N. undulata* mitochondria than in the *N. tabacum* cytoplasmic substitution line.

FIGS. 6A-6B: DNA sequence of CMS encoding DNA region in the *N. undulata* mitochondrial genome (FIG. 6A; SEQ ID NO: 1) and cognate regions in fertile mitochondria (FIG. 6B; SEQ ID NO: 2, FIG. 6C; SEQ ID NO: 3), as marked in FIG. 5A.

FIG. 7: Alignment of the *N. undulata* (und; SEQ ID NO: 4) and *N. sylvestris* (sylv; SEQ ID NO: 5) ORF102 sequences. Note four mismatches.

(FIG. 8A) Partner P1 is *N. tabacum* (2N=48) with a nuclear gentamycin resistance transgene and wild-type *N. tabacum* plastids and mitochondria. Partner P2 has a wild-type *N. sylvestris* (2N=24) nuclear genome, *N. undulata* plastids with aadA transgenes for spectinomycin selection and the aurea young leaf color phenotype ($bar^{au}$ gene) and *N. undulata* mitochondria that confer cytoplasmic male sterility (CMS-92). Shown is also the G1 plant and its markers. Black bar=10 cm (FIG. 8B) Flower morphology of the P1 and P2 partners and G1 PGT plant. White bar=1 cm (FIG. 9A) Grafted plant. Note that the P2 scion shown here is green because the expression of the $bar^{au}$ gene is restricted to fast growing tissue and is sensitive to environmental conditions. (FIG. 9B) Selection in cultures of one- to two-mm graft sections for gentamycin- and spectinomycin-resistance. On the left are stem sections from above (P2) and below (P1) the graft and on the right from the graft region. Note a green, proliferating callus that yielded the G4 PGT plants.

FIGS. 11A-11C: Identification of the source of mtDNA in the PGT plants. (FIG. 11A) Schematic representation of the tobacco mtDNA master circle with the position of polymorphic regions marked. Repeated regions are marked with boxes. (FIG. 11B) Mitochondrial DNA sequence polymorphisms. The provided sequences (from top to bottom) at the indicated genes are: orf125a: SEQ ID NO: 150, SEQ ID NO: 151, SEQ ID NO: 150, SEQ ID NO: 152, SEQ ID NO: 153, SEQ ID NO: 152; orf129b: SEQ ID NO: 154, SEQ ID NO: 155, SEQ ID NO: 154, SEQ ID NO: 156, SEQ ID NO: 157, SEQ ID NO: 156, SEQ ID NO: 158, SEQ ID NO: 159, SEQ ID NO: 158; nad4 intron: SEQ ID NO: 160, SEQ ID NO: 161, SEQ ID NO: 160; nad2 intron: SEQ ID NO: 162, SEQ ID NO: 163, SEQ ID NO: 162; nad5 intron: SEQ ID NO: 164, SEQ ID NO: 165, SEQ ID NO: 164; orf115-ccmFc spacer: SEQ ID NO: 166, SEQ ID NO: 167, SEQ ID NO: 166, SEQ ID NO: 168, SEQ ID NO: 169, SEQ ID NO: 168. (FIG. 11C) Map position of polymorphic sites relative to the sequencing primers and gene features.

FIGS. 12A-12C: Identification of the *N. undulata* plastids in the PGT plants. (FIG. 12A) Identity plots of the plastid genomes of the transplastomic P2 partner carrying *N. undulata* ptDNA (u) with the aadA and $bar^{au}$ transgenes (JN563930), the G1, G3, G4 (G) PGT plants and the P1 partner with *N. tabacum* ptDNA (t; Z00044) aligned with the mVISTA program using a 500-bp sliding window. Above the map are shown the positions of the DNA probes (#1 through #6) and DNA polymorphisms (*1 through *7). (FIG. 12B) Plastid DNA sequence polymorphisms. For map position see FIG. 12A. The provided sequences (from top to bottom) at the indicated genes are: atpF intron: SEQ ID NO: 170, SEQ ID NO: 171, SEQ ID NO: 171; rpoB-trnC spacer: SEQ ID NO: 172, SEQ ID NO: 173, SEQ ID NO: 173; trnL intron: SEQ ID NO: 174, SEQ ID NO: 175, SEQ ID NO: 175; accD: SEQ ID NO: 176, SEQ ID NO: 177, SEQ ID NO: 177; rpl16-rps3 spacer: SEQ ID NO: 178, SEQ ID NO: 179, SEQ ID NO: 179; ndhF: SEQ ID NO: 180, SEQ ID NO: 181, SEQ ID NO: 181; ndhE-ndhG spacer: SEQ ID NO: 182, SEQ ID NO: 183, SEQ ID NO: 183. (FIG. 12C) DNA gel blot to identify RFLP markers in ptDNA. For probes see FIG. 12A.

(FIG. 13A) Cells at graft junction reconnect by plasmodesmata. Arrows point to sites where opposite parts of the contact walls are synchronously thinned (Ehlers K & Kollmann R, 2001). These are future sites of plasmodesmata. Proplastids (ovals), mitochondria (small circles) and nuclei (large circles) are identified in scion and rootstock. N.s., *N. sylvestris*; N.t., *N. tabacum*, N.u., *N. undulata*; CMS, cytoplasmic male sterile. (FIG. 13B) Proplastid is transferred via initial cytoplasmic connection. (FIG. 13C) Transferred spectinomycin resistant plastid takes over on selective medium. Note that the cells derive from the bottom cell in FIG. 13B.

DETAILED DESCRIPTION OF THE INVENTION

Figure 1A:
FIGS. 1A-1F: Graft transmission of mitochondrial DNA alters flower morphology.

Crossing suitable maternal and paternal genetic lines yields hybrid seed of crops that favorably combine the properties of the two parents. Production of hybrid seed is labor intensive, in situations where manual removal of anthers from the maternal flowers, i.e., hand emasculation, is required to prevent self-pollination. Genetic male sterility of the maternal parent eliminates the need for hand emasculation. The present invention provides a practical means for transfer of cytoplasmic male sterility (CMS) traits by graft transfer of mitochondrial DNA, when said mitochondrial DNA encodes sequences that confer male sterility to the flowers of the recipient plant. If a cognate fertility restorer gene is transformed into the nucleus of the pollen parent, the cross yields fertile hybrids. The example described in the present invention is creation of CMS in tomato by graft transfer of mitochondrial DNA from petunia. An alternative source of male-sterility causing mitochondrial DNA is male sterile tobacco. Tomato, petunia and tobacco are sexually incompatible. Thus, cell-to-cell movement of mitochondrial DNA, followed by recombination between the incoming and resident mitochondrial DNAs gives rise to CMS without the transfer of nuclear genetic information. The protocol can be applied to any graft-compatible species when the mitochondrion of one of the graft partners encodes a male sterility-causing gene.

We report cell-to-cell movement of mitochondria through a graft junction. Mitochondrial movement was discovered in an experiment designed to select for chloroplast transfer from *Nicotiana sylvestris* into *N. tabacum* cells. The alloplasmic *N. tabacum* line we used carries *N. undulata* cytoplasmic genomes, and its flowers are male sterile due to the foreign mitochondrial genome. Thus, rare mitochondrial DNA transfer from *N. sylvestris* to *N. tabacum* could be recognized by restoration of fertile flower anatomy. Analyses of the mitochondrial genomes revealed extensive recombination, tentatively linking male sterility to orf293, a mitochondrial gene causing homeotic conversion of anthers into petals. Demonstrating cell-to-cell movement of mitochondria reconstructs the evolutionary process of horizontal mitochondrial DNA transfer and enables modification of the mitochondrial genome by DNA transmitted from a sexually incompatible species. Conversion of anthers into petals is a visual marker that can be useful for mitochondrial transformation.

I. General Methods for Constructing Plastid-Transgenic CMS Systems and for Production of Hybrid Seed The transgenic CMS systems of the invention are prepared and used according to the general methods set forth below for nuclear and plastid transformation of higher plants, maintenance of parental plant lines and production of hybrid seed.

A. DNA Constructs and Methods for Stably Transforming Plastids with Selectable Marker Genes and Regenerating Plastid-Transgenic Plants Methods and DNA constructs for stable, high-efficiency transformation of plastids and expression of recombinant proteins in plastids are known in the art. The methods and constructs described in the following references are preferred for practice of the present invention: Svab et al., Proc. Natl. Acad. Sci. USA, 87:8526-30 (1990); Svab & Maliga, Proc. Natl. Acad. Sci. USA, 90: 913-17 (1993); Carrer et al., Mol. Gen. Genet., 241:49-56 (1993); Staub & Maliga, EMBO J., 12: 601-06 (1993); and U.S. Pat. Nos. 5,877,402, 6,138,168 and 7,667,093. All the aforementioned disclosures describe suitable methods for stable, high-efficiency plastid transformation and expression of recombinant genes in plastids.

The following definitions will facilitate the understanding of the methods used in accordance with the present invention:

"Heteroplastomic" refers to the presence of a mixed population of different plastid or mitochondrial genomes within a single plastid or mitochondrion in a population of plastids or mitochondria contained in plant cells or tissues.

"Homoplastomic" refers to a pure population of plastid genomes, either within a plastid or within a population contained in plant cells and tissues. Homoplastomic plastids, cells or tissues are genetically stable because they contain only one type of plastid genome. Hence, they remain homoplastomic even after the selection pressure has been removed, and selfed progeny are also homoplastomic. For purposes of the present invention, heteroplastomic populations of genomes that are functionally homoplastomic (i.e., contain only minor populations of wild-type DNA or transformed genomes with sequence variations) may be referred to herein as "functionally homoplastomic" or "substantially homoplastomic." These types of cells or tissues can be readily purified to a homoplastomic state by continued selection.

"Plastome" refers to the genome of a plastid.

"Transplastome" refers to a transformed plastid genome.

"Alloplasmid substitution line" refers to plants in which the cytoplasm (chloroplasts and mitochondria) have been replaced by the cytoplasm of a different species (or of a genetic line). For example, an alloplasmic *N. tabacum* may be obtained by repeated pollination of *Nicotiana undulata* with *Nicotiana tabacum*, pollen resulting in the replacement of *N. undulata* chromosomes with *N. tabacum* chromosomes.

"Transformation of plastids" refers to stable integration of transforming DNA into the plastid genome that is transmitted to the seed progeny of plants containing the transformed plastids.

"Transforming DNA" refers to homologous DNA, or heterologous DNA flanked by homologous DNA, which when introduced into plastids becomes part of the plastid genome by homologous recombination.

The terms "selective marker" or "selectable marker" refer to a phenotype that identifies a successfully transformed organelle, cell or tissue, when a gene or allele encoding the selective marker is included in the foreign DNA used for transformation. Commonly used selective markers include resistance to antibiotics, herbicides or other compounds, which would be lethal to cells, organelles or tissues not expressing the resistance gene or allele. Selection of transformants is accomplished by growing the cells or tissues under selective pressure, i.e., on media containing the antibiotic, herbicide or other compound. Selectable marker genes may also confer resistance to a selection agent in tissue culture and/or confer a phenotype which is identifiable upon visual inspection. Thus, in one embodiment the selectable marker gene can act as both the selection agent and the agent which enables visual identification of cells comprising transformed plastids. In an alternative embodiment, the selectable marker encoding nucleic acid comprises two sequences, one encoding a molecule that renders cells resistant to a selection agent in tissue culture and another that enables visual identification of cells comprising transformed plastids. If the selective marker is a "lethal" selective marker, cells which express the selective marker will live, while cells lacking the selective marker will die. If the selective marker is "non-lethal", transformants (i.e., cells expressing the selective marker) will be identifiable by some means from non-transformants, but both transformants and non-transformants will live in the presence of the selection pressure.

Several methods are available to introduce DNA into the plastids of flowering plants, including, but not limited to, *Agrobacterium* vectors, polyethylene glycol (PEG) treatment of protoplasts, bombardment of cells or tissues with microprojectiles coated with the plastid-transforming DNA (sometimes referred to herein as "biolistic DNA delivery") and temporary holes cut by a UV laser microbeam. Other methods include use calcium phosphate treatment of protoplasts, electroporation of isolated protoplasts and agitation of cell suspensions with microbeads coated with the transforming DNA. The biolistic method, as described by Svab & Maliga, 1993, supra is preferred for plastid transformation because it can be used on a wide variety of plants and tissues. In an alternative embodiment, useful in plant systems where protoplasts may be obtained and regenerated into intact plants, plastid transformation may be achieved by polyethylene glycol (PEG) treatment of protoplasts in the presence of the transforming DNA. Methods for stable plastid transformation in PEG-treated protoplasts are exemplified in tobacco by Golds et al., Bio/Technology, 11: 95-97 (1993).

The term "tomato" or "tomato plant" means any variety, cultivar, or population of *Solanum lycopersicum* (*Lycopersicon esculentum* and/or *Lycopersicon lycopersicum*), including both commercial tomato plants as well as heirloom varieties. In some embodiments, "tomato" may also include wild tomato species, such as, but not limited to, *Solanum lycopersicum* var. *cerasiforme, Solanum pimpinellifolium, Solanum cheesmaniae, Solanum neorickii, Solanum chmielewskii, Solanum habrochaites, Solanum pennellii, Solanum peruvianum, Solanum chilense* and *Solanum lycopersicoides*.

As used herein, the term "plant" includes plant cells, plant protoplasts, plant cell tissue cultures from which tomato plants can be regenerated, plant calli, plant cell clumps, and plant cells that are intact in plants, or parts of plants, such as embryos, pollen, ovules, flowers, leaves, seeds, roots, root tips and the like. The term "tomato fruit" refers to the fruit produced by a tomato plant, including the flesh, pulp, meat, and seeds of the fruit.

As used herein, the term "variety" or "cultivar" means a group of similar plants within a species that, by structural features, genetic traits, performance, and/or content of volatile compounds, sugars, and/or acids, can be identified from other varieties/cultivars within the same species.

The method described is not restricted to creating CMS in tomato, because cell-to-cell movement of sterility causing DNA can be used to convert any fertile plant into a CMS form. Such male-sterility causing mitochondrial genes have been described in a number of species, including without limitation, brassica, carrot, common bean, maize, pepper, petunia, radish, rice, sorghum, sugar beet, sunflower, tobacco, and wheat (Carlsson et al., 2008; Chen and Liu, 2013).

A "plant sector" refers to a region or a full leaf of a plant that is visually identifiable due to expression of a selectable marker gene or the excision of a selectable marker gene in accordance with the present invention.

"Operably linked" refers to two different regions or two separate genes spliced together in a construct such that both regions will function to promote gene expression and/or protein translation.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

A "replicon" is any genetic element, for example, a plasmid, cosmid; bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence.

All amino-acid residue sequences represented herein conform to the conventional left-to-right amino-terminus to carboxy-terminus orientation.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion, biolistic bombardment and the like.

A "clone" or "clonal cell population" is a population of cells derived from a single cell or common ancestor by mitosis.

A "cell line" is a clone of a primary cell or cell population that is capable of stable growth in vitro for many generations.

"Agroinfiltration" refers to *Agrobacterium* mediated T-DNA transfer. Specifically, this process involves vacuum treatment of leaf segments in an *Agrobacterium* suspension and a subsequent release of vacuum, which facilitates entry of bacterium cells into the inter-cellular space.

"T-DNA" refers to the transferred-region of the Ti (tumor-inducing) plasmid of *Agrobacterium tumefaciens*. Ti plasmids are natural gene transfer systems for the introduction of heterologous nucleic acids into the nucleus of higher plants.

The terms "percent similarity", "percent identity" and "percent homology" when referring to a particular sequence are used as set forth in the University of Wisconsin GCG software program.

The materials and methods set forth below are provided to facilitate practice of the present invention.

Materials and Methods

The graft partners were Nt-CMS (Nt-CMS92), a *Nicotiana tabacum* cv. Petit Havana line (Maliga P & Svab Z, 2011) that carries the cytoplasm of *N. undulata* and was transformed with *Agrobacterium* binary vector pPZP221 (Hajdukiewicz P, 1994) yielding gentamycin resistant line Nt-G115; and Ns-F, a fertile *Nicotiana sylvestris* line, the plastids of which have been transformed with plasmid pCK2 (Ns-pCK2-2) encoding a selectable spectinomycin resistance (aadA) and the visual bar$^{au}$ genes (Maliga P & Svab Z, 2011). Seeds of *Nicotiana undulata* TW145 (PI 306637), TW146 (PI 555575) and TW147 (PI 306637) were obtained from the USDA ARS National Plant Germplasm System. Grafting and selection of graft plastid transmission events was carried out as described (Thyssen G et al., 2012). Total cellular DNA was isolated using the CTAB method (Murray M G & Thompson W F, 1980). The SSR markers were adopted from Thyssen G et al. (2012), originally described in Moon H S et al. (2008) and listed in Table S4. Location of the SSR markers on the *N. tabacum* chromosomes is described in Bindler G et al. (2011). The PCR program: 94° C. for 5 min; 37 cycles of 94° C. for 45 sec, 59° C. for 45 sec, 72° C. for 1 min; 72° C. for 10 min was used for all but chromosomes 8, 12, 14, 16. For chromosomes 8, 12, 14, 16 the PCR program 94° C. for 5 min; 37 cycles of 94° C. for 20 sec, 54° C. for 20 sec, 72° C. for 1 min; 72° C. for 10 min was used. The PCR products were ran on a 2.5% TAE agarose gel for chromosomes 8, 14, 16, 17, 18, 20, and on a 5% MetaPhor Agarose (Lonza, Rockland, Me.) gel for chromosomes 1, 2, 3, 4, 5, 6, 7, 9, 10, 11, 12, 13, 15, 19, 21, 22, 23, 24. For restriction fragment analyses of ptDNA, CTAB purified (Murray M G & Thompson W F, 1980) total cellular DNA was digested with the BamHI restriction enzyme and probed with rrn16, aadA and bar probes (Kittiwongwattana C et al., 2007). To determine organelle genome sequences, NGS was performed in the Waksman Genomic Core Facility. Briefly, CTAB purified total cellular DNA (Murray M G & Thompson W F, 1980) was physically sheared with the Covaris system (Covaris, Woburn, Mass.) following the manufacturer's protocol. Sequencing libraries were prepared using standard TruSeq DNA Library Preparation Kit (Illumina, San Diego, Calif., USA) according to the manufacturer's protocol. Libraries were size-selected at 650 bp with the Egel Agrose Electrophoresis System (Thermo Fisher Scientific), and quantified using the Qubit dsDNA HS (High Sensitivity) kit (Thermo Fisher Scientific, Foster City, Calif., USA). Finally, libraries were evaluated for fragment size using the Bioanalyzer (Agilent Technologies, Santa Clara, Calif., USA). Library normalization and sequencing was performed according to the manufacturer's recommendations with MiSeq v3 (2×300 bp) chemistries. Adapters and barcodes were trimmed per the default setting in the Illumina Experiment Manager (v1.8). BWA-MEM algorithm using default settings (Li H & Durbin R, 2009) was used to map adapter-free quality trimmed reads from four GT19-C offspring, recombinant fertile RF1, RF2, and recombinant sterile RS3 and RS4, to the *Nicotiana sylvestris* ptDNA (NC_006500). Mapped reads were used to create de novo contigs using the ABySS program, using the paired-end (abyss-pe) option with a k-mer of 90 (Simpson J T et al., 2009). NC_006500 was used as a guide to map and orient contigs in SeqMan Pro (DNASTAR Inc., Madison, Wis.) to obtain the complete ptDNA sequence. The plastid DNA sequence of the four GT19-C offspring was identical. The mVISTA alignment in FIG. 2H (Frazer K A, 2004) was prepared using the *N. sylvestris* ptDNA (NC_007500) as reference with a 300-bp sliding window. For mtDNA mapping and contig assembly, adapter free, quality trimmed reads were mapped to the *Nicotiana tabacum* mtDNA (NC_006581), *Hyosciamus niger* (KM207685) and two *Capsicum annuum* cultivar (NC_024624, KJ865409) mtDNAs using the BWA-MEM algorithm and default settings (Li H & Durbin R, 2009). All mapped reads and their pairs were used to create de novo contigs with the ABySS program v1.9 using the paired-end (abyss-pe) option with a k-mer of 96 (Simpson J T et al., 2009). *N. undulata* mitochondrial SNPs were called by the GATK Haplotype-Caller program (Van der Auwera G A et al., 2013; DePristo M A et al., 2011; McKenna A et al., 2010) using the BAM file obtained from BWA mapping with default parameters. SNPs and indels called by GATK were filtered keeping only SNPs with ≥80% SNP ratio and a minimum of 30× coverage in *N. undulata*. The origin of regions in the seed progeny was assigned by SNPs in the de novo contigs. Total cellular RNA was isolated from leaves of greenhouse-grown plants using TRIzol (Invitrogen, Carlsbad, Calif.) and dissolved in 20 µl DEPC water. The isolated RNA was precipitated by adding 2 µl 3M sodium acetate (pH 5.2) and 66 µl 100% ethanol (1 h at −20° C.). RNA was sedimented by centrifugation, washed with 75% ethanol, air dried and dissolved in 22 µl DEPC water. 3 µg RNA was electrophoresed on 1.5% agarose/formaldehyde gel (6% of 37 w/v % formaldehyde) in MOPS buffer (Green M & Sambrook J, 2012). RNA was transferred to Amersham Hybond-N membranes (GE Healthcare Ltd, Little Chalfont, UK) using capillary transfer. Probes were PCR fragments amplified using total cellular DNA as template using primers listed in Table S7. Probing was carried out as described (Gurdon C & Maliga P, 2014).

The following examples are provided to illustrate certain embodiments of the invention. They are not intended to limit the invention in any way.

EXAMPLES

We describe here a novel approach for generating CMS tomato plants by the graft transmission of male-sterility causing mitochondrial DNA sequences from graft compatible solanaceous species, such as tobacco or petunia. The method is based on co-transmission of chloroplasts and mitochondria through a graft junction, normally without the transfer of any nuclear (chromosomal) genetic information. If nuclear DNA from the CMS parent is transferred, it can be removed by repeated pollination with the fertile partner. The feasibility of the approach was shown by (a) marking the nucleus of a *Nicotiana tabacum* plant with a transgenic kanamycin or hygromycin resistance gene; (b) transforming the chloroplasts of a second species, *Nicotiana sylvestris*, with a selectable spectinomycin resistance gene; (c) grafting one species as the rootstock and the second species as scion, so that the organellar DNA (organelles) can traverse through the graft junction; (d) slicing up the graft junction and selecting in tissue culture for the nucleus of *N. tabacum* by the kanamycin or hygromycin resistance gene and the chloroplasts of *N. sylvestris* by spectinomycin resistance; (e) regenerating plants from the double-resistant cells and (f) and transferring the regenerated plants to the greenhouse to identify the CMS plants by flower morphology. The CMS in the plants is due to partial or full substitution of *N. tabacum* or *N. sylvestris* mitochondria with the *Nicotiana undulata* mitochondria, that causes homeotic transformation of anthers into petals or stigma-like structures.

In Experiment 1, when chloroplast graft transmission events were selected grafting fertile *N. tabacum* (Graft Partner 1) onto CMS *N. sylvestris* carrying spectinomycin resistant plastids (Graft Partner 2), no co-transfer of chloroplasts and mitochondrial DNA was apparent (Thyssen et al., 2012). However, in Experiment 2, when graft transmission of chloroplasts was studied grafting CMS *N. tabacum* (Graft Partner 1; gentamycin resistant Nt-CMS92G) and fertile *N. sylvestris* (Graft Partner 2; spectinomycin resistant chloroplasts; Ns137-CK2-2 fertile plant), co-transfer of mitochondria with the selected chloroplasts was readily obvious by the appearance of male fertile flowers in one of the three regenerated plants of event GT19-1C. No co-transmission of mitochondria with chloroplasts was found in two other events in Experiment 2. Co-transfer of chloroplasts and mitochondria must have occurred at some frequency in both experiments. We surmise that detection of the transfer of male fertility-encoding DNA was facilitated by the dominant nature of male fertility over CMS in Experiment 2.

Example 1

CMS Tomato by Graft Transmission of Tobacco CMS92 Mitochondrial DNA

Graft transmission of tobacco CMS92 mitochondrial DNA into tomato can be accomplished via performance of the following steps.
(1) Transform the tomato nucleus with a selectable gentamycin or kanamycin resistance gene. *Agrobacterium* binary vectors with a number of different marker genes have been described, including those conferring resistance to gentamycin and kanamycin (Hajdukiewicz et al., 1994; Miki and McHugh, 2004). A suitable tissue-culture responsive tomato cultivar, such as IPA64 (Ruf et al., 2001) can be used for this purpose, but other cultivars are available, such as Dorothy's Green and Green Pineapple (Ruf and Bock, 2014).
(2) Create a tobacco plastid genome that is compatible with the tomato nuclear background in the tobacco CMS92 background *N. tabacum* or *N. undulata* plastids and the CMS sequence from *N. undulata* in the mitochondrial genome). This can be achieved by converting codon 264 of the atpA gene from Pro (cCc) to Leu (cUc) in a CMS92 plant. It is known that *Atropa belladonna* (nightshade), a related solanaceous species, has no capacity to edit the tobacco atpA gene. The tobacco plastid genome, when introduced into the *Atropa* nuclear background, yielded pigment deficient plants. Mutation of the cCc codon to cUc restored normal greening (Schmitz-Linneweber et al., 2005). Tomato, as *Atropa*, has a T nucleotide at the critical position in the atpA gene, thus it is unlikely to have a capacity to edit the tobacco atpA site (Kahlau et al., 2006). The problem can be pre-empted by replacing the Pro codon with a Leu codon using standard plastid engineering methods. The point mutation can be introduced into the atpA by making the mutant atpA gene part of the vector targeting sequence, and screening for the incorporation of the mutation in the transformed chloroplasts (Kanevski et al., 1999; Sinagawa-Garcia et al., 2009). A second tobacco codon that needs to be pre-edited is rps14 codon 50 (Kahlau et al., 2006). As part of step 2, the spectinomycin resistance (aadA) gene is introduced into the plastid genome. Incorporation of target sites for site-specific recombinases to flank aadA facilitates post-transformation excision of the marker gene.
(3) Graft IPA64-G (gentamycin resistant) plants and the engineered Nt-CMS-92 (carrying a spectinomycin resistance gene in its chloroplast genome).
(4) Slice up the graft junction and select for the transfer of CMS92 chloroplasts on gentamycin and spectinomycin medium.
(5) Regenerate plants from double-resistant tissue, and inspect the flowers for homeotic transformation. Analyze mitochondrial DNA to identify recombination events. This may be by PCR amplification and sequencing of polymorphic regions, DNA gel blot (Southern) analyses of polymorphic regions or sequencing entire mitochondrial genomes to detect SNPs and insertions and deletions in the mitochondrial genome.
(6) Repeat the plant regeneration multiple times to accelerate sorting of mitochondrial DNA.

As an alternative to tobacco chloroplasts for the co-transfer of CMS-causing mitochondrial DNA, we may construct an intermediate source of CMS (the bridge plant) by transferring the tomato chloroplasts into the tobacco CMS92 background. The rationale is that, if the requirement for editing is eliminated by a mutation at the DNA level, the requirement for editing is no longer there. Thus, the tomato plastid genome should be fully compatible with the CMS92 tobacco background. Accordingly, as an alternative to Step 2 above, plastids may be transformed in tomato with the aadA gene, then transferred by graft transmission into the tobacco CMS92 background where they will be combined with the tobacco CMS gene. The tobacco CMS mitochondrial sequence can subsequently be introduced by graft transmission into tomato. When the desired tomato line is obtained, the aadA gene can be removed by site-specific recombinases, as described (Kittiwongwattana et al., 2007; Lutz and Maliga, 2007; Lutz et al., 2006). The advantage of using tobacco bridge plants is protection against any unknown form of plastid-nucleus incompatibility that may be encoded in the tobacco ptDNA in the final product, the CMS tomato, which will have its native, unmodified chloroplast genome and minimal input of the tobacco mitochondrial DNA, preferably restricted to the CMS-causing sequence.

The CMS tomato plants will be male sterile due to the homeotic transformation of anthers, but female fertile. The CMS tomato plants can be propagated by pollination with any fertile tomato that will serve as the maintainer line. Repeated pollination with different maintainer lines will yield isogenic pairs of CMS and fertile lines.

Hybrid seed can be obtained by pollination with a suitable pollen parent. In the absence of pollen, the hybrid plants normally will not set seed. However, in tomato, seedless fruits develop if parthenocarpic genes are incorporated in the genetic lines (Gorguet et al., 2005; Medina et al., 2013). If restoration of male sterility is required, the restorer gene can be isolated from *N. undulata* by standard molecular biology techniques and transformed into the nucleus of tomato to be used as a fertility restorer line.

Cultivated tomato and related wild species can be crossed. Thus, it may be advantageous to transfer the CMS92 male sterility gene first into a related wild species with good tissue culture regeneration potential, and then subsequently introduce the mitochondrial CMS trait with the engineered chloroplasts by graft transmission into cultivated tomato. Wild species with shooting response in tissue culture are *L. chilense, L. peruvianum* var. *humifusum, L. esculentum* x *L. peruvianum, L. esculentum* cv. MsK, *L. hirsutum* f. *hirsutum* (Peres et al., 2001).

Plastid Graft Transmission Events

Figure 1B:
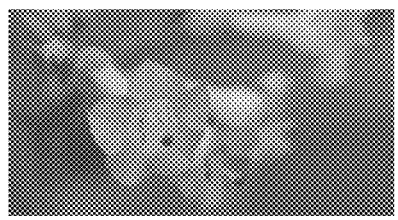
Figure 1C:
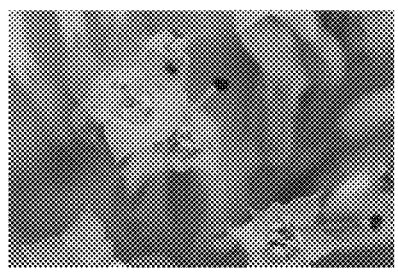
Figure 1D:
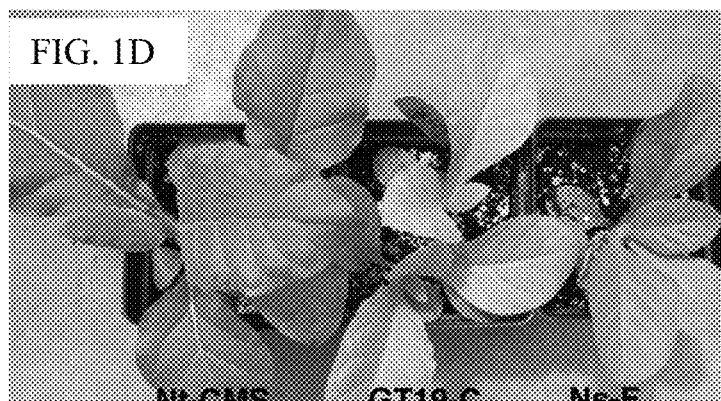
Figure 1E:
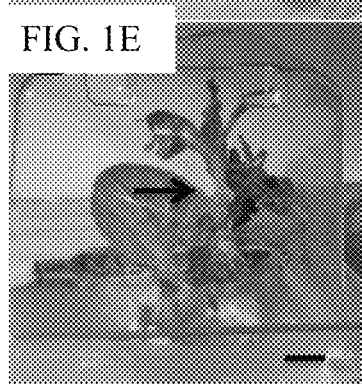
Figure 1F:
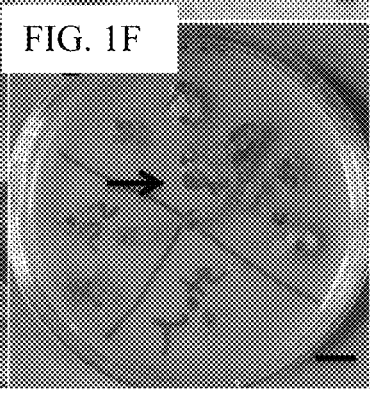
Figure 2F:
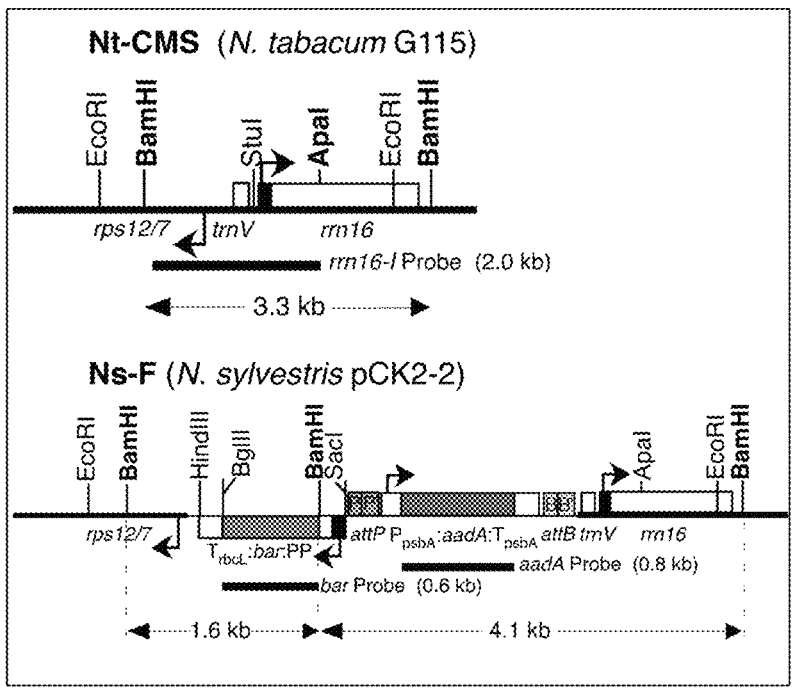
Figure 2G:
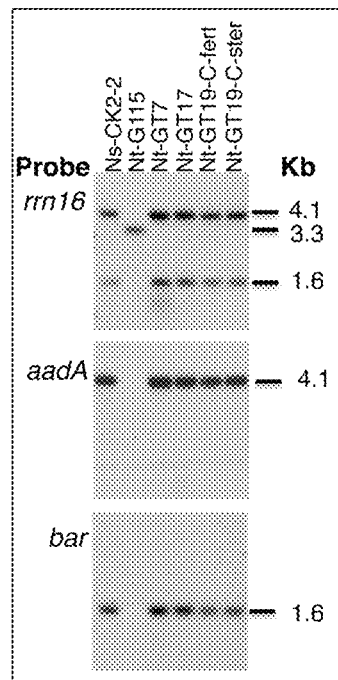
Figure 2H:
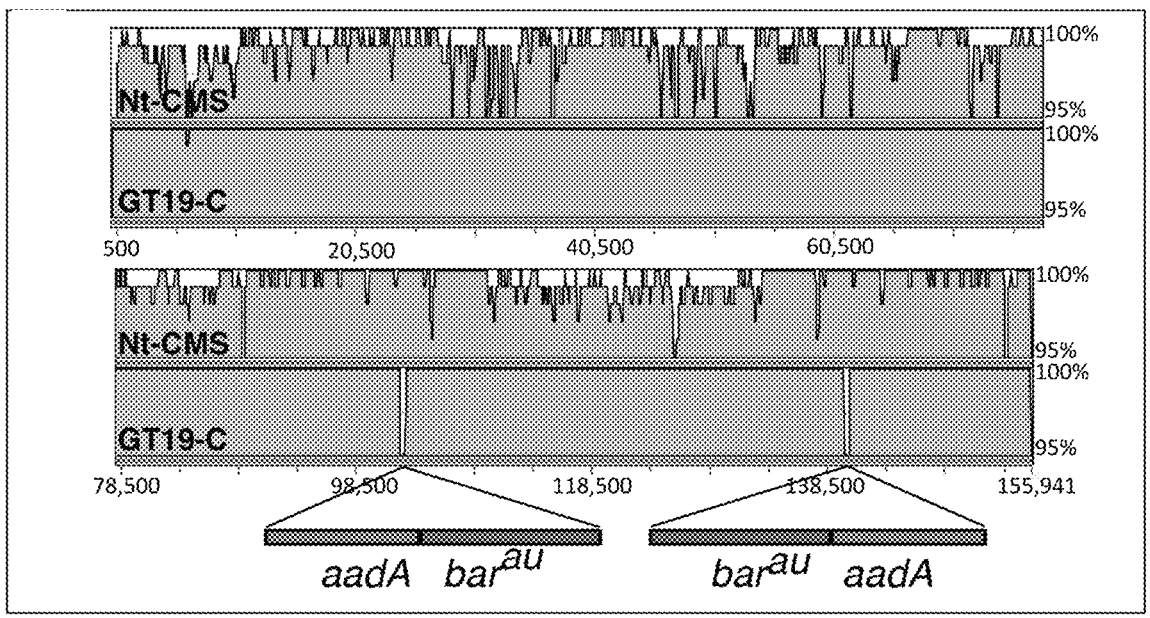
Figure 2I:
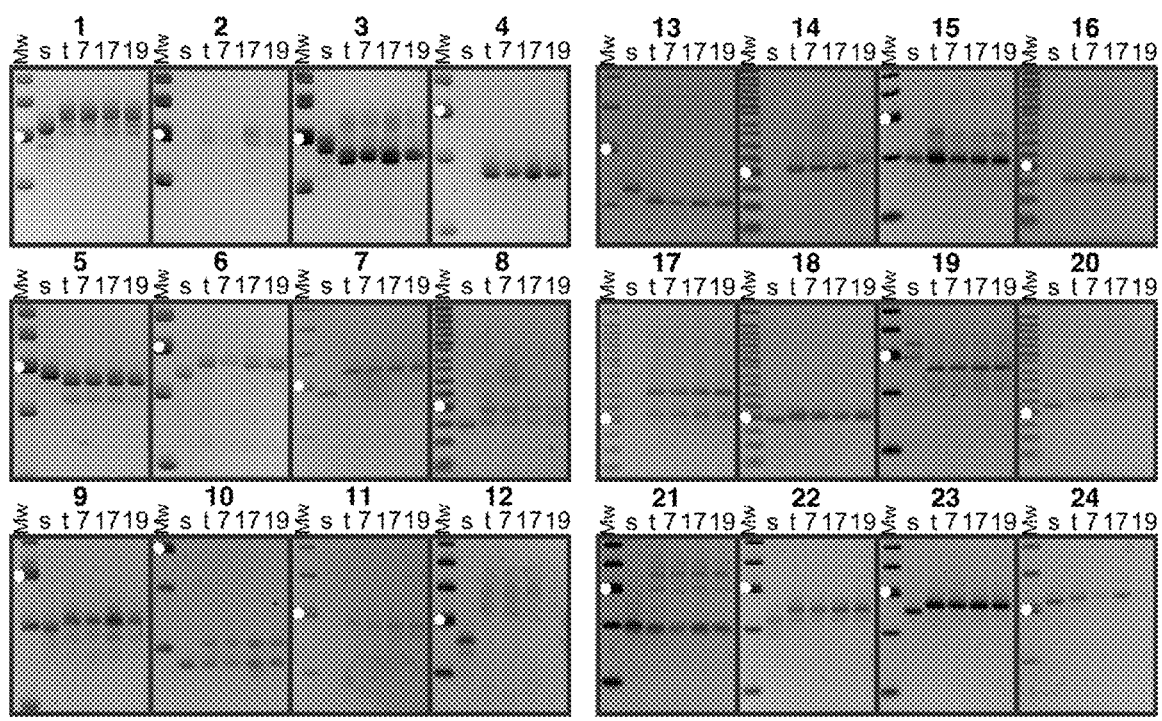

The CMS *N. tabacum* graft partner (Nt-CMS) carried a nuclear gentamycin resistance gene (Hajdukiewicz P, 1994). The fertile *N. sylvestris* (Ns-F) graft partner carried two plastid markers: a selectable spectinomycin resistance (aadA) and the visual bar$^{au}$ leaf color gene (FIG. 1D) (Maliga P & Svab Z, 2011). Graft transmission of mitochondrial DNA alters flower morphology (FIG. 1A), as plants regenerated from the graft transmission events had fertile flowers with anthers bearing pollen (FIG. 1B) and sterile flowers with anthers converted into petals (FIG. 1C). The two *Nicotiana* species were grafted (FIG. 1E), the graft junctions were sliced, and resistant shoots from the tissue slices were selected in culture for gentamycin resistance encoded in the nucleus of the CMS *N. tabacum* graft partner, and spectinomycin resistance encoded in the plastids of the fertile *N. sylvestris* graft partner. Three clones with resistance to both antibiotics were recovered in the culture of 14 graft junctions (FIG. 1F). The events were designated GT7, GT17 and GT19. The identity of plastids as *N. sylvestris* in the regenerated plants was confirmed by DNA gel blot analyses of all three lines and sequencing the plastid genome of the GT19-C line (FIGS. 2F-2H). The regenerated plants carried only the chromosomes of *N. tabacum*, the graft partner carrying the nuclear gentamycin resistance gene (FIG. 2I). Therefore, selection for the nuclear marker in *N. tabacum* and chloroplast marker in *N. sylvestris* yielded *N. tabacum* plants with chloroplasts from *N. sylvestris*, without input of *N. sylvestris* chromosomes.

From the three double-resistant calli eight plants were regenerated: GT7-A, GT7-C from callus GT7; GT17-B, GT17-C, GT17-G from callus GT17; and GT19-A, GT19-B and GT19-C from callus GT19. All but one had CMS flowers. The GT19-C plant was chimeric, with fertile flowers on two of the four branches suggesting co-transmission of fertile mitochondria with the *N. sylvestris* chloroplasts. We found three types of flowers on the GT19-C plants (FIG. 2B): CMS with petaloid-stigmatoid anthers (FIG. 2C), fertile anthers with ample pollen (FIG. 2E), and intermediate with partial conversion of anthers into petals (FIG. 2D). Seed from fertile flowers were obtained by self-pollination. Seed from sterile flowers was obtained by pollination with wild-type *N. tabacum* pollen. Fertile or CMS phenotype of the GT19-C seed progeny was stably maintained through three seed generations.

Recombination of Mitochondrial DNA

Next, we looked for DNA evidence of mitochondrial movement through the graft junction. We chose *N. tabacum* plants with *undulata* cytoplasm as one of the graft partners because the ptDNA of *N. tabacum* and *N. undulata* differ by 918 ptDNA markers (805 SNPs and 113 short indels) (Thyssen G et al., 2012), and we expected the mitochondrial DNA to be similarly divergent. Plant mitochondria continuously undergo repeated cycles of fusion and fission (Logan D C, 2010) therefore we expected to find recombinant mitochondrial genomes. We tested 24 polymorphic sites in the 430-kb mitochondrial genome (Table S5). The flower morphology and mtDNA markers of the GT7 (A, C) and GT17 (B, C, G) plants were *N. undulata* type. The mitochondrial genome of GT-19 graft plastid transmission progeny is a chimera of the fertile *N. sylvestris* and CMS *N. undulata* mitochondrial genomes. FIG. 3 shows the map positions of DNA polymorphic markers in the (FIG. 3A) *Nicotiana undulata*, (FIG. 3B) *Nicotiana sylvestris* and (FIG. 3C) GT-19 graft plastid transmission progeny on the *N. sylvestris* mtDNA map. Plants derived from the third event, GT19-A, B and C had chimeric mitochondrial genomes with eight markers derived from the fertile and sixteen from the CMS mitochondria (FIG. 3D). However, the mtDNA in the fertile and sterile branches could not be distinguished by the 24 markers.

Figure 4A:
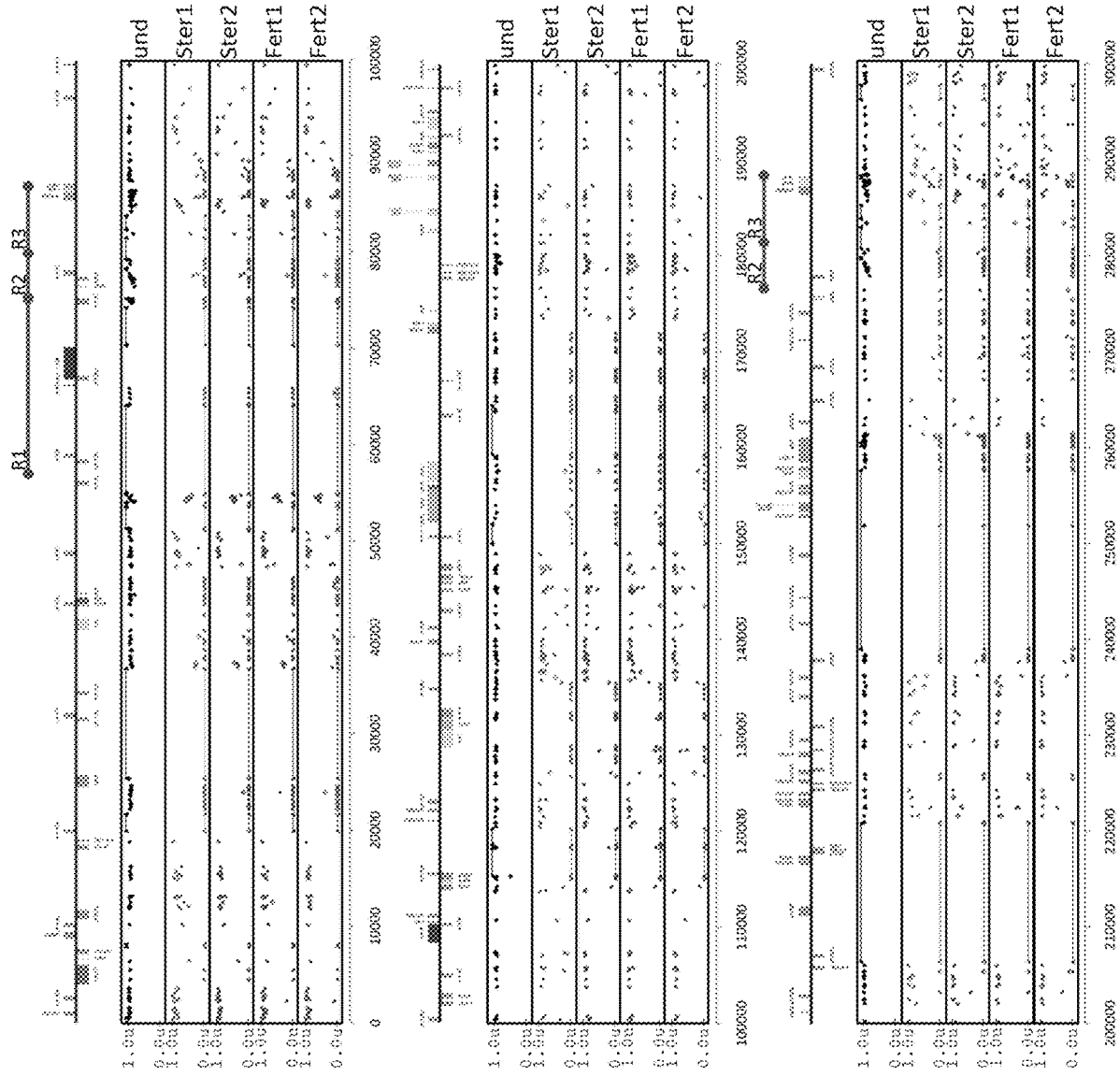
Figure 4B:
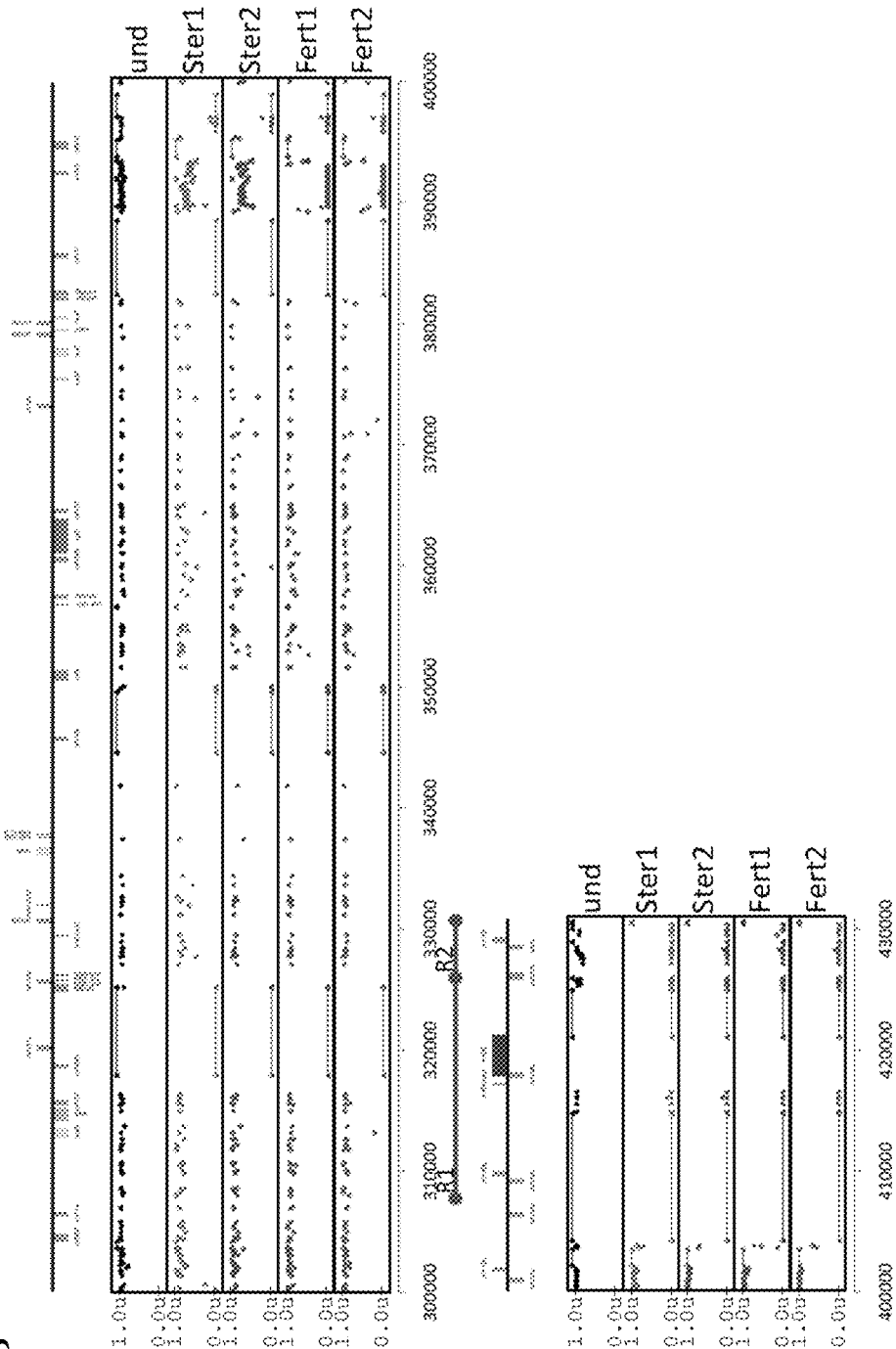
Figure 4C:
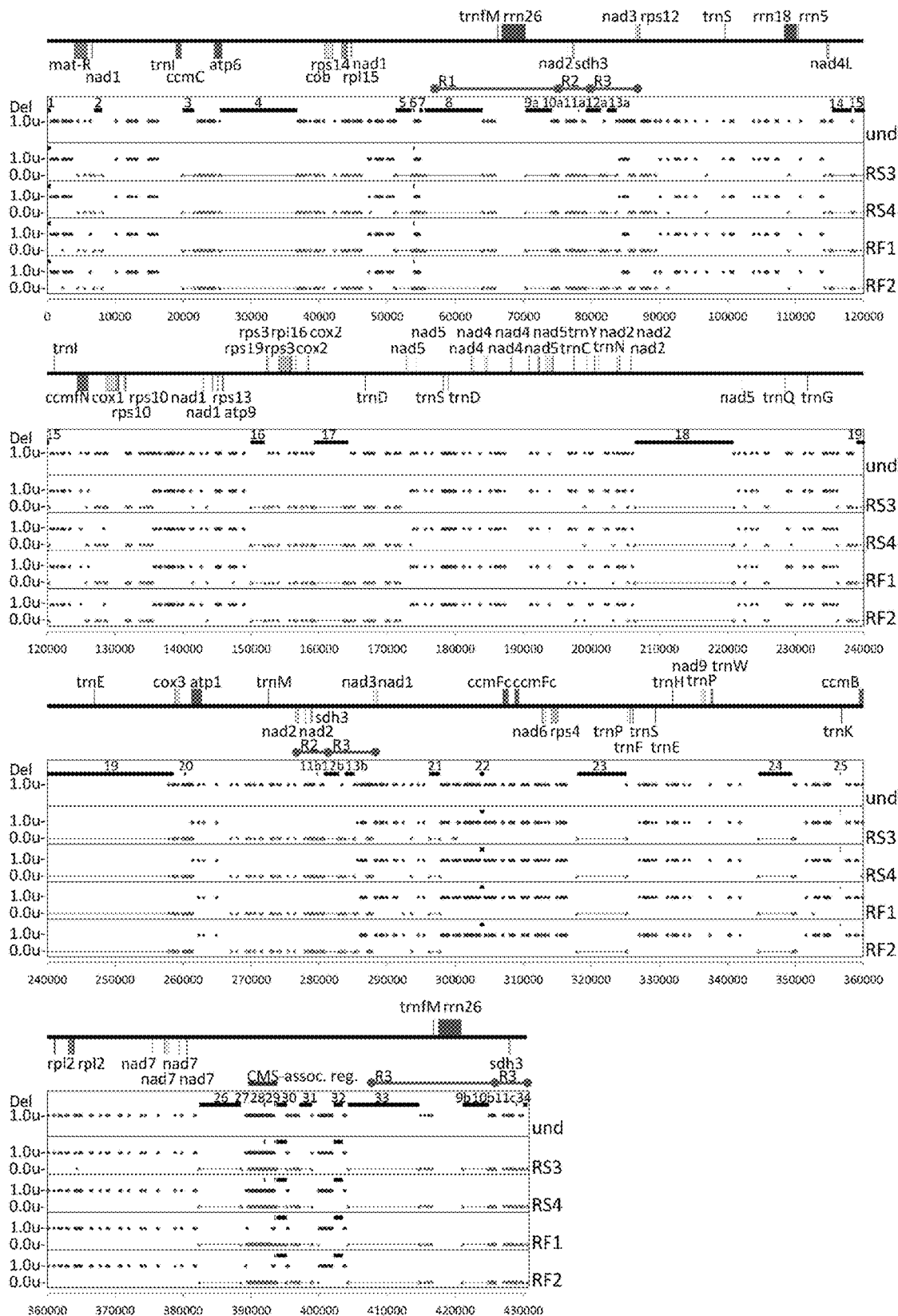

Introduction of the CMS trait is facilitated by information about the male sterility causing DNA sequences. This information has been obtained by the analyses of fertile and sterile recombinant mitochondrial genomes (FIGS. 4A-C), which differ in a 3 kb-region between the fertile and sterile plants. To identify the region of the mitochondrial genome responsible for fertility restoration, we assembled the complete mitochondrial genome of *N. sylvestris* (GenBank KT997964), and mitochondrial contigs of *N. undulata* and two fertile and two sterile first seed generation GT19-C progeny. The 279-kb sequence conserved between the *N. sylvestris* and *N. undulata* mitochondrial genomes differ by 977 DNA polymorphic markers (Table S6) and encode all genes present in the *N. sylvestris* mtDNA. The only exception is trnE, a gene encoding tRNA-UUC of plastid origin (246,982-247,053, GenBank NC_006581). However, a mitochondrial-derived trnE gene encoding tRNA-UUC is present in the *N. undulata* mtDNA. Plotted along the *N. sylvestris* genetic map in FIG. 4C is the origin of mtDNA in the recombinant mitochondrial genomes. The mtDNA in the plants is apparently mosaic, consisting of segments of *N. sylvestris* and *N. undulata* mtDNA. The *N. sylvestris* and *N. undulata* SNPs are symbolized by red and blue dots, respectively. The crossover sites are not always identical in the recombinant mitochondrial genomes. For example, both the fertile and sterile lines have *N. undulata* mtDNA at the beginning of the map, but the fertile lines have one *N. sylvestris* SNP at nucleotide 2,246 (FIG. 4C). Based on the switching of red and blue dots in the alignment, the Recombinant Fertile 1 and Fertile 2 (RF1, RF2) and Recombinant Sterile 3 and Sterile 4 (RS3 and RS4) mitochondrial genomes contain at least 65, 63, 57, and 58 crossover sites (FIG. 4C). Five recombination junctions have been PCR amplified and confirmed by Sanger sequencing (FIG. 4D).

Figure 5A:
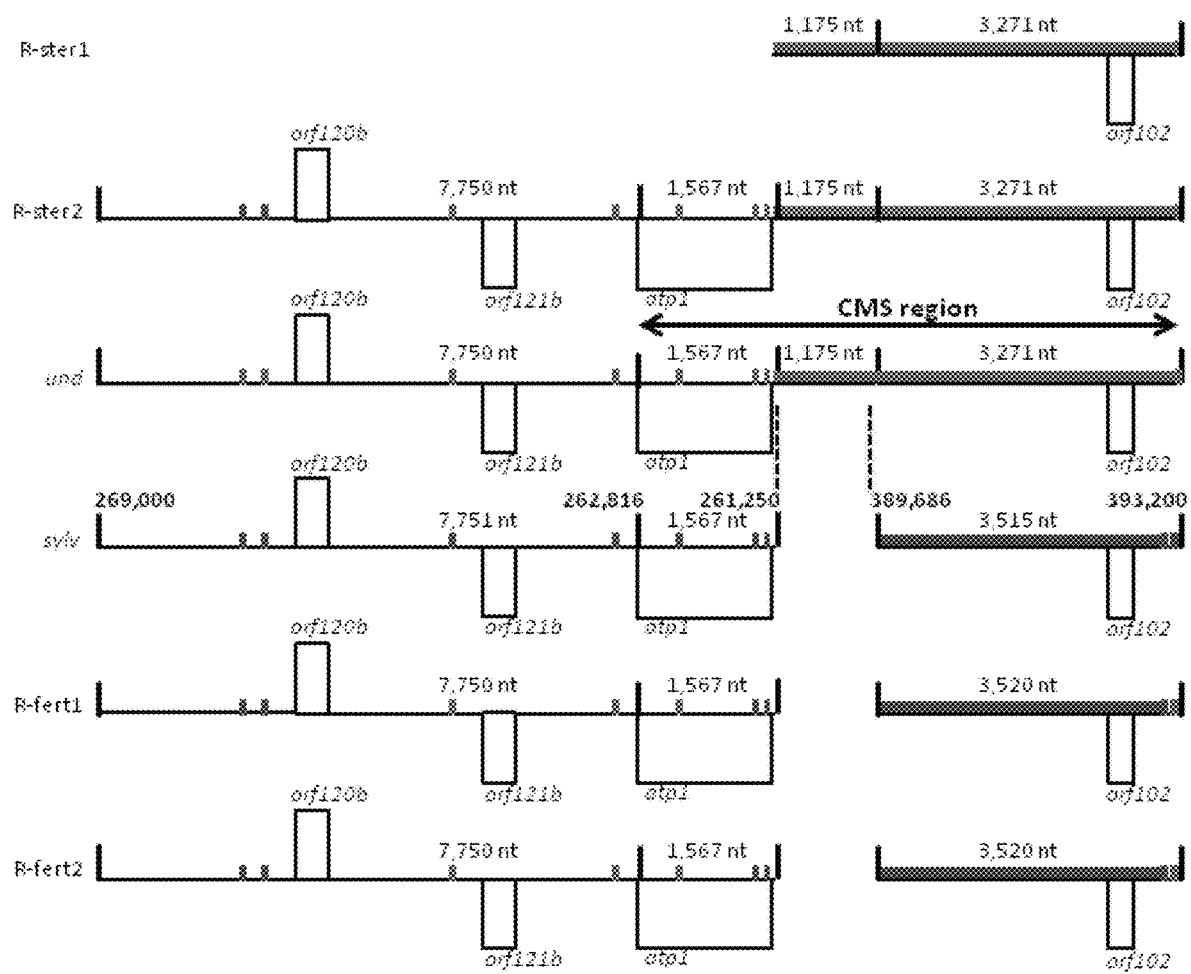
FIGS. 5A-5D: CMS co-segregates with a ~6 kb mitochondrial DNA region unique to the CMS *N. undulata* mitochondrial DNA marked as CMS region.
Figure 5B:
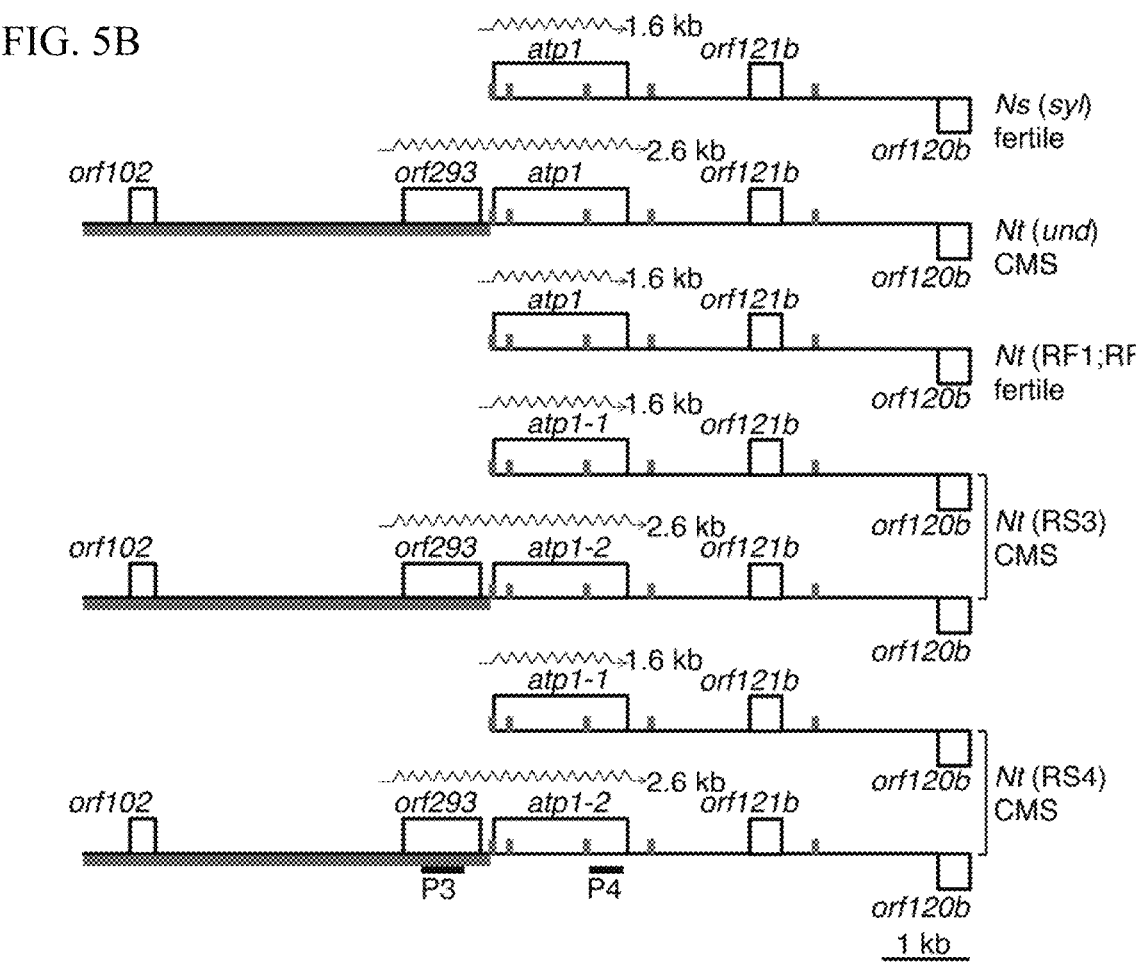
Figure 5C:
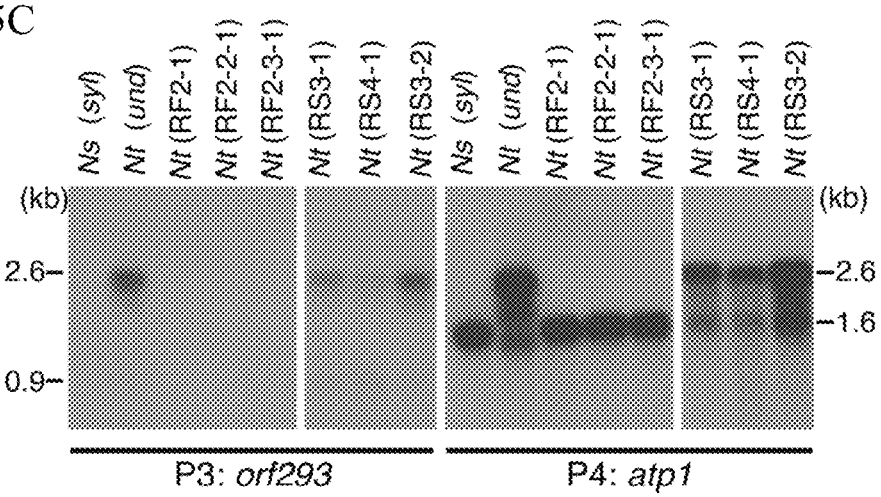
Figure 5D:
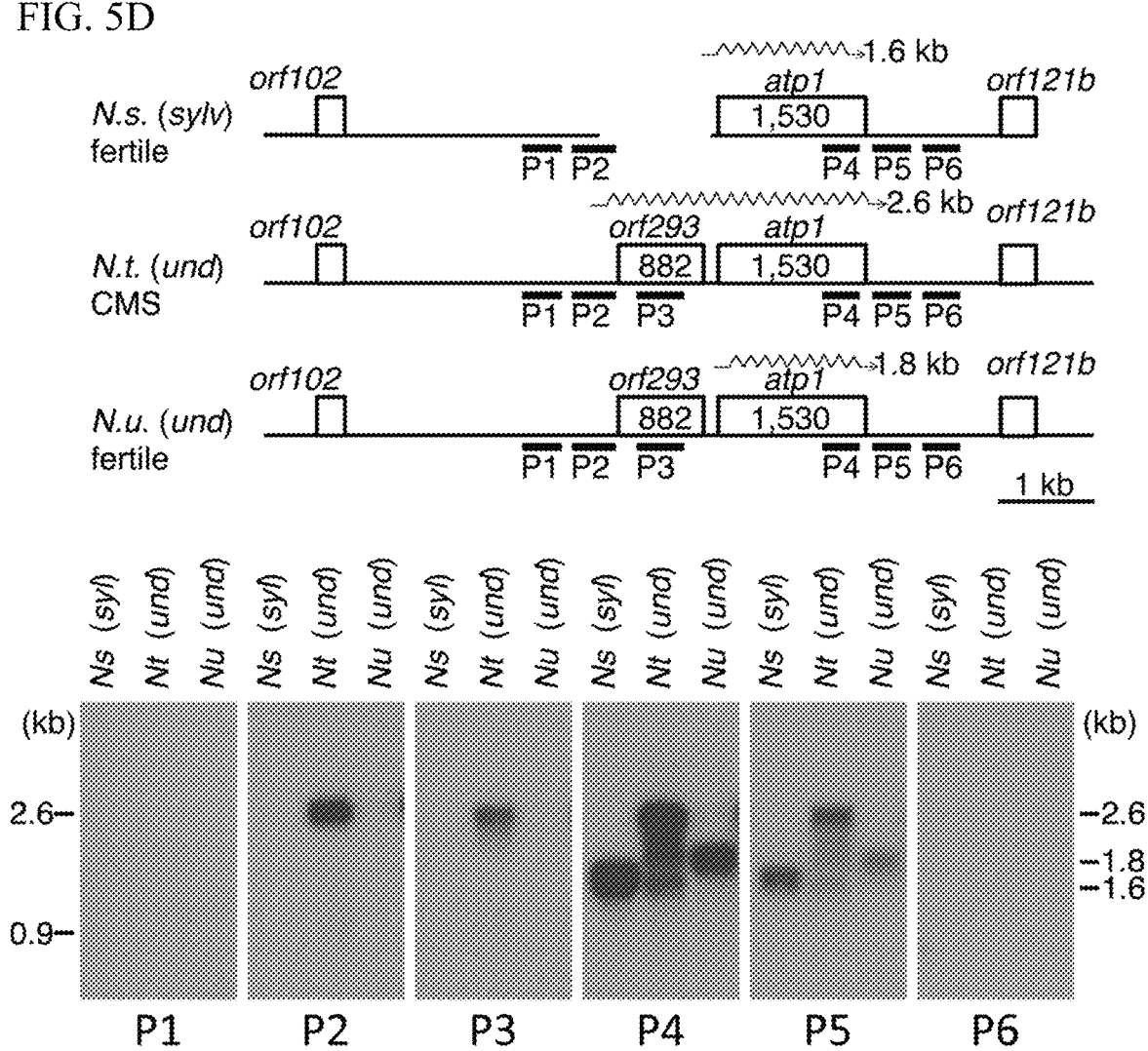

The map position of CMS-causing sequences is shown in FIG. 5A. Recombination of mitochondrial genomes at alternative sites facilitated the identification of the region likely to be responsible for CMS that manifests as homeotic conversion of anthers into stigmatoid petals in *N. tabacum* (FIG. 2A). Sequence alignments revealed that a 3.5-kb region correlates with male sterility: the two recombinants with sterile flowers carried the *N. undulata* sequence and the *N. sylvestris* sequence, while the fertile recombinants had the cognate region from *N. sylvestris* alone (CMS-associated region in FIG. 4C). Adjacent to the shared region is a 1.2-kb *N. undulata*-specific sequence encoding orf293 (FIG. 5B). RNA gel blot analyses confirmed that orf293 mRNA accumulates in CMS *N. tabacum* and sterile recombinants, but is absent in fertile *N. tabacum* and the fertile recombinants (FIG. 5C). The orf293 transcript is also absent in fertile *N. undulata* plants, the source of the cytoplasm, although the orf293 gene is present in the mitochondrial genome (FIG. 5D) (GenBank KU180495-KU180498). Absence of sterility-causing mitochondrial transcripts is expected when a nuclear fertility restorer gene is present (Chase C D, 2007; Hanson M R & Bentolila S, 2004). The predicted protein encoded by orf293 has three trans-membrane domains based on the TMHMM transmembrane protein topology program (Krogh A, 2001). Transmembrane domains are characteristic of sterility-causing mitochondrial genes (Chase C D, 2007; Bentolila S, 2004). The flower phenotype of plants carrying orf293 in mitochondria depends on the nuclear background: in *N. tabacum* the anthers are petaloid, or petaloid-stigmatoid (FIG. 2A); in *N. sylvestris*, the anthers are converted into stigmatoid structures (Thyssen G et al., 2012). Based on the flower phenotype, we tentatively named orf293 "homeotic conversion of anthers" (hca) gene.

The DNA sequence of CMS-causing *N. undulata* mitochondrial DNA (~6-kb) and the cognate sequence in the fertile *N. sylvestris* is given in FIG. 6. This sequence encodes mitochondrial ORF102, which has four predicted amino acid exchanges in the *N. undulata* ORF relative to the *N. sylvestris* ORF (FIG. 7). The presence of CMS-causing mtDNA can be tracked by sequencing PCR-amplified mitochondrial DNA. A convenient visual marker is the PCR fragment obtained with primers 5'-TTGCTTTGCCTCCT-TCCTTCTTC-3' (mt390702F; SEQ ID NO: 6) and 5'-TCT-GTAAGCCCCGAAACAGACTC-3' (mt390864R; SEQ ID NO: 7), amplifying a 163 nt fragment from *N. sylvestris* and a 142 nt fragment from *N. undulata* the mtDNA. This fragment is amplified from a region located at ~1.8 kb from ORF102.

Similar to plastids, mitochondrial RNAs also undergo extensive mRNA editing (Takenaka et al., 2013). The lack of RNA editing or partial RNA editing of heterologous mitochondrial mRNAs can also be the source of reduced plant viability. Incompatibility due to problems with editing of heterologous mitochondrial mRNA can be reduced or eliminated by replacement of the heterologous (tobacco) mtDNA with tomato mtDNA during repeated cycles of horizontal mtDNA transfer.

Example 2

CMS Tomato by Graft Transmission of *Petunia* Mitochondrial DNA

CMS in *Petunia* is associated with Pcf, a fused mitochondrial gene (Young and Hanson, 1987). The petunia fused gene is expressed at the protein level, and the abundance of the 25-kd protein is much lower in fertile plants carrying the dominant nuclear fertility restorer gene (Nivison and Hanson, 1989). The fertility restorer gene is a pentatricopeptide repeat-encoding gene (Bentolila et al., 2002) (US Patent 20030177535). For a review of CMS and fertility restoration in *Petunia*, see reference (Gillman et al., 2009).

The mechanism of male sterility is different in *Petunia* and the CMS92 tobacco line. In *Petunia*, CMS is due to the expression of a toxic protein rather than homeotic transformation of the anthers as in tobacco. Therefore, it may be also beneficial to introduce the *Petunia* Pcf gene into tomato mitochondria. The engineering steps required to introduce the Pcf gene into tomato are the same as described for the CMS92 tobacco mitochondrial DNA sequence. The plastid-nucleus compatibility problems are also the same, since *Petunia* plastids can replace tobacco plastid in the tobacco nuclear background (Glimelius & Bonnett, 1986). Protocols for plastid transformation to provide a marker for the selection of cell-to-cell movement of *Petunia* plastids are available (Zubko et al., 2004). Because the Pcf DNA sequence is known, introduction of the male-sterility causing gene can be tracked by PCR. If necessary, male sterility can be restored by introducing the fertility restorer gene into the tomato nucleus.

Example 3

Graft Transmission of CMS by Transient Selection for Nuclear Transfer

When transfer of CMS is carried out by selection for a plastid marker, the probability of co-transfer of CMS depends on how much cytoplasm is co-transferred with the plastids. The likelihood of success can be significantly enhanced when graft transmission is used first to obtain nuclear hybrids (Fuentes et al., 2014), in which case more complete mixing of the cytoplasm is likely by the movement of the larger nucleus through the graft junction. Indeed, three out of five nuclear graft transmission events was accompanied by formation of recombinant mitochondria (Fuentes et al., 2014). In Example 3 of the present invention both graft parents carry a different nuclear gene, such as the fertile Parent 1 (tomato) a gentamycin resistance gene and CMS Parent 2 (tobacco) a kanamycin resistance gene. Parent 2 also carries a selectable plastid marker, such as spectinomycin resistance. The two parents are grafted as in Example 1 and Example 2, and then the graft junction is sliced up and the tissue slices are selected in tissue culture for gentamycin-kanamycin resistance to recover nuclear hybrids. Nuclear hybrids of species such as tobacco and tomato are likely to be unstable. Thus initial double-selection should be followed by selection for the nuclear marker of Parent 1 (gentamycin resistance) and plastid marker of Parent 2 (spectinomycin resistance). In the absence of selection for the chromosomes of Parent 2, the tobacco chromosomes of Parent 2 are likely to be preferentially lost in the hybrid during cultivation in culture. The result is recovery Parent 1 (tomato) nucleus with chloroplasts of Parent 2 and recombinant mitochondria. Tobacco chromosomes retained in the regenerated tomato plants can be eliminated by repeated pollination of the plants with wild-type tomato pollen.

Example 4

Transmission of ptDNA in *N. tabacum/N. sylvestris* Graft Tissue

Materials and Methods

Partner P1 (Nt-pHC19) has an allotetraploid *Nicotiana tabacum* cv. Petit Havana (2N=48) nucleus with the aacC1 transgene for gentamycin resistance and wild-type *N. tabacum* plastid and mitochondrial genomes (Carrer H et al., 1990). Partner P2 (Ns-pCK2-6W2) has a wild-type diploid *N. sylvestris* TW137 (2N=24) nuclear genome, *N. undulata* plastids with aadA transgenes for spectinomycin selection and the aurea young leaf color phenotype (bar$^{au}$ gene), and cytoplasmic male sterile (CMS-92) mitochondria from *N. undulata* (Maliga P & Svab Z (2011). For grafting, the plants were grown aseptically on a medium containing MS salts and 3% sucrose (Lutz K A & Maliga P, 2007). Plants were regenerated from the graft junctions on RMOP shoot regeneration media supplemented with 500 mg/L spectinomycin and 100 mg/L gentamycin (Lutz K A & Maliga P, 2007). Southern probing for ptDNA polymorphisms was carried out using six previously identified polymorphic regions (Svab Z & Maliga P, 2007). Organellar DNA was amplified using total cellular DNA as a template (Murray M G & Thompson W F, 1980) using appropriate PCR primers (Table 51, Table S2). Primer design for ptDNA was based on GenBank Accession Z00044 and JN563929 and for mtDNA on GenBank Accession BA000042. The plastid genomes were amplified in 34 PCR reactions using primers listed in Table S3. DNA sequence was determined on an Illumina Genome Analyzer II using 80 bp paired-end (500 bp insert) library. Total leaf DNA fragments of P1, P2, G1, G3 and G4 plants were also analyzed on a SOLiD 5500xl sequencer using 76-nucleotide reads. Reference guided assembly was essentially carried out as described (Cronn R et al., 2008). Nuclear SSR markers (Moon H S et al., 2008) were amplified using primers listed in Table S4.

Experimental Design

Our objective was to determine if chloroplasts or mitochondria could be shared among supracellular plant cells. To test this hypothesis, we grafted two different species of tobacco with genetic markers in their plastids and mitochondria. Grafting triggers formation of new plasmodesmatal connections (Ehlers K & Kollmann R, 2001) that creates a conduit for cell-to cell movement of organelles. We report here evidence supporting the transfer of plastids via newly formed plasmodesmata. However, the related (non-selected) mitochondria were absent in the same plants, suggesting independent transfer of plastids through the graft junction. We discuss acquisition of plastids from neighboring cells via plasmodesmata as a potential mechanism to repopulate cells with functional organelles and new opportunities created by the cell-to-cell movement of plastids for biotechnological applications.

Figure 8A:
FIGS. 8A-8B: Phenotypes of the graft partners and the G1 graft transfer plant.
Figure 8B:
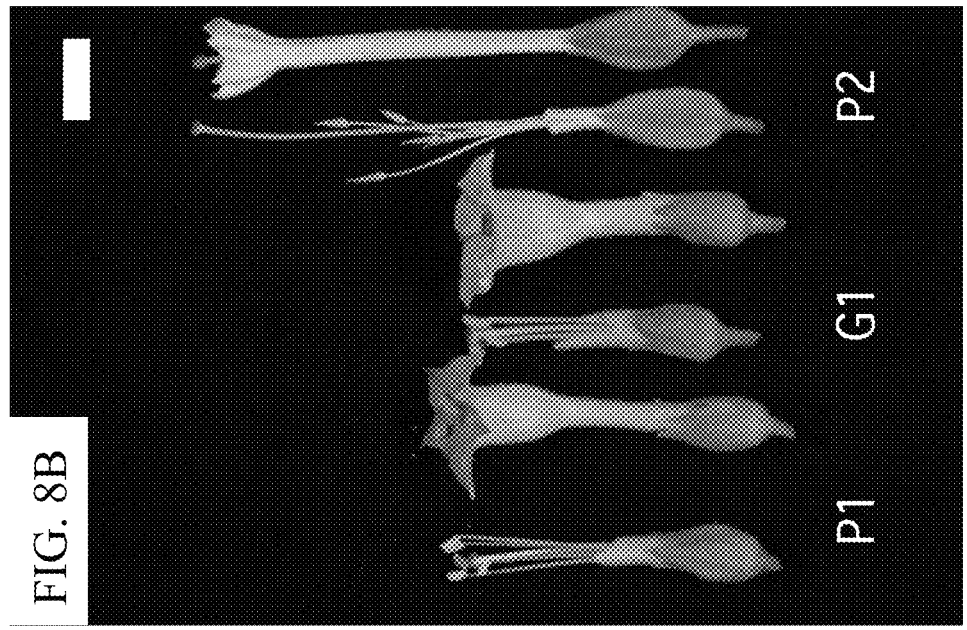
Figure 9B:
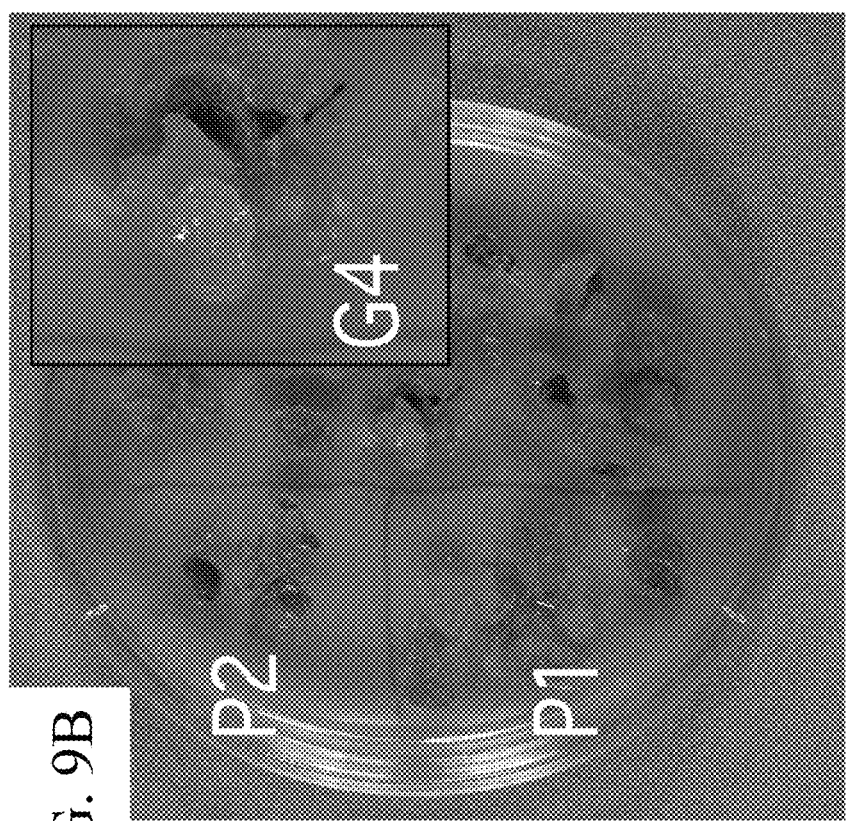
FIGS. 9A-9B: Identification of plastid graft transfer events.
Figure 9A:
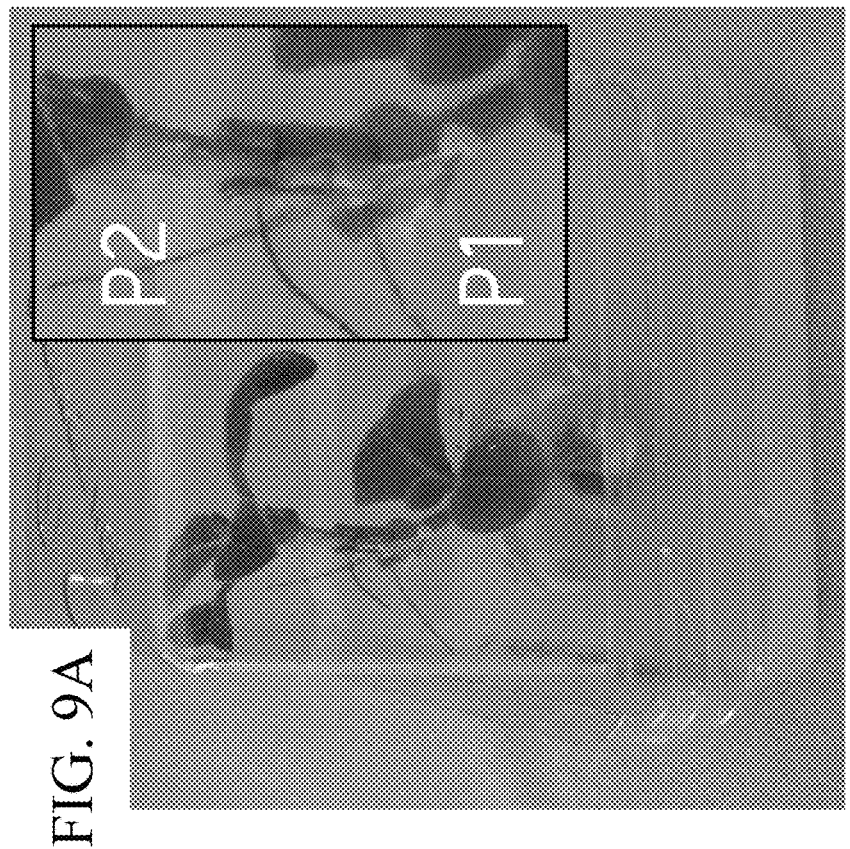

Because of the difficulty to directly observe rare intercellular organelle movement, we chose graft partners with distinct nuclear and organellar genomes to test for cell-to-cell transfer of plastids and mitochondria in graft junctions (FIG. 8A). We grafted two species of tobacco, *Nicotiana tabacum* (partner P1) with a selectable transgenic nuclear gentamycin resistance gene and *Nicotiana sylvestris* (partner P2) with plastids carrying a selectable spectinomycin resistance (aadA) gene and the aurea young leaf color phenotype (bar$^{au}$ gene). The *N. sylvestris* partner carried the plastids and mitochondria of a third species, *Nicotiana undulata*, providing a large number of organellar DNA markers. The P1 partner with the *N. tabacum* nucleus was fertile and the P2 partner with the *N. sylvestris* nucleus was cytoplasmic male sterile (FIG. 8A), a trait controlled by mitochondria (Gillman et al., 2009). The grafted plants were grown in culture for ten days (FIG. 9A) and sections of the graft junctions were selected for the gentamycin and spectinomycin resistance traits carried by the P1 nucleus and in P2 plastids, respectively (FIG. 9B). Out of 30 graft junctions a total of three plastid graft transmission (PGT) events (G1, G3, G4) were recovered. The plants regenerated from the graft junction displayed the leaf morphology, growth habit and pink flowers associated with the selected *N. tabacum* nucleus, but the aurea leaf color of the P2 partner, a plastid trait (FIG. 8B).

No Exchange of Chromosomes in the PGT Plants

Figure 10:
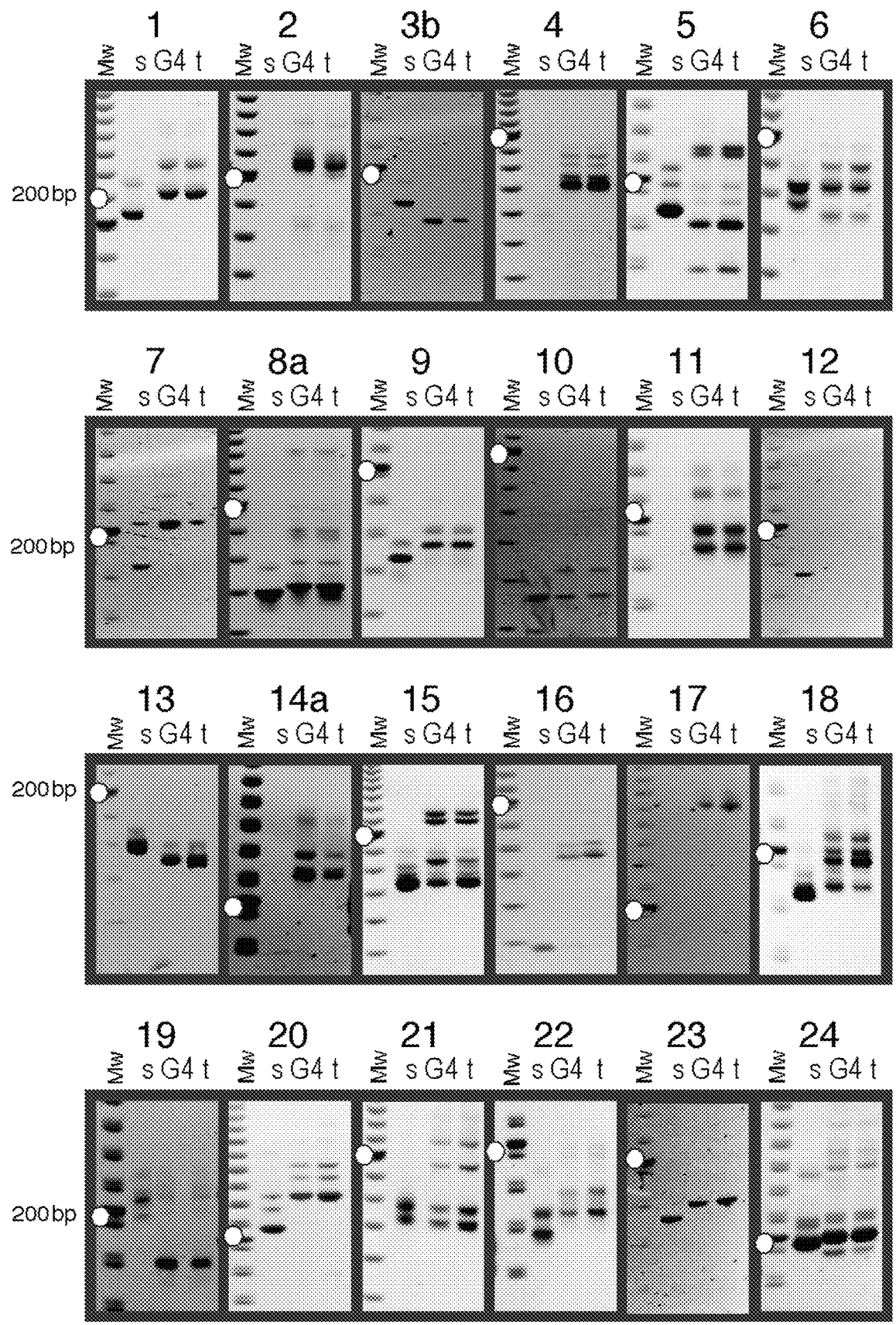
FIG. 10: SSR markers confirm *N. tabacum* chromosomes in the G4 plant by testing each of the 24 chromosomes (numbered 1-24). Lanes are marked with s, G and t for the P2, G1 and P1 plants (see caption to FIG. 8). Some markers do not amplify the *N. sylvestris* template (Moon H S et al., 2008). White dots mark the 200-bp fragment of the 20-bp molecular weight ladder.

To investigate the contribution of nuclear genetic material to the PGT plants, we examined twenty-four simple sequence repeat (SSR, or microsatellite) polymorphic DNA markers previously mapped to each of the *N. tabacum* chromosomes (Moon H S et al., 2008). These markers distinguished *N. tabacum* from *N. sylvestris* ecotype TW137 and indicated the presence of the chromosomes of the *N. tabacum* P1 partner that carried the selectable nuclear gene without contribution from the non-selected P2 *N. sylvestris* nucleus (FIG. 10). The presence of chromosomal markers from one partner excluded chimera formation as the source of double resistance of the G1, G3 and G4 PGT plants.

Mitochondria Remain Associated with the Selected Nucleus

The graft partners carried distinct mitochondrial genomes determining the flower type (FIG. 8B). The P1 partner with the *N. tabacum* nucleus had normal anthers and produced fertile pollen while the P2 partner with the *N. sylvestris* nucleus had stigmatoid anthers, a phenotype controlled by mitochondria. Interestingly, the G1, G3 and G4 PGT plants were male fertile and lacked the stigmatoid anthers of the CMS P2 partner. In line with the flower morphology, the CMS92 mtDNA markers were absent in the G1, G3 and G4 plants. To determine the source of the mitochondrial genome in the PGT plants, we identified six SNP and indel markers that are suitable to distinguish the *N. undulata* CMS92 mtDNA (FIG. 11A) from the fertile *N. tabacum* mtDNA (Yukawa M et al., 2006). Sanger sequencing of PCR fragments indicated that the G1, G3 and G4 plants have the mitochondrial genome of the nuclear donor (FIGS. 11B and 11C). Thus, we did not find evidence for the transfer of mitochondrial DNA in the PGT plants. Given the tendency of mitochondria for fusion (Sheahan M B et al., 2005) and mtDNA for recombination (Gillman J D et al., 2009; Boeshore M L et al., 1985), would mtDNA be transferred, we would expect to find at least chimeric mtDNA. The absence of non-selected mitochondrial DNA suggests limited organelle transfer that did not involve large-scale mixing of the two cytoplasms at the graft junction. Although we did not find evidence for the co-transfer of mtDNA transfer with ptDNA in the lines tested, it is possible that mtDNA transfer could be detected in a larger PGT plant population.

PGT Plants Contain the Entire Selected Plastid Genome

Figure 12A:
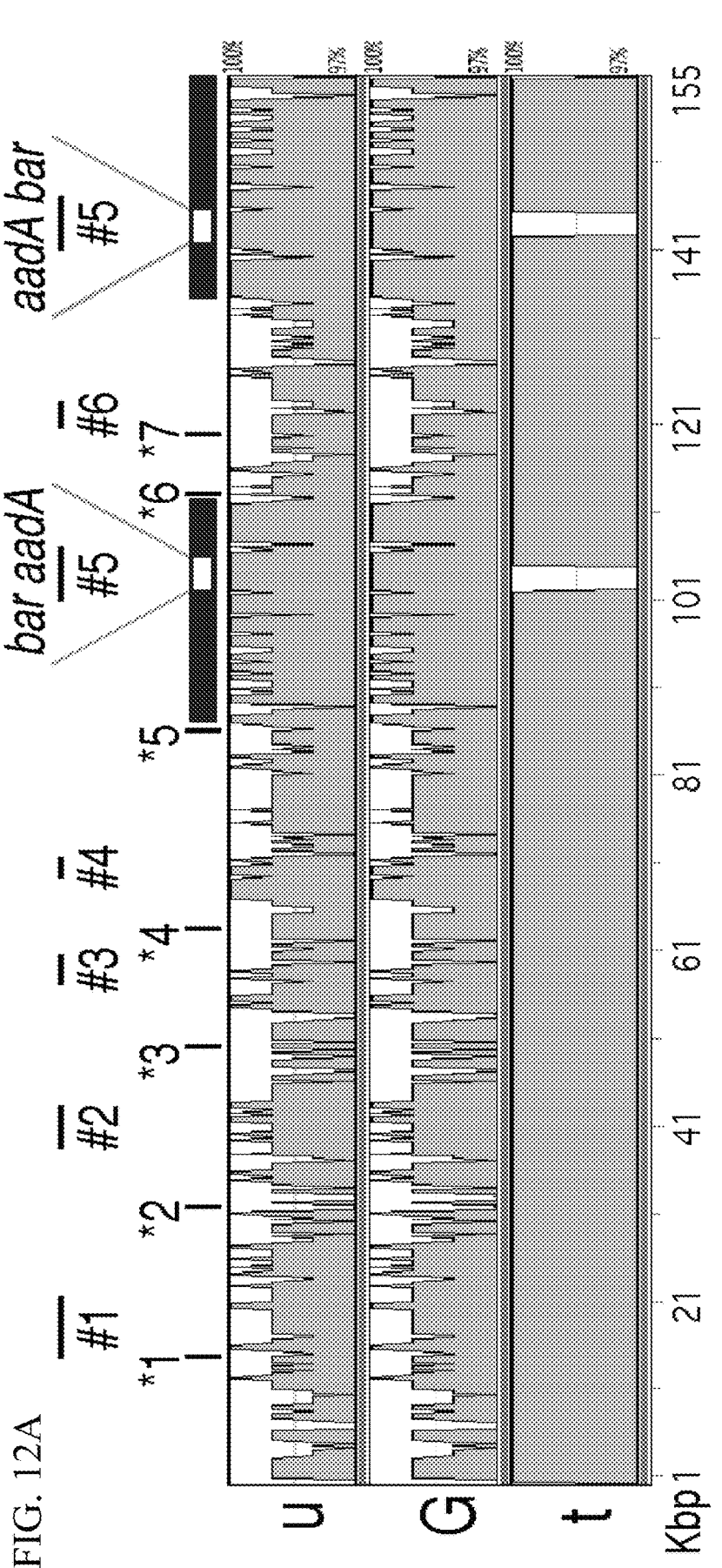
Figure 12C:
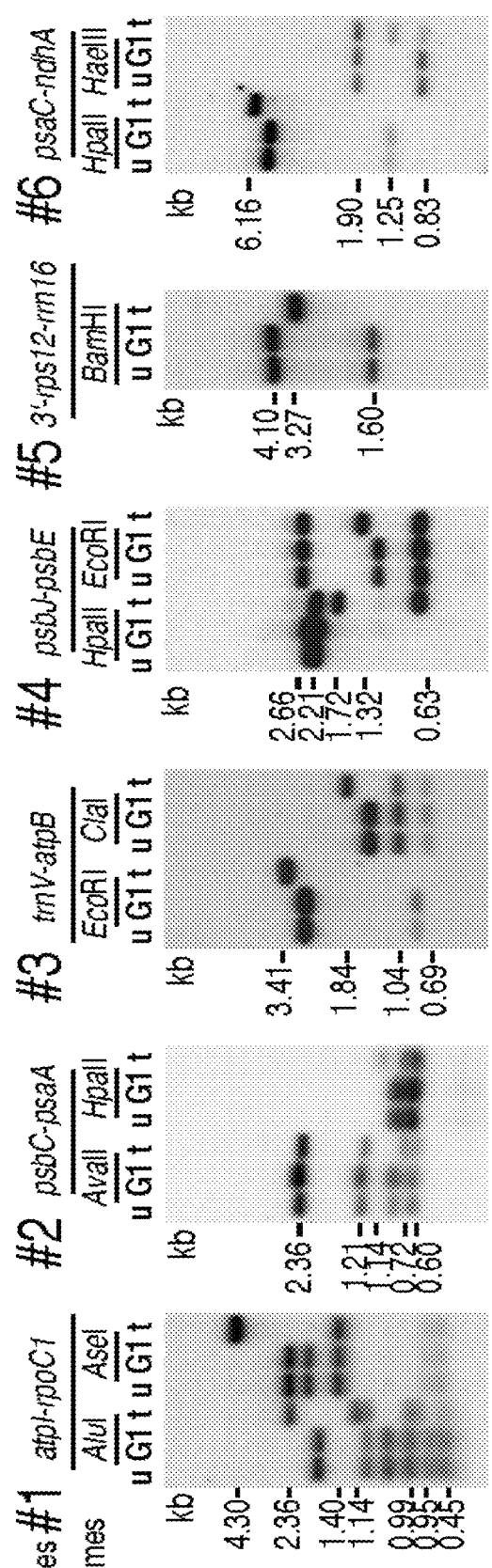

Dual selection for the nucleus- and plastid-encoded antibiotic resistances ensured that the PGT plants would carry both transgenes. The *N. tabacum*-specific SSR markers in the G1, G3 and G4 plants indicated the presence of the P1 chromosomes alone in the PGT plants. However, the presence of the plastid markers did not distinguish between a transformation-like process that involves incorporation of ptDNA fragments and intercellular movement of plastids implied by the transfer of complete plastid genomes, either of which is compatible with the earlier report (Stegemann S & Bock R, 2009). To determine how much of the P2 ptDNA is present in the G1, G3 and G4 plants, we first examined markers distant from the transgenes by probing total cellular DNA on blots. Southern probing of the six previously identified RFLP markers (FIG. 12C) and PCR analyses (FIG. 12B) suggested the presence of the entire plastid genome of P2 partner and that the PGT plants carried a uniform population of P2 transplastomes. To exhaust the search for a contribution to the G1 plastid genome from the non-selected P1 plastome, we performed next generation sequencing of the plastid genomes of the P1 and P2 partners and the G1, G3 and G4 PGT plants. We report here the sequence of the 160,743 nucleotide transplastomes in the P2 partner and the three PGT plants are identical (GenBank accession no. JN563930). The P2 and PGT plastid genomes are larger than the 155,863 nucleotide wild type *N. undulata* plastid genome (GenBank accession no. JN563929), as the transplastomes also contain spectinomycin resistance (aadA) and the aurea bar$^{au}$ transgenes. We also sequenced the plastid genome in partner P1 that carries the wild-type *N. tabacum* ptDNA of cv. Petit Havana. We have found that the sequence of cv. Petit Havana ptDNA is identical with the cv. Bright Yellow sequence deposited in GenBank (GenBank Accession number Z00044). However, the *N. undulata* ptDNA differs from the *N. tabacum* cv. Petit Havana ptDNA by 805 SNPs, 52 insertions and 61 deletions and the transgene cassettes. Differences between the plastid genomes are depicted on the mVISTA identity plots shown in FIG. 12A. Importantly, we observed all of these polymorphic loci, with an average density of 200 bp/SNP (170 bp/polymorphism) in the PGT graft transmission plants indicating the transfer of intact ptDNA from the P2 graft partner. We also tested transmission of the plastid-encoded spectinomycin resistance in reciprocal backcrosses. When the G1 plant was the mother and the wild type the father, each of the 208 seedlings was resistant whereas when the G1 plant was the father and the wild type the mother, each of the 318 seedlings was spectinomycin sensitive. Thus, spectinomycin resistance exhibited uniform, maternal inheritance, as expected for a homoplastomic *N. tabacum*, a species with strict maternal plastid inheritance.

Cell-to-Cell Migration of Plastids

We report here cell-to-cell movement of entire plastid genomes. We considered two possible mechanisms for the transfer of genome-size ptDNA: the intercellular transport of extra-organellar ("naked") DNA or the ptDNA traveling within an intact organelle. Selection for movement of ptDNA to the nucleus lead to the discovery of ptDNA transfer to the nucleus by incorporation of kilobase-size ptDNA fragments, most probably from degraded organellar genomes (Huang C Y et al., 2003; Stegemann S et al., 2003; Sheppard A E et al., 2008). Movement of entire genomes may require more protection than the fragments. Better protection could be provided if the extra-organellar ptDNA would be encapsulated in membrane-bound vesicles that are shed from fragmented chloroplast stromules (Hanson M R & Sattarzadeh A, 2011). Because of the need for capacity for translation, plastids cannot be created de novo from membranes and DNA (Zubko M K & Day A, 1998). Thus, if "naked" ptDNA is transferred, an invading plastome would need to enter an existing plastid with transcription and translation machinery and displace the existing plastome by a transformation-like process to explain our observations. However, a transformation-like process would yield mosaic genomes if different genomes were present, because plastid genomes within an organelle undergo frequent recombination (Palmer J D, 1983; Medgyesy P et al., 1985; Fejes E et al., 1990). The absence of chimeric genomes in the PGT plants makes it unlikely that naked DNA transfer is the mechanism of intercellular ptDNA transfer.

Figure 13C:
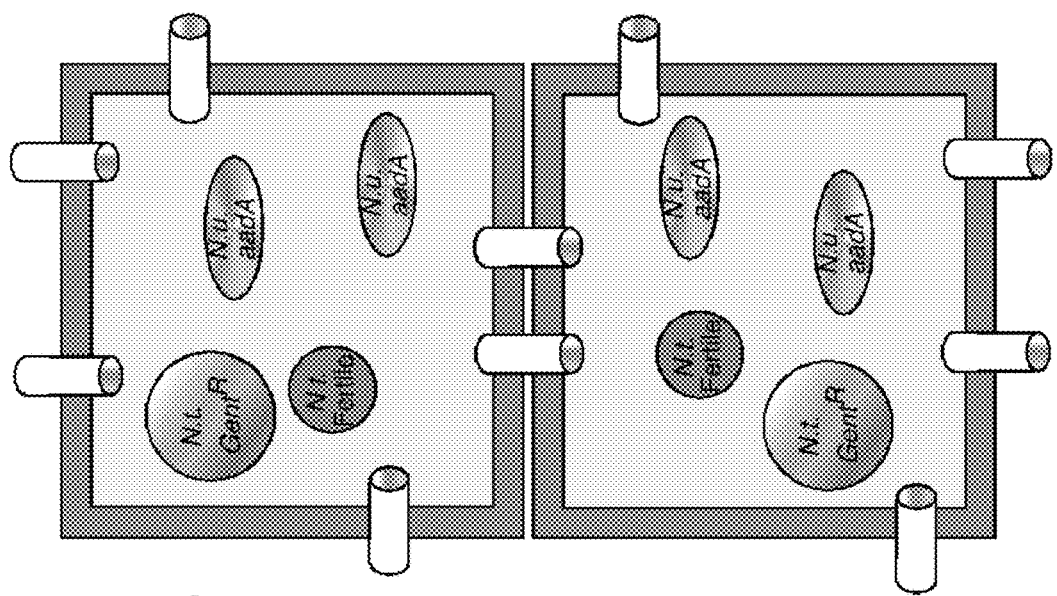
FIGS. 13A-13C: Model for cell-to-cell movement of plastids via initial cytoplasmic connection in graft junctions.
Figure 13B:
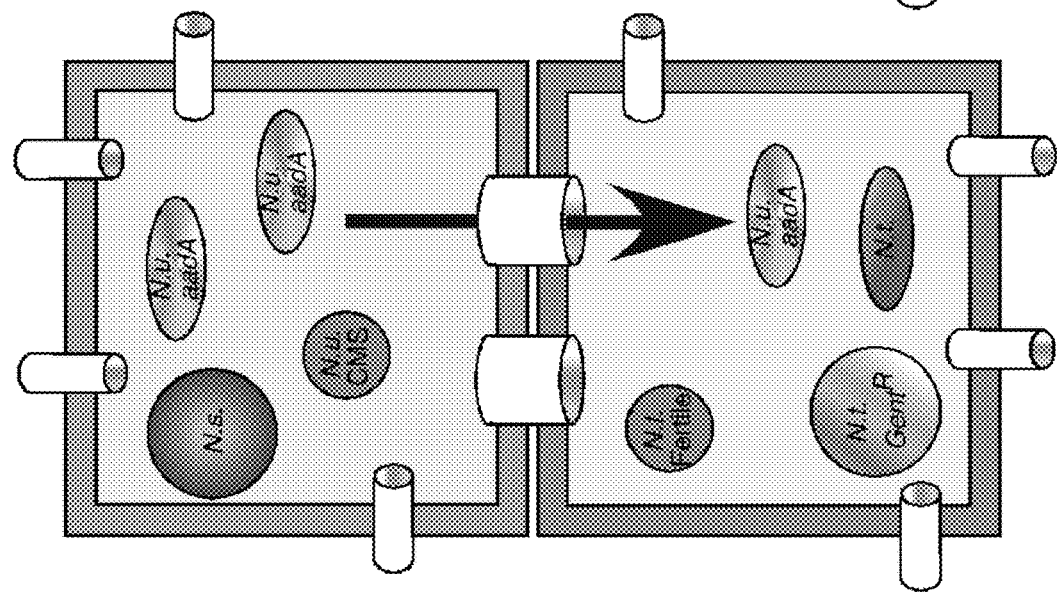
Figure 13A:
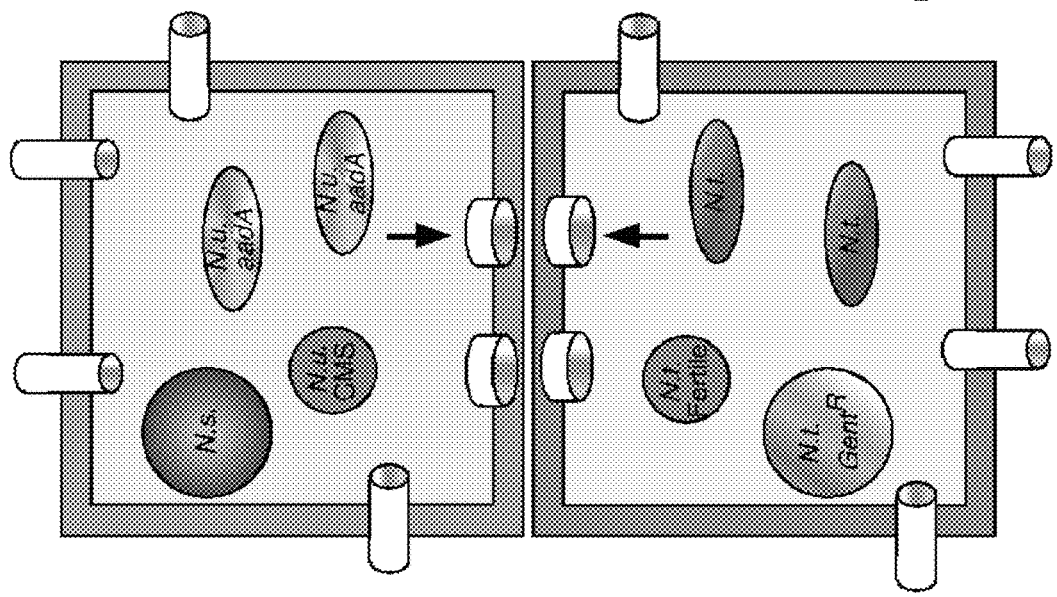

More likely vehicles of cell-to-cell movement of entire plastid genomes could be the organelles themselves. The avenue for the movement of intact organelles could be damage to cell walls that allows for some mixing of cytoplasms in the graft junctions. A more likely mechanism would be the transfer of proplastids via newly formed connections between cells that are well documented at graft junctions (Ehlers K & Kollmann R, 2001). The size of proplastids, about one micrometer, is well above the size exclusion limit of plasmodesmata normally defined by molecular weight. However, the size exclusion limit changes during development and depends on tissue type (Lucas W J et al., 2009; Burch-Smith T M et al., 2011). We speculate that the new openings, formed by thinning of opposing cell walls at the site of future plasmodesmata, permit intercellular movement of proplastids. Our preferred model of intercellular plastid transfer in graft junctions is shown in FIGS. 13A-C.

The capacity of a plant cell to acquire organelles from a neighboring cell is a basic biological process. Acquisition of plastids from neighboring cells may be important because once the ribosomes are lost, translation cannot be restored, since some of the ribosomal proteins are encoded in the plastid genome and their translation is dependent on plastid ribosomes (Zubko M K & Day A, 1998). Therefore, during certain stages of development, including dedifferentiation associated with forming new connections in grafted tissues (Ehlers K & Kollmann R, 2001), the plasmodesmata may allow the transport of organelles to ensure the continuity of functional DNA containing organelles. In this regard it is intriguing to note that the redox state of plastids regulates symplastic permeability and that ectopic expression of the proplastid-targeted GAT1 protein increased plasmodesmal size exclusion limit (Benitez-Alfonso Y et al., 2009). The functional state of mitochondria also regulates the size exclusion limit of intercellular trafficking (Stonebloom S et al., 2009) and reprogramming of diseased mammalian cells was associated with acquisition of functional mitochondria (Acquistapace A et al., 2011). The discovery of intercellular movement of plastids now enables testing the biological significance of this process in plants.

While the protocol described here is based on wedge grafting, decapitation of the rootstock and separation of scion from its root system is not necessary to obtain grafting. Natural grafting has been observed between plants in nature, when graft junction forms between plants growing in close proximity (Bock R, 2010). Accordingly, wedge grafting may be replaced by alternative protocols based on natural grafting. In one approach, the surface of the stem of the graft partners are removed and the stems are tied together to mimic natural grafts. PGT plants can be recovered from the graft junctions by tissue culture selection as described in the present application, or identified based on plant morphological markers and visual plastid markers in shoots regenerated from the graft junction. See U.S. patent application Ser. No. 13/326,295.

Intercellular movement of organelles should not be limited to intact plants, but should be applicable to any two cells making a new contact enabling cell-to-cell movement of plant organelles. Such cells may be in tissue culture, said first and second plants comprising distinct plastid and nuclear genetic markers, enabling selection for PGT events. Recovery of PGT (organelle) events in tissue culture may be particularly beneficial when grafting is technically challenging, such as in monocotyledonous plants.

Applications in Plastid Genetics and Biotechnology

Because in most species both plastids and mitochondria are maternally inherited, they cannot be separated by crossing. Thus far protoplast fusion has been the only option to obtain new combinations of plastids and mitochondria (Gillman J D et al., 2009). The result is intercellular transfer of parental plastids, but formation of recombinant mitochondrial genomes. The protocol we report here enables combination of parental plastids and non-recombinant mitochondria by PGT, a significant improvement over the protoplast-based process that yields recombinant mitochondria.

An additional application of PGT could be rapid introgression of transformed plastids into commercial cultivars. Plastid transformation is a powerful tool for biotechnological applications because the transgenes that are integrated into the plastid genome are expressed at high levels, can be clustered in operons and are not subject to silencing (Maliga P & Bock R, 2011; Cardi T et al., 2010). Currently the option is to transform the plastids in permissive cultivars then introduce them into commercial lines by repeated backcrossing using the commercial cultivar as a recurrent pollen parent. Based on the findings disclosed herein, backcrossing can be replaced in the future by graft transfer of the transformed plastids, instantly yielding a substitution line carrying the valuable commercial nuclear genome combined with transgenic plastids.

Example 5

Introduction of Autoluminescent Chloroplasts into Genetically Sterile Plants or into Plants Lacking Flowers Plastid transformation currently is a tissue culture dependent protocol that can be performed only with tissue-culture responsive genetic lines. Introduction of transformed plastid genomes into commercially useful lines requires repeated cycles of backcrosses. Inter-cellular transfer of organellar DNA in tissue grafts enables one-step transfer of plastid genomes in the absence of the transfer of nuclear genetic information, eliminating the need for backcrosses. Furthermore, graft transfer of plastids is possible between sterile plants lacking flowers and between sexually incompatible genetic lines.

Desirable plastids for transfer by non-sexual means may be autoluminescent plastids of different plant species carrying the lux operon (Krichevsky A et al., 2010) and the following recipients:
(1) Fertile lines that are sexually compatible, but encode desirable traits in their nuclei.
(2) Fertile lines that are sexually incompatible, thus introduction could not be accomplished by crossing.
(3) Plants, which lack flower organs or have flower organs but are sterile.

Example 6

Transmission of mtDNA in the *N. tabacum*/*N. sylvestris* Graft

We did not find evidence for co-transfer of the non-selected mtDNA with the selected ptDNA. Even if the mitochondria (mtDNA) were co-transferred with plastids, they were likely lost due to the absence of direct selection for mitochondrial traits. Thus, testing a larger population of PGT plants could possibly yield plants expressing the CMS flower morphology, a mitochondrial trait. A factor in the lack of recovering CMS plants could be the presumed recessive nature of *Nicotiana undulata* CMS, implied by the relatively small number of CMS plants recovered in somatic hybrids (Bonnett H T & Glimelius K, 1983). Because in our case plastids from the CMS P2 partner have moved into the fertile P1 partner, if recessive, the CMS mitochondrial trait remains undetected, unless the dominant fertile mitochondrial determinants are lost. In order to increase the likelihood of detecting the co-transfer of mitochondria (mtDNA) with plastids, we will utilize fertile plants as the source of plastids, because detecting restoration of fertile flower morphology, a dominant trait, in a sterile partner is more likely in regenerated plants.

It is clear that the foregoing methods are useful for engineering plants and crops having desirable characteristics without the need for extensive back crossing.

REFERENCES

Acquistapace A et al. (2011) Human mesenchymal stem cells reprogram adult cardiomyocytes toward a progenitor-like state through partial cell fusion and mitochondria transfer. *Stem Cells* 29:812-824.
Allen J O et al. (2007) Comparisons among two fertile and three male-sterile mitochondrial genomes of maize. *Genetics* 177(2):1173-1192.
Arimura S et al. (2004) Frequent fusion and fission of plant mitochondria with unequal nucleoid distribution. *Proc. Natl. Acad. Sci. USA* 101(20):7805-7808.
Belliard G et al. (1979) Mitochondrial recombination in cytoplasmic hybrids of *Nicotiana tabacum* by protoplast fusion. *Nature* 281:401-403.
Benitez-Alfonso Y et al. (2009) Control of *Arabidopsis* meristem development by thioredoxin-dependent regulation of intercellular transport. *Proc. Natl. Acad. Sci. USA* 106:3615-3620.
Bentolila S et al. (2002) A pentatricopeptide repeat-containing gene restores fertility to cytoplasmic male-sterile plants. *Proc. Natl. Acad. Sci. USA* 99:10887-10892.
Bergthorsson U et al. (2003) Widespread horizontal transfer of mitochondrial genes in flowering plants. *Nature* 424 (6945):197-201.
Bindler G et al. (2011) A high density genetic map of tobacco (*Nicotiana tabacum* L.) obtained from large scale microsatellite marker development. *Theor. Appl. Genet.* 123(2):219-230.
Bock R (2010) The give-and-take of DNA: horizontal gene transfer in plants. *Trends Plant Sci.* 15:11-22.
Boeshore M L et al. (1985) A variant mitochondrial DNA arrangement specific to *Petunia* stable sterile somatic hybrids. *Plant Mol. Biol.* 4:125-132.
Boeshore M L et al. (1983) Novel composition of mitochondrial genomes in *Petunia* somatic hybrids derived from cytoplasmic male sterile and fertile plants. *Mol. Gen. Genet.* 190:459-467.
Bonnett H T & Glimelius K (1983) Somatic hybridization in *Nicotiana*: behaviour of organelles after fusion of protoplasts from male-fertile and male-sterile cultivars. *Theor. Appl. Genet.* 65:213-217.
Burch-Smith T M et al. (2011) Plasmodesmata during development: re-examination of the importance of primary, secondary, and branched plasmodesmata structure versus function. *Protoplasma* 248:61-74.
Cardi T et al. (2010) Chloroplasts as expression platforms for plant-produced vaccines. *Expert Rev. Vaccines* 9:893-911.
Carlsson J et al. (2008) Mitochondrial regulation of flower development. *Mitochondrion* 8:74-86.
Carrer H et al. (1990) Gentamycin resistance in *Nicotiana* conferred by AAC(3)-I, a narrow substrate specificity acetyl transferase. *Plant. Mol. Biol.* 17:301-303.
Chase C D (2007) Cytoplasmic male sterility: a window to the world of plant mitochondrial-nuclear interactions. *Trends Genet.* 23:81-90.
Chen L & Liu Y G (2013) Male Sterility and Fertility Restoration in Crops. *Annu. Rev. Plant Biol.* 65:579-606.
Cronn R et al. (2008) Multiplex sequencing of plant chloroplast genomes using Solexa sequencing-by-synthesis technology. *Nucleic Acids Res.* 36: e122.
Davila J I et al. (2011) Double-strand break repair processes drive evolution of the mitochondrial genome in *Arabidopsis*. *BMC Biol.* 9:64.
Davis C C et al. (2005) Gene transfer from a parasitic flowering plant to a fern. *Proc. R. Soc. B.* 272(1578): 2237-2242.
Davis C C & Wurdack K J (2004) Host-to-parasite gene transfer in flowering plants: phylogenetic evidence from Malpighiales. *Science* 305(5684):676-678.
Davis C C & Xi Z (2015) Horizontal gene transfer in parasitic plants. *Curr. Opin. Plant Biol.* 26:14-19.
Dawson R F (1942) Accumulation of nicotine in reciprocal grafts of tomato and tobacco. *Am. J. Bot.* 29(1):66-71.
DePristo M A et al. (2011) A framework for variation discovery and genotyping using next-generation DNA sequencing data. *Nat. Genet.* 43(5):491-498.
Dubey G P & Ben-Yehuda S (2011) Intercellular nanotubes mediate bacterial communication. *Cell* 144:590-600.
Ehlers K & Kollmann R (2001) Primary and secondary plasmodesmata: structure, origin, and functioning. *Protoplasma* 216:1-30.
Fejes E et al. P (1990) Extensive homologous chloroplast DNA recombination in the pt14 *Nicotiana* somatic hybrid. *Theor. Appl. Genet.* 79:28-32.

Fuentes I et al. (2014) Horizontal genome transfer as an asexual path to the formation of new species. *Nature* 511:232-235.

Gillman J D et al. (2009) Cytoplasmic male sterility in *Petunia*. In *Petunia* (Gerats, T. and Strommer, J. eds). New York: Springer Science+Business Media, LLC, pp. 107-129.

Glimelius K & Bonnett H T (1986) *Nicotiana* cybrids with *Petunia* chloroplasts. *Theor. Appl. Genet.* 72:794-798.

Gorguet B et al. (2005) Parthenocarpic fruit development in tomato. *Plant biology* 7:131-139.

Green M & Sambrook J (2012) *Molecular Cloning* (Cold Spring Harbor Laboratory Press, Cold Spring Harbor, N.Y.) 4th Edition Ed.

Gurdon C & Maliga P (2014) Two distinct plastid genome configurations and unprecedented intraspecies length variation in the accD coding region in *Medicago truncatula*. DNA Res. 21:417-427.

Hajdukiewicz P et al. (1994) The small, versatile pPZP family of *Agrobacterium* binary vectors for plant transformation. *Plant Mol. Biol.* 25:989-994.

Hanson M R & Bentolila S (2004) Interactions of mitochondrial and nuclear genes that affect male gametophyte development. *Plant Cell* 16 Suppl:S154-169.

Hanson M R & Sattarzadeh A (2011) Stromules: recent insights into a long neglected feature of plastid morphology and function. *Plant Physiol.* 155:1486-1492.

Huang C Y et al. (2003) Direct measurement of the transfer rate of chloroplast DNA into the nucleus. *Nature* 422:72-76.

Kahlau S et al. (2006) Sequence of the tomato chloroplast DNA and evolutionary comparison of solanaceous plastid genomes. *J. Mol. Evol.* 63:194-207.

Kanevski I et al. (1999) Plastome engineering of ribulose-1,5-bisphosphate carboxylase/oxygenase in tobacco to form a sunflower large subunit and a tobacco small subunit hybrid. *Plant Physiol.* 119:133-141.

Kittiwongwattana C et al. (2007) Plastid marker gene excision by the phiC31 phage site-specific recombinase. *Plant Mol. Biol.* 64:137-143.

Koyanagi M et al. (2005) Cell-to-cell connection of endothelial progenitor cells with cardiac myocytes by nanotubes: a novel mechanism for cell fate changes? *Circ. Res.* 96:1039-1041.

Krichevsky A et al. (2010) Autoluminescent plants. *PLoS One* 5: e15461.

Krogh A et al. (2001) Predicting transmembrane protein topology with a hidden Markov model: application to complete genomes. *J. Mol. Biol.* 305(3):567-580.

Kubo T & Newton K J (2008) Angiosperm mitochondrial genomes and mutations. *Mitochondrion* 8:5-14.

Li H & Durbin R (2009) Fast and accurate short read alignment with Burrows-Wheeler transform. *Bioinformatics* 25(14):1754-1760.

Logan D C (2007) The mitochondrial compartment. *J. Exp. Bot.* 58, 1225-1243.

Logan D C (2010) Mitochondrial fusion, division and positioning in plants. *Biochem. Soc. Trans.* 38(3):789-795.

Lohse M et al. (2013) OrganellarGenomeDRAW—a suite of tools for generating physical maps of plastid and mitochondrial genomes and visualizing expression data sets. *Nucleic Acids Res.* 41 (Web Server issue):W575-581.

Lucas W J et al. (2009) Plasmodesmata—bridging the gap between neighboring plant cells. *Trends Cell Biol.* 19:495-503.

Lutz K A & Maliga P (2007) Construction of marker-free transplastomic plants. *Curr. Opin. Biotechnol.* 18:107-114.

Lutz K A et al. (2006) Construction of marker-free transplastomic tobacco using the Cre-loxP site-specific recombination system. *Nat. Protocols* 1:900-910.

Maliga P & Bock R (2011) Plastid biotechnology: food, fuel and medicine for the 21st century. *Plant Physiol* 155: 1501-1510.

Maliga P & Svab Z (2011) Engineering the plastid genome of *Nicotiana sylvestris*, a diploid model species for plastid genetics *Plant Chromosome Engineering: Methods and Protocols*, Methods in Molecular Biology, ed Birchler J J (Springer Science+Business Media, LLC, New York), Vol 701:37-50.

McKenna A et al. (2010) The Genome Analysis Toolkit: a MapReduce framework for analyzing next-generation DNA sequencing data. *Genome Res.* 20(9):1297-1303.

Medgyesy P et al. (1985) Interspecific chloroplast recombination in a *Nicotiana* somatic hybrid. *Proc. Natl. Acad. Sci. USA* 82:6960-6964.

Medina M et al. (2013) Early anther ablation triggers parthenocarpic fruit development in tomato. *Plant Biotechnol. J* 11:770-779.

Melnyk C W et al. (2015) A Developmental Framework for Graft Formation and Vascular Reconnection in *Arabidopsis thaliana*. *Curr. Biol.* 25(10):1306-1318.

Miki B & McHugh S (2004) Selectable marker genes in transgenic plants: applications, alternatives and biosafety. *J. Biotechnol.* 107:193-232.

Molnar A et al. (2010) Small silencing RNAs in plants are mobile and direct epigenetic modification in recipient cells. *Science* 328:872-875.

Moon H S et al. (2008) Use of transferable *Nicotiana tabacum* L. microsatellite markers for investigating genetic diversity in the genus *Nicotiana*. *Genome* 51:547-559.

Mower J P et al. (2004) Plant genetics: gene transfer from parasitic to host plants. *Nature* 432(7014):165-166.

Mower J P (2005) PREP-Mt: predictive RNA editor for plant mitochondrial genes. *BMC Bioinformatics* 6:96.

Murray M G & Thompson W F (1980) Rapid isolation of high molecular weight plant DNA. *Nucleic Acids Res.* 8:4321-4325.

Niazi A K et al. (2013) Targeting nucleic acids into mitochondria: Progress and prospects. *Mitochondrion* 13:548-558.

Nivison H T & Hanson M R (1989) Identification of a mitochondrial protein associated with cytoplasmic male sterility in petunia. *Plant Cell* 1, 1121-1130.

Palmer J D (1983) Chloroplast DNA exists in two orientations. *Nature* 301:92-93.

Peres L E P et al. (2001) Shoot regeneration capacity from roots and transgenic hairy roots of tomato cultivars and wild relatives. *Plant Cell Tissue and Organ Culture* 65:37-44.

Preuten T et al. (2010) Fewer genes than organelles: extremely low and variable gene copy numbers in mitochondria of somatic plant cells. *Plant J.* 64:948-959.

Rice D W et al. (2013) Horizontal transfer of entire genomes via mitochondrial fusion in the angiosperm *Amborella*. *Science* 342(6165): 1468-1473.

Richardson A O & Palmer J D (2007) Horizontal gene transfer in plants. *J. Exp. Bot.* 58(1):1-9.

Ruf S et al. (2001) Stable genetic transformation of tomato plastids: foreign protein expression in fruit. *Nat. Biotechnol.* 19:870-875.

Ruf S & Bock R (2014) Plastid transformation in tomato. *Methods Mol. Biol.* 1132:265-276.

Rustom A et al. (2004) Nanotubular highways for intercellular organelle transport. *Science* 303:1007-1010.

Sanchez-Puerta M V et al. (2015) Homologous recombination and retention of a single form of most genes shape the highly chimeric mitochondrial genome of a cybrid plant. *New Phytol.* 206(1):381-396.

Sandhu A P et al. (2007) Transgenic induction of mitochondrial rearrangements for cytoplasmic male sterility in crop plants. *Proc. Natl. Acad. Sci. USA* 104:1766-1770.

Schmitz-Linneweber C et al. (2005) Pigment deficiency in nightshade/tobacco cybrids is caused by the failure to edit the plastid ATPase alpha-subunit mRNA. *Plant Cell* 17:1815-1828.

Sheahan M B et al. (2005) Mitochondria as a connected population: ensuring continuity of the mitochondrial genome during plant cell dedifferentiation through massive mitochondrial fusion. *Plant J.* 44:744-755.

Sheppard A E et al. (2008) Transfer of plastid DNA to the nucleus is elevated during male gametogenesis in tobacco. *Plant Physiol.* 148:328-336.

Simpson J T et al. (2009) ABySS: a parallel assembler for short read sequence data. *Genome Res.* 19(6):1117-1123.

Sinagawa-Garcia S R et al. (2009) Next generation synthetic vectors for transformation of the plastid genome of higher plants. *Plant Mol. Biol.* 70:487-498.

Stegemann S et al. (2003) High-frequency gene transfer from the chloroplast genome to the nucleus. *Proc. Natl. Acad. Sci. USA* 100:8828-8833.

Stegemann S et al. (2012) Horizontal transfer of chloroplast genomes between plant species. *Proc. Natl. Acad. Sci. USA* 109(7):2434-2438.

Stegemann S & Bock R (2009) Exchange of genetic material between cells in plant tissue grafts. *Science* 324:649-651.

Stonebloom S et al. (2009) Loss of the plant DEAD-box protein ISE1 leads to defective mitochondria and increased cell-to-cell transport via plasmodesmata. *Proc. Natl. Acad. Sci. USA* 106:17229-17234.

Sugiyama Y et al. (2005) The complete nucleotide sequence and multipartite organization of the tobacco mitochondrial genome: comparative analysis of mitochondrial genomes in higher plants. *Mol. Genet. Genomics* 272: 603-615.

Svab Z & Maliga P (2007) Exceptional transmission of plastids and mitochondria from the transplastomic pollen parent and its impact on transgene containment. *Proc. Natl. Acad. Sci. USA* 104:7003-7008.

Takenaka M et al. (2013) RNA editing in plants and its evolution. *Annu Rev Genet* 47:335-352.

Thyssen G et al. (2012) Cell-to-cell movement of plastids in plants. *Proc. Natl. Acad. Sci. USA* 109:2439-2443.

Tungsuchat-Huang T et al. (2011) Visual spectinomycin resistance gene for facile identification of transplastomic sectors in tobacco leaves. *Plant Mol. Biol.* 76:453-461.

Tungsuchat-Huang T & Maliga P (2012) Visual marker and *Agrobacterium*-delivered recombinase enable the manipulation of the plastid genome in greenhouse-grown tobacco plants. *Plant J.* 70:717-725.

Tungsuchat-Huang T & Maliga P (2014) Plastid marker gene excision in greenhouse-grown tobacco by *Agrobacterium*-delivered Cre recombinase In *Chloroplast Biotechnology* (Maliga, P. ed. New York: Springer Science+ Business Media, pp. 205-220.

Van der Auwera G A et al. (2013) From FastQ data to high confidence variant calls: the Genome Analysis Toolkit best practices pipeline. *Curr. Protoc. Bioinformatics* 11(1110):11.10.11-11.10.33.

Won H & Renner S S (2003) Horizontal gene transfer from flowering plants to Gnetum. *Proc. Natl. Acad. Sci. USA* 100(19):10824-10829.

Yoshimi M et al. (2013) Variations in the structure and transcription of the mitochondrial atp and cox genes in wild *Solanum* species that induce male sterility in eggplant (*S. melongena*). *Theor. Appl. Genet.* 126(7):1851-1859.

Young E G & Hanson M R (1987) A fused mitochondrial gene associated with cytoplasmic male sterility is developmentally regulated. *Cell* 50: 41-49.

Yukawa M et al. (2006) The chloroplast genome of *Nicotiana sylvestris* and *Nicotiana tomentosiformis*: complete sequencing confirms that the *Nicotiana sylvestris* progenitor is the maternal genome donor of *Nicotiana tabacum*. *Mol. Genet. Genomics* 275:367-373.

Zubko M K et al. (2004) Stable transformation of petunia plastids. *Transgenic Res.* 13: 523-530.

Zubko M K & Day A (1998) Stable albinism induced without mutagenesis: a model for ribosome-free plastid inheritance. *Plant J.* 15:265-271.

APPENDIX

TABLE S1

Plastid primers for testing ptDNA polymorphic sites between N. tabacum and N. undulate. From top to bottom, the sequences are SEQ ID NOs: 8-19.

| Pair | Primer | Position | Strand | Gene | Sequence |
| --- | --- | --- | --- | --- | --- |
| *1 | 12upF | 12907 | F | atfP | TCTTACTTAGAATAGGTCGTCGATTCAGCA |
| *1 | 14upR | 14098 | R | atfP | CCACTGATTTCTGCCGCTTCCGTT |
| *2 | 27upF | 27875 | F | rpoB-trnC | ACACATTCCAACCTGCTTGAATACCA |
| *2 | 29upR | 29210 | R | rpoB-trnC | TCTTCCGCCCCCTTCCACAACTAT |
| *3 | 48upF | 48971 | F | trnL | GAGACATTCCTCCGCTTTCAGGCG |
| *3 | 49upR | 49945 | R | trnL | TGGAACCGCTAAGGAAAGGGGGTC |
| *4 | 60upF | 60806 | F | accD | AACGGCATTCCCGTAGCAATTGGG |
| *4 | 62upR | 62222 | R | accD | GGATGAGATTGGGTCCCAGCGGAT |
| *5 | 83upF | 83888 | F | ndhF | TTTCCACCACGACGTGCATTTCGT |

TABLE S1-continued

Plastid primers for testing ptDNA polymorphic sites between *N. tabacum* and *N. undulate*. From top to bottom, the sequences are SEQ ID NOs: 8-19.

| Pair | Primer | Position | Strand | Gene | Sequence |
|---|---|---|---|---|---|
| *5 | 85upR | 85414 | R | ndhF | TACAAATTGCGGGGCGTATCGACG |
| *6 | 111upF | 111916 | F | ndhE-ndhG | TCGGAAGAAAGGTGGGATCCGGAC |
| *6 | 113upR | 113293 | R | ndhE-ndhG | TGGTATGGGGTCTTATCGAAGCGC |

TABLE S2

Mitochondrial primers for testing mtDNA polymorphic sites between *N. tabacum* and *N. undulata*. From top to bottom, the sequences are SEQ ID NOs: 20-31.

| Pair | Primer | Position | Strand | Gene | Sequence |
|---|---|---|---|---|---|
| 1 | mt-0-F | 690 | F | orf125a | CCCCGCCCAGTAGTGCCTCT |
| 1 | mt-4-R | 4334 | R | orf125a | CCGCGGGCATCGCGATAAGT |
| 2 | mt-100-F | 100070 | F | orf129b | CGGCCATCCTGGTCCTCAGGA |
| 2 | mt-104-R | 104811 | R | orf129b | TGGGGACTCGCACGAGGAGG |
| 3 | mt-180-F | 180316 | F | nad4 | GGCAGGAGCGCAACGACCTT |
| 3 | mt-183-R | 183813 | R | nad4 | AGTCGGGTTGCTCACGCAGC |
| 4 | mt-201-F | 201586 | F | nad2 | TGGTGTGCTTCCTGCTCGCG |
| 4 | mt-204-R | 204759 | R | nad2 | TTTCTCCGTGCCCGTTCCGC |
| 5 | mt-222-F | 222140 | F | nad5 | AGGTGCCCGTAGTAGGCCGG |
| 5 | mt-226-R | 226463 | R | nad5 | TTGGGCTTGGCTCTGCTCGC |
| 6 | mt-306-F | 306203 | F | orf115-ccmFc | CACGACTCCCCCTCTCCCCG |
| 6 | mt-309-R | 309623 | R | orf115-ccmFc | TGCCCGATTCCCCGACCCAT |

TABLE S3

Plastid primers for PCR amplification of the *Nicotiana tabacum* and *N. undulata* plastid genomes. From top to bottom, the sequences are SEQ ID NOs: 32-99.

| Pair | Primer | Position | Strand | Gene | Sequence |
|---|---|---|---|---|---|
| 1 | 0F | 14 | F | trnH | ACGGGAATTGAACCCGCGCA |
| 1 | 4R | 4410 | R | trnK | CGGGTTGCTAACTCAACGG |
| 2 | 3F | 3704 | F | trnK | TCAAATGATACATAGTGCGATACA |
| 2 | 8R | 8653 | R | trnS | CGAATCCCTCTCTTTCCG |
| 3 | 7F | 7989 | F | psbK | GCCTTTGTTTGGCAAGCTGCTGTAAG |
| 3 | 12R | 12042 | R | atpA | GGCATTGCTCGTATTCACGGTCTTG |
| 4 | 11F | 11052 | F | atpA | CCACTCTGGAAACGGAGATACCC |
| 4 | 16R | 16791 | R | rps2 | CTCGTTTTTTATCAGAAGCTTGTG |
| 5 | 15F | 15267 | F | atpI | GATGGCCCTCCATGGATTCACC |
| 5 | 20R | 20888 | R | rpoC2 | GAGGATTAATGTCAGATCCTCAAGG |

TABLE S3-continued

Plastid primers for PCR amplification of the *Nicotiana tabacum* and *N. undulata* plastid genomes. From top to bottom, the sequences are SEQ ID NOs: 32-99.

| Pair | Primer | Position | Strand | Gene | Sequence |
|---|---|---|---|---|---|
| 6 | 19F | 19971 | F | rpoC2 | GATAGACATCGGTACTCCAGTGC |
| 6 | 24R | 24612 | R | rpoB | GTTACACAACAACCCCTTAGAGG |
| 7 | 24F | 24069 | F | rpoC1 | GCACAAATTCCGCTTTTTATAGG |
| 7 | 29R | 29568 | R | ycf6 | GCCCAAGCAAGACTTACTATATCCAT |
| 8 | 28F | 28849 | F | trnC | CCAGTTCAAATCCGGGTGTC |
| 8 | 34R | 34493 | R | psbD | TACCAAGGGCTATAGTCAT |
| 9 | 33F | 33186 | F | trnT | GCCCTTTTAACTCAGTGGTA |
| 9 | 38R | 38115 | R | trnG | AACCCGCATCTTCTCCTTGG |
| 10 | 37F | 37147 | F | trnS | GAGAGAGAGGGATTCGAACC |
| 10 | 43R | 43484 | R | psaA | TTCGTTCGCCGGAACCAGAA |
| 11 | 41F | 41267 | F | psaA | AAGAATGCCCATGTTGTGGC |
| 11 | 46R | 46162 | R | ycf3 | CCTATTACAGAGATGGTGCGATTT |
| 12 | 45F | 45083 | F | ycf3 | CGATGCATATGTAGAAAGCC |
| 12 | 51R | 51022 | R | ndhJ | TTTTTATGAAATACAAGATGCTC |
| 13 | 49F | 49312 | F | trnL | CGAAATCGGTAGACGCTACG |
| 13 | 54R | 54971 | R | atpE | GAAGGAAGGAGACAAAAAATTGAGGC |
| 14 | 53F | 53776 | F | trnV | CGAACCGTAGACCTTCTCGG |
| 14 | 58R | 58198 | R | rbcL | GTAAAATCAAGTCCACCGCG |
| 15 | 57F | 57272 | F | atpB | TCTAGGATTTACATATACAACAT |
| 15 | 62R | 62754 | R | ycf4 | CTAATAAGAAGCCTAATGAACC |
| 16 | 61F | 61145 | F | accD | GCAGGTAAAAGAGTAATTGAAC |
| 16 | 66R | 66664 | R | psbL | TACTCATTTTTGTACTTGCTGT |
| 17 | 65F | 65219 | F | petA | GCATCTGTTATTTTGGCACA |
| 17 | 71R | 71704 | R | clpP | ACCATAGAAACGAAGGAACCCACT |
| 18 | 70F | 70727 | F | rps18 | GCTCGTATTTTATCTTTGTTACC |
| 18 | 76R | 76301 | R | psbB | CCCCTTGGACTGCTACGAAAAACACC |
| 19 | 74F | 74963 | F | psbB | TGCCTTGGTATCGTGTTCATAC |
| 19 | 78R | 78846 | R | petB | CCCAGAAATACCTTGTTTACG |
| 20 | 77F | 77212 | F | psbH | TGGGGAACTACTCCTTTGAT |
| 20 | 82R | 82676 | R | rps8 | CGAGGTATAATGACAGACCGAG |
| 21 | 81F | 81880 | F | rpl36 | ATTCTACGTGCACCCTTACG |
| 21 | 86R | 86576 | R | rps19 | GGGCATCTACCATTATACCC |
| 22 | 85F | 85864 | F | rps3 | AGTCTGAAACCAAGTGGATTATT |
| 22 | 89R | 89311 | R | YCF2 | GAAGATACAGGAGCGAAACAATCAAC |
| 23 | 88F | 88062 | F | rpl2 | GCTTATGACCTCCCCCTCTATGC |
| 23 | 93R | 93140 | R | YCF2 | TCTTCTAGAGAATCTCCTAATTGTTC |

TABLE S3-continued

Plastid primers for PCR amplification of the *Nicotiana tabacum* and *N. undulata* plastid genomes. From top to bottom, the sequences are SEQ ID NOs: 32-99.

| Pair | Primer | Position | Strand | Gene | Sequence |
|---|---|---|---|---|---|
| 24 | 91F | 91131 | F | YCF2 | CTTCGAATATGGAATTCAAAGGGATC |
| 24 | 97R | 97636 | R | ndhB | CTCAAACAAGCATGAAACGTATGC |
| 25 | 96F | 96469 | F | trnL | GAGATTTTGAGTCTCGCGTGTC |
| 25 | 100R | 100782 | R | rps12 | TCACTGCTTATATACCCGGTATTGGC |
| 26 | 99F | 99552 | F | rps7 | GTGCAAAAGCTCTATTTGCCTCTGCC |
| 26 | 104R | 104797 | R | oriA | ATCGAAAGTTGGATCTACATTGGATC |
| 27 | 103F | 103454 | F | rrn16 | CGACACTGACACTGAGAGACGAAAGC |
| 27 | 108R | 108280 | R | rrn23 | CGCTACCTTAGGACCGTTATAGTTAC |
| 28 | 107F | 107056 | F | rrn23 | GAAACTAAGTGGAGGTCCGAACCGAC |
| 28 | 111R | 111882 | R | ORF350 | AGTGGATCCCTCTTGTTCCTGTTTAG |
| 29 | 110F | 110672 | F | trnN | ACAGCCGACCGCTCTACCACTGAGC |
| 29 | 114R | 114269 | R | ndhF | GGATCATACCTTTCATTCCACTTCC |
| 30 | 113F | 113036 | F | ndhF | ATTTCATCTTTGGACCAAAAACAAGC |
| 30 | 119R | 119286 | R | psaC | GCTAAACAAATTGCTTCTGCTCC |
| 31 | 117F | 117227 | F | ycf5 | GGTCAATCTTTTAGGAATAGGGTTAC |
| 31 | 123R | 123506 | R | ndhA | GGACTTCTTATGTCGGGATATGGATC |
| 32 | 122F | 122194 | F | ndhA | CTGCGCTTCCACTATATCAACTGTAC |
| 32 | 128R | 128835 | R | ycf1 | TGAAACCTTGGCATATATCT |
| 33 | 127F | 127391 | F | ycf1 | AATTTCGAGGTTCTTATTTACT |
| 33 | 132R | 132957 | R | trnR | GACGATACTGTAGGGGAGGTC |
| 34 | 154F | 154629 | F | rpl2 | CCATAGAATACGACCCTAAT |
| 34 | 1R | 1533 | R | psbA | CTAGCACTGAAAACCGTCTT |

TABLE S4

Nuclear SSR Primers. From top to bottom, the sequences are SEQ ID NOs: 100-149.

| Chromosome | Primer | Strand | Sequence |
|---|---|---|---|
| 1 | PT30307 | F | AAAGAAGCACGGTCAAATAGG |
| 1 | PT30307 | R | GCAACAACAAGGTGTCATGG |
| 2 | PT30242 | F | TGTGTACTACCGGCCTACTGC |
| 2 | PT30242 | R | TTCTGCTAAACCGATCGTGG |
| 3b | PT30205 | F | GGTCGATCCACAATTTAAACG |
| 3b | PT30205 | R | GCACTTGCTCCTTTGTACCC |
| 4 | PT30272 | F | GAACCTAACCTCGCTCCACA |
| 4 | PT30272 | R | AAATGGTAGCTGCGAGGAGA |
| 5 | PT30471 | F | GTCTGTACCTTCGCCAAAGC |
| 5 | PT30471 | R | TCCTCAGAGAACTCCAGCGT |
| 6 | PT30087 | F | CTTCTTCCTAAGCCGAGGGT |
| 6 | PT30087 | R | TTGATGATAGAACGCAACTCG |
| 7 | PT30138 | F | AGTTGCAGGATTGTTCGCTT |
| 7 | PT30138 | R | CGACTGCAAGAGTTGGCAAT |
| 8a | PT30167 | F | TGATACAGAATATGGCGAACTTT |
| 8a | PT30167 | R | CCGCTTCATCATTGAGGTTT |
| 9 | PT30140 | F | AAGATGGCATATGGGATTGG |
| 9 | PT30140 | R | TGAATCGGAGGAAGTGAATG |

TABLE S4-continued

Nuclear SSR Primers. From top to bottom, the sequences are SEQ ID NOs: 100-149.

| Chromosome | Primer | Strand | Sequence |
|---|---|---|---|
| 10 | PT30482 | F | CTTCTCTCTCCACCGCAGAC |
| 10 | PT30482 | R | ACAGTTGGATATGGTGGCGT |
| 11 | PT30008 | F | CGTTGCTTAGTCTCGCACTG |
| 11 | PT30008 | R | GGTTGATCCGACACTATTACGA |
| 12 | PT30098 | F | TTGTTGCTCTCTCGAGTTCTTT |
| 12 | PT30098 | R | GCAGTCGACTCATTGGCA |
| 13 | PT30342 | F | GACAACAATCAGTAAAGGAAACGA |
| 13 | PT30342 | R | AATGCAAGACCCTGTCAACC |
| 13 | PT30420 | F | AACAAACCGCTTTCCATTCT |
| 13 | PT30420 | R | GAATTAGGCGCTTTGGGAAT |
| 14a | PT30175 | F | TTAGGCGGCGGTATTCTTAT |
| 14a | PT30175 | R | TATGCCTCAATCCCTTACGC |
| 15 | PT30463 | F | AAGCTGCCCTAGCTCAATCA |
| 15 | PT30463 | R | AACATCACCATTTCCACAAGTTT |
| 16 | PT30412 | F | CATTTAGCCGGGAACATTCA |
| 16 | PT30412 | R | CATGGGATACACACGCAAAG |
| 17 | PT30274 | F | TGACAGCTAAGCTAATAACAGTAAATG |
| 17 | PT30274 | R | GGACTTTGGAGTGTCAAATGC |
| 18 | PT30111 | F | AGCCAGCCACCAAATTTATC |
| 18 | PT30111 | R | GGAACATTGCTCAAGCCCTA |
| 19 | PT30230 | F | TTTCTTTCTGTCTGATGCTTCAAT |
| 19 | PT30230 | R | TTGTCCATCTCACTTGCTGC |
| 20 | PT20286 | F | ACGCTAGAGCATCCAACA |
| 20 | PT20286 | R | TAGTGAAAGGCAAGCAGG |
| 21 | PT30378 | F | TCAAATGAGGGTTGTAGCCA |
| 21 | PT30378 | R | TGCAATGGCTACACAAGAAGA |
| 22 | PT30168 | F | TTGAACACCAATTGCGGTAA |
| 22 | PT30168 | R | AAATTCTTGGGTCATGGTGG |
| 23 | PT30231 | F | AGGAGGCGAAGAAAGAGGAG |
| 23 | PT30231 | R | CCCATGAATTCGTAACAGCA |
| 24 | PT40024 | F | AATGTCTGCCCAATCGAAAG |
| 24 | PT40024 | R | CGAATAACGACACTCGAACG |

TABLE S5

24 regions polymorphic between *N. sylvestris* and *N. undulata* mtDNA tested in GT19. For primers amplifying the polymorphic loci and the detection of the polymorphisms see Table S6. *N. sylvestris* 12119 sequence is SEQ ID NO: 184; *N. sylvestris* 183624 sequence is SEQ ID NO: 185; and *N. sylvestris* 202061 sequence is SEQ ID NO: 186.

| Marker | Location in *N. sylvestris* mtDNA (KT997964) | *N. sylvestris* | *N. undulata* |
|---|---|---|---|
| Mito1 | 919 | A | G |
|  | 1017 | A | C |
|  | 1068 | T | C |
|  | 1320 | G | T |
|  | 1342 | A | AT |
|  | 1376 | C | T |
|  | 1565 | G | C |
| Mito2 | 3537 | C | T |
|  | 3573 | G | C |
| Mito3 | 12119 | CTTATTGACTCAAG | C |
| Mito4 | 45658 | T | C |
|  | 45661 | T | C |
|  | 45662 | G | T |
| Mito5 | 64783 | T | G |
| Mito6 | 77532 | A | G |
| Mito7 | 100408 | A | C |
|  | 100521 | G | C |
|  | 100811 | G | T |
| Mito8 | 131664 | C | A |
|  | 131687 | G | GC |
|  | 131756 | C | A |
|  | 131873 | T | C |
|  | 131911 | G | T |
|  | 131912 | T | G |
|  | 131945 | T | C |
|  | 132094 | C | T |
|  | 132126 | T | G |
|  | 132279 | C | T |
|  | 132296 | T | A |
| Mito9 | 137888 | G | GA |
|  | 138002 | C | G |
|  | 138019 | G | C |
|  | 138049 | T | C |
| Mito10 | 147418 | A | C |
| Mito11 | 158825 | CTATCAACA | C |
|  | 158866 | T | TAAAA |
|  | 158869 | C | A |
|  | 158888 | A | G |
|  | 158898 | G | A |
|  | 158928 | G | C |
|  | 158938 | C | A |
|  | 159014 | G | A |
|  | 159019 | T | C |
| Mito12 | 173856 | A | G |
| Mito13 | 183624 | CCTCCGTACAA | C |
| Mito14 | 202061 | AGTTTCCGGCT | A |
|  | 202500 | C | T |
|  | 202508 | T | G |
| Mito15 | 203240 | A | T |
| Mito16 | 220947 | T | C |

TABLE S5-continued 24 regions polymorphic between *N. sylvestris* and *N. undulata* mtDNA tested in GT19. For primers amplifying the polymorphic loci and the detection of the polymorphisms see Table S6. *N. sylvestris* 12119 sequence is SEQ ID NO: 184; *N. sylvestris* 183624 sequence is SEQ ID NO: 185; and *N. sylvestris* 202061 sequence is SEQ ID NO: 186.

| Marker | Location in *N. sylvestris* mtDNA (KT997964) | *N. sylvestris* | *N. undulata* |
|---|---|---|---|
| Mito17 | 270455 | G | A |
|  | 270504 | T | A |
| Mito18 | 306929 | T | C |
|  | 307041 | C | A |
| Mito19 | 309810 | A | G |
|  | 309931 | G | A |
|  | 310082 | T | A |
| Mito20 | 328112 | T | G |
|  | 328113 | C | A |
|  | 328151 | C | T |
|  | 328420 | A | C |
|  | 328427 | G | T |
|  | 328953 | A | G |
| Mito21 | 356531-356542 | 112 nt | deletion |
| Mito22 | 361006 | C | A |
|  | 361007 | T | C |
|  | 361695 | T | G |
| Mito23 | 381868 | G | G |
| Mito24 | 393353 | C | G |
|  | 393363-393517 | 145 nt | deletion |

TABLE S6

977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
|---|---|---|---|---|---|
| 556 | T | A | 15432 | G | T |
| 919 | A | G | 15757 | T | A |
| 1017 | A | C | 16223 | A | AAGCG |
| 1068 | T | C | 22204 | T | C |
| 1320 | G | T | 22480 | ATTCT | A |
| 1342 | A | AT | 22530 | G | T |
| 1376 | C | T | 22773 | G | T |
| 1565 | G | C | 22774 | A | C |
| 2246 | A | C | 23137 | A | T |
| 2397 | C | T | 23155 | A | T |
| 2464 | G | T | 23156 | A | T |
| 2465 | A | C | 23611 | T | C |
| 2688 | A | G | 23744 | G | T |
| 2825 | T | G | 23923 | A | C |
| 3191 | C | G | 24077 | A | ATCCCG |
| 3537 | C | T | 24214 | T | C |
| 3573 | G | C | 24409 | C | T |
| 4507 | T | C | 24610 | G | T |
| 5501 | C | T | 25349 | A | G |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
| --- | --- | --- | --- | --- | --- |
| 6401 | A | C | 36874 | A | G |
| 10181 | TCTTC | T | 37196 | C | T |
| 10185 | C | CGGGA | 37202 | A | T |
| 11868 | G | C | 37325 | G | T |
| 12050 | C | A | 37689 | G | C |
| 12119 (187) | CTTATTGACTCAAG | C | 37980 | C | A |
| 12495 | A | C | 37991 | A | C |
| 13010 | T | A | 38622 | C | A |
| 13011 | T | G | 38629 | T | G |
| 13027 | A | C | 38630 | A | C |
| 13059 | T | C | 39321 | G | T |
| 13164 | A | C | 39654 | C | A |
| 13168 | A | C | 39749 | G | A |
| 14972 | A | G | 40060 | A | T |
| 15080 | T | G | 40691 | TAA | T |
| 15364 | G | T | 40694 | T | TCA |
| 42342 | T | A | 64783 | T | G |
| 42343 | T | G | 65279 | T | A |
| 43413 | C | A | 65337 | CTTG | C |
| 43480 | C | A | 65341 | A | AGTC |
| 43878 | A | T | 65781 | C | G |
| 43976 | G | A | 74206 | G | A |
| 44227 | G | T | 74562 | C | T |
| 44413 | G | T | 74582 | CCCCT | C |
| 44443 | T | A | 74693 | C | G |
| 44454 | T | C | 74699 | A | G |
| 45020 | C | A | 74709 | G | T |
| 45276 | C | G | 74713 | A | G |
| 45658 | T | C | 74715 | A | G |
| 45661 | T | C | 74718 | T | C |
| 45662 | G | T | 74725 | C | G |
| 45962 | G | C | 74728 | T | C |
| 45968 | T | G | 74743 | T | A |
| 45969 | T | C | 74745 | T | C |
| 45993 | A | T | 74751 | G | A |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
|---|---|---|---|---|---|
| 46013 | G | C | 74752 | C | T |
| 46189 | C | A | 74764 | T | C |
| 47332 | A | G | 74767 | A | T |
| 47335 | C | A | 74769 | G | A |
| 47569 | T | G | 74778 | G | T |
| 47570 | C | A | 74788 | G | T |
| 48362 | T | C | 74803 | T | G |
| 48471 | T | TGCAA | 74806 | T | C |
| 48634 | G | A | 74813 | T | A |
| 48636 | G | A | 74818 | T | C |
| 48865 | G | T | 74821 | T | C |
| 48965 | CT | C | 74822 | G | T |
| 48967 | AT | A | 74823 | A | C |
| 48969 | G | GAA | 74843 | T | C |
| 49304 | C | T | 74871 | T | G |
| 50084 | T | A | 74878 | T | C |
| 50416 | C | A | 74879 | T | C |
| 50839 | G | T | 74882 | G | A |
| 51051 | TG | T | 74883 | G | C |
| 51189 | A | C | 74897 | T | C |
| 51193 | T | G | 74956 | G | C |
| 51218 | TACTAC | T | 74983 | C | T |
| 51243 | C | A | 74985 | A | G |
| 64141 | C | T | 74992 | T | C |
| 74995 | C | A | 85657 | G | T |
| 74996 | C | A | 85664 | C | T |
| 75006 | T | C | 85675 | G | A |
| 75019 | T | G | 85678 | C | A |
| 75025 | T | C | 85690 | G | C |
| 75037 | C | T | 85694 | A | G |
| 75042 | G | C | 85699 | G | T |
| 75054 | G | A | 85715 | A | C |
| 75065 | A | C | 85744 | G | C |
| 75078 (188) | GGGGTGTCAC | G | 85856 | G | A |
| 75100 | T | C | 85858 | G | A |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
|---|---|---|---|---|---|
| 76371 | C | T | 85886 | G | T |
| 76798 | A | T | 85910 | C | T |
| 76827 | T | A | 85969 | C | T |
| 77135 | T | C | 86026 | A | C |
| 77147 | T | A | 86091 | T | G |
| 77157 | G | C | 86171 | G | C |
| 77160 | G | T | 86216 | C | G |
| 77195 | T | C | 86272 | GA | A |
| 77230 (189) | AGAAAAATCCC | A | 86285 | G | C |
| 77416 | C | G | 86296 | A | G |
| 77532 | A | G | 86299 | C | G |
| 77721 | C | G | 86306 | T | A |
| 78733 | G | T | 87320 | C | CTCTTTCT |
| 79092 | G | A | 87322 | A | G |
| 81861 | A | G | 87324 | CCAAGAAA | C |
| 83701 | C | A | 87332 | G | T |
| 83703 | T | G | 87435 | C | T |
| 84148 | C | G | 87504 | A | C |
| 84649 | A | T | 87767 | GA | G |
| 84773 | G | A | 87802 | G | A |
| 84819 | A | T | 87885 | T | A |
| 84824 | T | G | 87886 | T | G |
| 84966 | A | C | 88120 | C | A |
| 84972 | G | A | 88128 | A | C |
| 85240 | C | T | 88335 | GA | G |
| 85366 | T | G | 88629 | A | C |
| 85369 | C | T | 89365 | T | G |
| 85599 | A | G | 89374 | T | G |
| 85630 | G | A | 89466 | C | CT |
| 85637 | T | G | 90115 | A | G |
| 85639 | C | A | 92330 | A | C |
| 91251 | T | G | 92589 | C | T |
| 92905 | A | C | 115365 | C | A |
| 93859 | T | G | 118357 | C | T |
| 93882 | G | C | 120537 | C | A |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
|---|---|---|---|---|---|
| 95275 | C | CA | 120919 | C | G |
| 96912 | T | A | 120934 | G | T |
| 99380 | G | C | 120935 | A | C |
| 100408 | A | C | 120945 | G | T |
| 100521 | G | C | 121543 | G | C |
| 100811 | G | T | 122149 | T | C |
| 103829 | A | C | 122385 | T | A |
| 104624 | G | T | 122533 | C | A |
| 105527 | C | G | 123326 | C | A |
| 105720 | A | C | 123328 | T | G |
| 105834 | TTTC | T | 123333 | T | A |
| 107092 | T | C | 124966 | T | C |
| 107317 | G | C | 125774 | C | T |
| 107380 | C | G | 126117 | A | C |
| 109046 | G | C | 127188 | GGGCTT | G |
| 110758 | A | C | 127491 | T | G |
| 113763 | G | C | 127824 | T | C |
| 113931 | T | G | 128401 | T | G |
| 114285 | C | A | 128402 | A | T |
| 115074 | G | T | 128403 | A | C |
| 115080 | C | T | 128436 | A | C |
| 115086 | G | T | 128520 | C | G |
| 115089 | T | C | 128656 | T | G |
| 115096 | G | A | 128860 | T | G |
| 115116 | A | C | 131664 | C | A |
| 115162 | C | G | 131687 | G | GC |
| 115172 | C | T | 131756 | C | A |
| 115179 | G | A | 131873 | T | C |
| 115185 | C | G | 131911 | G | T |
| 115191 | T | C | 131912 | T | G |
| 115213 | T | C | 131945 | T | C |
| 115230 | C | CAA | 132094 | C | T |
| 115231 | TTC | T | 132126 | T | G |
| 115238 | G | T | 132279 | C | T |
| 115242 | A | T | 132296 | T | A |
| 115245 | G | T | 133740 | C | A |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
|---|---|---|---|---|---|
| 115257 | T | C | 134302 | G | C |
| 115269 | G | A | 134803 | C | T |
| 115291 | A | C | 134945 | C | G |
| 115314 | T | G | 134960 | G | A |
| 134965 | G | GT | 147254 | G | T |
| 135353 | G | A | 147418 | A | C |
| 135505 | C | T | 147506 | G | T |
| 135740 | G | T | 147737 | G | T |
| 136004 | G | C | 148914 | C | A |
| 136545 | C | T | 148922 | G | T |
| 136546 | A | T | 148930 | CTTTTCT | C |
| 136547 | A | T | 148959 | C | G |
| 136603 | G | C | 152638 | A | T |
| 136658 | A | C | 153204 | C | T |
| 136722 | A | C | 153944 | A | G |
| 136724 | A | T | 155628 | C | A |
| 136737 | T | G | 156314 | T | G |
| 137385 | G | A | 156629 | C | T |
| 137773 | G | T | 157416 | GA | G |
| 137888 | G | GA | 157532 | T | A |
| 138002 | C | G | 158128 | A | G |
| 138019 | G | C | 158825 | CTATCAACA | C |
| 138049 | T | C | 158866 | T | TAAAA |
| 138334 | T | C | 158869 | C | A |
| 138381 | G | T | 158888 | A | G |
| 138382 | G | T | 158898 | G | A |
| 138513 | T | C | 158928 | G | C |
| 138698 | G | GT | 158938 | C | A |
| 139284 | T | TA | 159014 | G | A |
| 139814 | A | C | 159019 | T | C |
| 139817 | C | T | 164754 | G | T |
| 140021 | A | C | 165202 | G | T |
| 141162 | A | T | 166740 | G | T |
| 141471 | C | A | 166741 | A | T |
| 142690 | C | G | 167125 | T | G |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
|---|---|---|---|---|---|
| 143530 | TTAA | T | 167324 | T | A |
| 143535 | T | TTTA | 167325 | T | A |
| 144860 | T | C | 167390 | G | T |
| 145031 | C | A | 167391 | A | C |
| 145158 | C | A | 167392 | A | C |
| 145159 | C | G | 167397 | C | G |
| 145248 | C | T | 167757 | A | G |
| 145307 | C | T | 168068 | A | T |
| 145398 | GAAAA | G | 168090 | A | G |
| 145410 | G | C | 169869 | G | T |
| 145518 | C | G | 169870 | A | C |
| 146886 | G | T | 170057 | A | AAAGCTG |
| 170361 | G | C | 191192 | G | GA |
| 171179 | C | A | 192032 | T | C |
| 171401 | G | A | 193833 | T | A |
| 171862 | T | G | 196742 | C | A |
| 171863 | T | A | 196749 | T | C |
| 171864 | C | A | 196750 | G | T |
| 173487 | C | A | 196866 | T | A |
| 173856 | A | G | 197140 | A | AAGCTT |
| 174390 | G | C | 197731 | G | C |
| 175608 | T | A | 199029 | G | T |
| 176570 | A | T | 199770 | G | T |
| 178117 | A | T | 200167 | C | G |
| 178180 | G | C | 202061 (192) | AGTTTCCGGCT | A |
| 178413 | T | A | 202500 | C | T |
| 178414 | T | G | 202508 | T | G |
| 178464 | G | T | 203240 | A | T |
| 178556 | A | C | 203831 | G | A |
| 178610 | T | G | 204071 | T | A |
| 178897 | C | G | 204649 | T | G |
| 179184 | AAT | A | 204655 | T | A |
| 179189 | TA | T | 204947 | T | G |
| 179200 | A | ATAT | 204953 | T | G |
| 179205 | A | T | 205379 | A | G |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
|---|---|---|---|---|---|
| 179370 | T | G | 205395 | A | G |
| 179406 | G | T | 206021 | A | T |
| 179754 | A | G | 220947 | T | C |
| 179906 | G | T | 221614 | A | C |
| 180064 | C | CG | 221626 | G | C |
| 180066 | AC | A | 222498 | G | T |
| 181229 | T | C | 222499 | A | C |
| 181244 | C | T | 222625 | T | G |
| 182122 | A | C | 223529 | G | C |
| 182130 | T | G | 223578 | A | T |
| 183624 (190) | CCTCCGTACAA | C | 224298 | A | G |
| 185164 | C | A | 225494 | G | C |
| 185902 | A | G | 225934 | T | G |
| 185903 | A | C | 228791 | G | T |
| 185904 | A | G | 228951 | A | ATT |
| 186256 | A | C | 228953 | A | ATTAAT |
| 186626 | T | C | 228967 | A | AG |
| 187236 | G | C | 229400 | G | T |
| 191046 | G | A | 231274 | G | GA |
| 191132 | G | C | 231343 | T | G |
| 232131 (191) | GGGAATGAGT | G | 261163 | A | G |
| 232436 | G | A | 261170 | A | G |
| 234144 | G | A | 261178 | C | T |
| 234241 | G | T | 261182 | C | A |
| 234583 | C | G | 261201 | T | C |
| 235095 | A | T | 261277 | G | T |
| 235532 | G | C | 261403 | G | A |
| 236095 | G | T | 262285 | G | A |
| 236207 | T | A | 263021 | GA | G |
| 237654 | G | T | 264899 | G | C |
| 237736 | T | G | 267041 | G | C |
| 237875 | T | TA | 267925 | T | C |
| 237892 | T | C | 269292 | C | G |
| 237940 | C | G | 269642 | C | T |
| 238173 | A | C | 269860 | C | A |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
|---|---|---|---|---|---|
| 238346 | T | A | 270455 | G | A |
| 238357 | C | T | 270504 | T | A |
| 257920 | T | A | 271378 | A | C |
| 258493 | G | A | 271561 | C | A |
| 258575 | A | T | 272874 | T | TG |
| 258576 | A | C | 277875 | T | A |
| 258673 | C | A | 272940 | A | T |
| 258809 | A | AG | 272948 | T | G |
| 259209 | G | A | 272973 | C | T |
| 259970 | A | G | 272974 | T | A |
| 260011 | T | C | 273158 | G | T |
| 260130 | T | A | 273234 | T | G |
| 260446 | C | T | 273243 | T | G |
| 260551 | G | T | 273244 | T | A |
| 260561 | T | G | 273245 | C | A |
| 260636 | A | G | 273853 | G | A |
| 260669 | C | A | 274224 | T | A |
| 260769 | C | A | 274254 | G | T |
| 260918 | G | A | 275400 | C | G |
| 260920 | T | C | 276380 | T | G |
| 260946 | C | A | 277871 | C | T |
| 260971 | A | C | 278298 | A | T |
| 260977 | T | G | 278327 | T | A |
| 261024 | G | A | 278635 | T | C |
| 261074 | T | A | 278647 | T | A |
| 261075 | T | A | 278657 | G | C |
| 261076 | T | A | 278660 | G | T |
| 261153 | T | C | 278695 | T | C |
| 278730 (193) | AGAAAAATCCC | A | 287772 | GA | G |
| 278916 | C | G | 287785 | G | C |
| 279032 | A | G | 287796 | A | G |
| 279221 | C | G | 287799 | C | G |
| 280233 | G | T | 287806 | T | A |
| 280592 | G | A | 288274 | T | G |
| 283361 | A | G | 288363 | A | AT |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in N. sylvestris mtDNA | N. sylvestris | N. undulata | Location in N. sylvestris mtDNA | N. sylvestris | N. undulata |
|---|---|---|---|---|---|
| 285201 | C | A | 288437 | GA | G |
| 285203 | T | G | 288994 | C | T |
| 285648 | C | G | 289178 | A | C |
| 286149 | A | T | 289415 | G | GA |
| 286273 | G | A | 289940 | ATTT | A |
| 286319 | A | T | 289946 | T | TGA |
| 286324 | T | G | 290993 | G | C |
| 286466 | A | C | 291360 | T | TGG |
| 286472 | G | A | 291361 | CTA | C |
| 286740 | C | T | 292398 | G | T |
| 286866 | T | G | 293568 | T | A |
| 286869 | C | T | 293621 | A | C |
| 287099 | A | G | 294579 | G | T |
| 287130 | G | A | 295374 | A | G |
| 287137 | T | G | 297938 | A | C |
| 287139 | C | A | 297949 | A | G |
| 287157 | G | T | 298099 | G | T |
| 287164 | C | T | 298332 (194) | GGCTCCTCTGCTTACAGTCAAGTGGCTTTCA | G |
| 287175 | G | A | 298739 | A | T |
| 287178 | C | A | 298740 | A | T |
| 287190 | G | C | 298959 | A | G |
| 287194 | A | G | 299033 | C | A |
| 287199 | G | T | 299733 | A | C |
| 287215 | A | C | 300153 | A | T |
| 287244 | G | C | 300154 | A | T |
| 287356 | C | A | 300155 | A | C |
| 287359 | G | A | 300390 | A | C |
| 287386 | C | T | 300628 | G | C |
| 287410 | C | T | 301372 | G | T |
| 287469 | C | T | 301384 | A | T |
| 287526 | A | C | 301553 | C | T |
| 287591 | G | C | 301753 | A | T |
| 287671 | G | C | 301812 | A | C |
| 287716 | C | G | 302062 | C | T |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
|---|---|---|---|---|---|
| 302170 | A | T | 315487 | G | T |
| 302283 | GT | G | 315619 | CT | C |
| 302422 | T | G | 315957 | A | G |
| 302633 | T | A | 316100 | CT | C |
| 303031 | A | T | 316340 | AG | A |
| 303091 | C | CAAA | 325202 | A | C |
| 303358 | T | G | 327077 | A | C |
| 303372 | TTTTA | T | 327729 | AT | A |
| 303376 | A | AGGGG | 327809 | C | A |
| 303381 | A | C | 328112 | T | G |
| 303585 | A | G | 328113 | C | A |
| 304344 | C | G | 328151 | C | T |
| 304526 | G | C | 328420 | A | C |
| 304548 | A | T | 328427 | G | T |
| 304952 | C | G | 328953 | A | G |
| 305321 | G | T | 329512 | G | C |
| 305513 | C | A | 331167 | T | A |
| 305822 | G | C | 331226 | T | G |
| 306929 | T | C | 331943 | C | CCTGTG |
| 307041 | C | A | 332281 | A | T |
| 308001 | C | T | 332289 | T | A |
| 398267 | c | T | 337380 | A | G |
| 308534 | CGGAAT | C | 332663 | A | C |
| 308601 | A | G | 333637 | C | G |
| 309810 | A | G | 334395 | CG | C |
| 309931 | G | A | 337417 | G | T |
| 310082 | T | A | 340216 | A | G |
| 310494 | T | A | 340423 | C | A |
| 310528 | T | C | 341820 | T | A |
| 310529 | G | T | 349854 | C | T |
| 310530 | A | C | 349855 | G | T |
| 310644 | G | A | 349858 | G | A |
| 310708 | T | C | 350056 | C | CT |
| 311766 | T | A | 351596 | G | C |
| 311774 | C | A | 351618 | A | T |
| 312065 | CA | C | 352640 | T | A |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
|---|---|---|---|---|---|
| 312214 | C | T | 352937 | C | G |
| 312644 | T | G | 357980 | G | A |
| 312645 | A | C | 353341 | G | T |
| 313178 | G | T | 353342 | A | C |
| 313179 | C | A | 353513 | G | T |
| 313710 | A | T | 354276 | G | T |
| 314964 | T | C | 354277 | A | T |
| 354614 | C | A | 374455 | T | TCCCCTCTCCTCTGAGGCCGATCGCATCCACTTTTGGAG (195) |
| 354653 | G | T | 376294 | T | A |
| 354654 | A | C | 376333 | A | G |
| 354722 | T | C | 376366 | A | G |
| 354778 | C | G | 378825 | GA | G |
| 354914 | T | G | 379771 | T | G |
| 355054 | T | C | 379787 | G | T |
| 355072 | A | AAAGCT | 381615 | T | A |
| 357558 | G | A | 381868 | G | T |
| 357955 | T | G | 389233 | G | C |
| 357982 | C | T | 389387 | A | T |
| 358836 | G | C | 389596 | T | C |
| 359231 | G | A | 389706 | A | T |
| 359880 | C | G | 389711 | A | T |
| 360136 | T | A | 389714 | T | G |
| 360137 | T | A | 389733 | CTATAAT | C |
| 361006 | C | A | 389773 | C | CATAG |
| 361007 | T | C | 389797 | GTGCT | G |
| 361695 | T | G | 389811 | T | G |
| 362072 | T | A | 389839 | A | C |
| 362774 | A | G | 389857 | A | C |
| 363095 | G | C | 389865 | T | A |
| 364053 | T | C | 389884 | G | T |
| 364151 | G | T | 389989 | T | C |
| 364375 | T | G | 390056 | G | C |
| 364687 | G | C | 390144 | T | G |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
| --- | --- | --- | --- | --- | --- |
| 364791 | T | G | 390199 | T | C |
| 364834 | G | A | 390245 | G | T |
| 365027 | AG | A | 390402 | GA | G |
| 366455 | T | C | 390407 | GAAAT | G |
| 366626 | G | T | 390454 | T | C |
| 367842 | C | G | 390471 | C | T |
| 368823 | A | C | 390509 | A | C |
| 369113 | G | C | 390600 | A | G |
| 370686 | G | T | 390627 | C | T |
| 370868 | G | T | 390781 (196) | GACCTTCTTTCTAGCCTTTTAT | G |
| 370916 | T | A | 390806 | T | G |
| 372027 | T | G | 390943 | C | CTTATG |
| 373823 | A | G | 391084 | A | G |
| 373928 | G | C | 391143 | A | G |
| 391168 | T | c | 395845 | G | C |
| 391252 | C | A | 396314 | CG | C |
| 391261 | G | A | 396565 | G | C |
| 391267 | T | G | 396589 | T | G |
| 391369 | G | T | 396590 | C | A |
| 391445 | T | A | 396637 | T | G |
| 391446 | C | A | 396993 | T | G |
| 391464 | ACCCCGTC | A | 398925 | C | G |
| 391474 (197) | ACGAGCGGAGG | A | 399878 | T | G |
| 391486 | A | AATT | 399879 | A | C |
| 391551 | G | C | 399880 | T | A |
| 391664 | A | C | 399991 | T | G |
| 391700 | A | G | 400306 | A | C |
| 391799 | C | CCTTCTT | 400344 | G | T |
| 391809 | C | AG | 400523 | T | G |
| 392094 (198) | AATATCATAAAGCAAC | A | 400702 | C | A |
| 392184 | G | C | 400904 | A | T |
| 392250 | T | G | 400985 | T | G |
| 392251 | T | A | 401165 | G | T |
| 392278 | T | C | 401453 | A | G |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
|---|---|---|---|---|---|
| 392324 | T | C | 401460 | C | T |
| 392353 | G | C | 401577 | T | C |
| 392388 | A | C | 401626 | G | T |
| 392485 | T | C | 401627 | A | C |
| 392492 | A | C | 401725 | T | G |
| 392589 | G | T | 401727 | A | C |
| 392682 | T | A | 401858 | C | A |
| 392716 | C | A | 401862 | C | A |
| 392826 | T | C | 401935 | T | C |
| 392836 | G | GTTCGCC | 401949 | AGTCCTCGATTCG | A |
| 392871 | CATATG | C | 403680 | A | G |
| 392878 | T | G | 403796 | G | A |
| 392931 | T | C | 403853 | C | G |
| 392971 | T | A | 414891 | C | T |
| 393005 | G | C | 415533 | T | G |
| 393129 | T | TATATA | 416029 | T | A |
| 393142 | A | C | 416087 | CTTG | C |
| 393160 | A | C | 416091 | A | AGTC |
| 393353 | C | G | 416531 | C | G |
| 395269 | C | G | 424956 | A | G |
| 395427 | G | A | 425312 | C | T |
| 425332 | CCCCT | C | 425804 | G | A |
| 425443 | C | G | 425815 | A | C |
| 425449 | A | G | 425828 | GGGGTGTCAC (200) | G |
| 425459 | G | T | 425850 | T | C |
| 425463 | A | G | 427121 | C | T |
| 425465 | A | G | 427548 | A | T |
| 425468 | T | C | 427577 | T | A |
| 425475 | C | G | 427885 | T | C |
| 425478 | T | C | 427897 | T | A |
| 425493 | T | A | 427907 | G | C |
| 425495 | T | C | 427910 | G | T |
| 425501 | G | A | 427945 | T | C |
| 425502 | C | T | 427980 | AGAAAAATCCC (201) | A |

TABLE S6-continued 977 markers distinguishing *N. sylvestris* mtDNA from *N. undulata* mtDNA are shown. Marker locations are based on the mtDNA (KT997964). SEQ ID NOs are provided in parentheses.

| Location in *N. sylvestris* mtDNA | *N. sylvestris* | *N. undulata* | Location in *N. sylvestris* mtDNA | *N. sylvestris* | *N. undulata* |
|---|---|---|---|---|---|
| 425514 | T | C | 428166 | C | G |
| 425517 | A | T | 428282 | A | G |
| 425519 | G | A | 428471 | C | G |
| 425528 | G | T | 429483 | G | T |
| 425538 | G | T | 429842 | G | A |
| 425553 | T | G | | | |
| 425556 | T | C | | | |
| 425563 | T | A | | | |
| 425568 | T | C | | | |
| 425571 | T | C | | | |
| 425572 | G | T | | | |
| 425573 | A | C | | | |
| 425593 | T | C | | | |
| 425621 | T | G | | | |
| 425628 | T | C | | | |
| 425629 | T | C | | | |
| 425632 | G | A | | | |
| 425633 | G | C | | | |
| 425647 | T | C | | | |
| 425706 | G | C | | | |
| 425733 | C | T | | | |
| 425735 | A | G | | | |
| 425742 | T | C | | | |
| 425745 | C | A | | | |
| 425746 | C | A | | | |
| 425756 | T | C | | | |
| 425769 | T | G | | | |
| 425775 | T | C | | | |
| 425787 | C | T | | | |
| 425792 | G | C | | | |

TABLE S7

Primers for Northern blot probes 1-6, their location in the A. sylvestris mtDNA, and their relative location in the N. undulata mtDNA region carrying orf293 (part of this region is deposited in NCBI GenBank as KU180495). From top to bottom, the provided sequences are SEQ ID NOs: 202-213.

| Probe Number | Probe Size (nt) | Primer Name | Location in N. sylvestris mtDNA (KT997964) | Relative location in N. undulata | Primer Sequence |
|---|---|---|---|---|---|
| 1 | 413 | 390494R | 390494 | 1 | AGTGATCTCACTCCACGCATTG |
|   |   | 390077F | 390077 | 413 | TTCCGTGAGTTTAGACGGAAGC |
| 2 | 458 | 389973R | 389973 | 517 | ACAGTTTCACCGGATTGCAGG |
|   |   | 5422F | no homology | 974 | GTTCTTTCGCGCACTGAGTTAC |
| 3 | 494 | orf293-F1 | no homology | 1192 | TCGTAGAAATCGTTTTCGTTTGAATC |
|   |   | orf293-R1 | 324706, partial homology | 1685 | AGCATGAATGCCTTTTCTCACGG |
| 4 | 394 | 262380F | 262380 | 3104 | GACCTGCGATTAACGTCGGC |
|   |   | 262773R | 262773 | 3497 | TCCATCTTTCTTTCGTTAGTTAAGCC |
| 5 | 405 | 262897F | 262897 | 3621 | AGGACGAGTGTCCTACCTAATTCA |
|   |   | 263302R | 263302 | 4025 | ATCTTGGCCAAATGCCAATCCT |
| 6 | 391 | 263429F | 263429 | 4152 | ATTCCTGGAGTCCTACGCTACG |
|   |   | 263819R | 263819 | 4542 | TTATTCACTTGTGCTGGTGGCG |

TABLE S8

Deletions in N. undulata compared to N. sylvestris. Shown are 34 different deletions in N. undulata compared to N. sylvestris, and the origin of these regions in two recombinant fertile (RF1, RF2) and two CMS (RS3, RS4) offspring of GT19-C. 109,493 bp unique DNA sequence is missing from the N. undulata mtDNA compared to the N. sylvestris mtDNA. The deletions are associated with rearrangements in N. undulata compared to the N. sylvestris mtDNA structure apart from D20, D25 and D28. D6 coexists in RF1, RF2, RS3, and RS4 with a deletion-free N. sylvestris-derived homolog. D28 coexists in RS3 and RS4 with a minority deletion-free N. sylvestris-derived homolog. D29 and D30 exist in all four recombinants together with a minority deletion-free N. sylvestris-derived homolog. The location of deletions is given in the N. sylvestris mtDNA (KT997964).

| Deletion number | Deletion size (bp) | Deletion start | Deletion end | RF1 | RF2 | RS3 | RS4 | Comments |
|---|---|---|---|---|---|---|---|---|
| D1 | 549 | 1 | 549 | und | und | und | und |   |
| D2 | 1252 | 6908 | 8159 | syl | syl | syl | syl |   |
| D3 | 1730 | 19920 | 21649 | syl | syl | syl | syl |   |
| D4 | 11357 | 25385 | 36741 | syl | syl | syl | syl |   |
| D5 | 2341 | 51278 | 53618 | syl | syl | syl | syl |   |
| D6 | 198 | 53766 | 53963 | und syl | und syl | und syl | und syl | Both N. sylvestris and N. undulata-derived sequence present in RF1, RF2, RS3 and RS4. |
| D7 | 427 | 54754 | 55180 | syl | syl | syl | syl |   |
| D8 | 8520 | 55476 | 63995 | syl | syl | syl | syl | 7034 bp in Repeat 1 |
| D9a | 3899 | 70301 | 74199 | syl | syl | syl | syl | In Repeat 1 |
| D10a | 15 | 75119 | 75133 | syl | syl | syl | syl | In Repeat 1 |
| D11a | 116 | 78132 | 78247 | syl | syl | syl | syl | In Repeat 2 |
| D12a | 2254 | 79183 | 81436 | syl | syl | syl | syl | In Repeat 2 and 3 |
| D13a | 1397 | 82296 | 83692 | syl | syl | syl | syl | In Repeat 3 |
| D14 | 2868 | 115382 | 118249 | syl | syl | syl | syl |   |
| D15 | 1669 | 118629 | 120297 | syl | syl | syl | syl |   |
| D16 | 2048 | 149970 | 152017 | syl | syl | syl | syl |   |
| D17 | 5055 | 159248 | 164303 | syl | syl | syl | syl |   |
| D18 | 14453 | 206392 | 220844 | syl | syl | syl | syl |   |
| D19 | 19770 | 238938 | 258707 | syl | syl | syl | syl |   |
| D20 | 303 | 260136 | 260438 | syl | syl | syl | syl |   |
| D11b | 116 | 279632 | 279747 | syl | syl | syl | syl | In Repeat 2 |
| D12b | 2254 | 280683 | 282936 | syl | syl | syl | syl | In Repeat 2 and 3 |

TABLE S8-continued

Deletions in *N. undulata* compared to *N. sylvestris*. Shown are 34 different deletions in *N. undulata* compared to *N. sylvestris*, and the origin of these regions in two recombinant fertile (RF1, RF2) and two CMS (RS3, RS4) offspring of GT19-C. 109,493 bp unique DNA sequence is missing from the *N. undulata* mtDNA compared to the *N. sylvestris* mtDNA. The deletions are associated with rearrangements in *N. undulata* compared to the *N. sylvestris* mtDNA structure apart from D20, D25 and D28. D6 coexists in RF1, RF2, RS3, and RS4 with a deletion-free *N. sylvestris*-derived homolog. D28 coexists in RS3 and RS4 with a minority deletion-free *N. sylvestris*-derived homolog. D29 and D30 exist in all four recombinants together with a minority deletion-free *N. sylvestris*-derived homolog. The location of deletions is given in the *N. sylvestris* mtDNA (KT997964).

| Deletion number | Deletion size (bp) | Deletion start | Deletion end | RF1 | RF2 | RS3 | RS4 | Comments |
|---|---|---|---|---|---|---|---|---|
| D13b | 1397 | 283796 | 285192 | syl | syl | syl | syl | In Repeat 3 |
| D21 | 1541 | 296186 | 297726 | syl | syl | syl | syl | |
| D22 | 593 | 303633 | 304225 | und | und | und | und | |
| D23 | 7290 | 317900 | 325189 | syl | syl | syl | syl | |
| D24 | 5046 | 344541 | 349586 | syl | syl | syl | syl | |
| D25 | 112 | 356533 | 356644 | und | und | und | und | |
| D26 | 6150 | 382358 | 388507 | syl | syl | syl | syl | |
| D27 | 27 | 389659 | 389685 | syl | syl | syl | syl | |
| D28 | 200 | 391829 | 392028 | syl | syl | und syl | und syl | Both *N. sylvestris* and *N. undulata*-derived sequence present in RS3 and RS4. |
| D29 | 145 | 393373 | 393517 | und syl | und syl | und syl | und syl | Both *N. sylvestris* and *N. undulata*-derived sequence present in RF1, RF2, RS3 and RS4. |
| D30 | 1465 | 393714 | 395178 | und syl | und syl | und syl | und syl | Both *N. sylvestris* and *N. undulata*-derived sequence present in RF1, RF2, RS3 and RS4. |
| D31 | 1889 | 397021 | 398909 | syl | syl | syl | syl | |
| D32 | 1348 | 402194 | 403541 | und | und | und | und | |
| D33 | 10504 | 404242 | 414745 | syl | syl | syl | syl | 7034 bp in Repeat 1 |
| D9b | 3899 | 421051 | 424949 | syl | syl | syl | syl | In Repeat 1 |
| D10b | 15 | 425869 | 425883 | syl | syl | syl | syl | In Repeat 1 |
| D11c | 116 | 428882 | 428997 | syl | syl | syl | syl | In Repeat 2 |
| D34 | 665 | 429933 | 430597 | syl | syl | syl | syl | In Repeat 2, part of D12 |

TABLE S9

Primers and restriction enzymes used to determine the genotype of 24 polymorphic loci in the GT19 mtDNA shown on FIG. 3. The genotype was determined by Sanger sequencing PCR products or running PCR products on an agarose gel with or without restriction enzyme digestion. Bold underlined nucleotides in primer sequences indicate a mismatch to the genomic DNA, introduced to change a restriction site for dCAPS analysis.

| Marker | Primer name | Primer start in *N. sylvestris* mtDNA (KT997964) | From top to bottom, the provided sequences are SEQ ID NOs: 214-261. Primer sequence | Fragment length in *N. sylvestris* (nt) | Fragment length in *N. undulata* (nt) | Restriction enzyme/ Sequencing/ Length polymorphism | Digested fragment sizes in *N. sylvestris* (nt) | Digested fragment sizes in *N. undulata* (nt) | GT19 genotype | Other amplification sites in repeats |
|---|---|---|---|---|---|---|---|---|---|---|
| Mit o1 | 0muF | 670 | AGAAGCTGTGATCGAG GAAGCCCC | 1294 | 1295 | Sequencing | — | — | undulata | |
| | 1muR | 1963 | GCTCTGAAGGGAGAGT TGAGCGGA | | | | | | | |
| Mit o2 | M3320F | 3320 | TTGAGCGTTT-GAAGTG GACGAAC | 406 | 406 | Hpy188I | 216, 121, 69 | 337, 69 | undulata | |
| | 3725R | 3725 | AGATCGGGCTGTCTGT ACCTTTG | | | | | | | |
| Mit o3 | 12051F | 12051 | CCGCTAATGAGATAAC TTCAATTTCGAC | 128 | 115 | HinfI | 74, 54 | 115 | undulata | |
| | 12178R | 12178 | TGGATTTCTCTACAAG TTGATCGCTG | | | | | | | |
| Mit o4 | 45502F | 45502 | GTTCCAAGTGACTAGC TTGGCTG | 268 | 268 | HaeIII | 108, 91, 69 | 177, 91 | sylvestris | |
| | 45769R | 45739 | AGCTAGAAAAAGGAAA GCGGCAC | | | | | | | |

TABLE S9-continued

Primers and restriction enzymes used to determine the genotype of 24 polymorphic loci in the GT19 mtDNA shown on FIG. 3. The genotype was determined by Sanger sequencing PCR products or running PCR products on an agarose gel with or without restriction enzyme digestion. Bold underlined nucleotides in primer sequences indicate a mismatch to the genomic DNA, introduced to change a restriction site for dCAPS analysis.

| Marker | Primer name | Primer start in *N. sylvestris* mtDNA (KT997964) | From top to bottom, the provided sequences are SEQ ID NOs: 214-261. Primer sequence | Fragment length in *N. sylvestris* (nt) | Fragment length in *N. undulata* (nt) | Restriction enzyme/ Sequencing/ Length polymorphism | Digested fragment sizes in *N. sylvestris* (nt) | Digested fragment sizes in *N. undulata* (nt) | GT19 genotype | Other amplification sites in repeats |
|---|---|---|---|---|---|---|---|---|---|---|
| Mito5 | 64757F | 64757 | TGAAACCCTTGCTTGTTTATCCCGCC | 172 | 172 | StyI | 148, 24 | 172 | sylvestris | Repeat 1, also amplifies 415507-415678 |
|  | 64928R | 64928 | TAGATTTAGCCAATTCCGGTGCG |  |  |  |  |  |  |  |
| Mito6 | 77508F | 77508 | GGGCGAAGGATATTCATGATATCC | 197 | 197 | HpaII | 197 | 175, 22 | sylvestris | Repeat 2, also amplifies 279008-279204, 428258-428454 |
|  | 77704R | 77704 | AGGTCCGCTACCAAAGAATTAGG |  |  |  |  |  |  |  |
| Mito7 | 100muF | 100029 | GCTTCGATGATCAACCCCTGGCAC | 1440 | 1440 | Sequencing | — | — | undulata |  |
|  | 101muR | 101468 | CCAAATACAAGGGAGCGGGCACTG |  |  |  |  |  |  |  |
| Mito8 | 131muF | 131632 | ATCAGAAGCATCCAGCAGCACCAC | 1301 | 1302 | Sequencing | — | — | sylvestris |  |
|  | 132muR | 132932 | GCTCTGCTGCATGACGGAGTGATC |  |  |  |  |  |  |  |
| Mito9 | 137804F | 137804 | GGTACCGGTTATGAGCCACATTC | 332 | 333 | SacI | 161, 117, 32, 22 | 171, 161 | undulata |  |
|  | 138135R | 138135 | GTCAAGTCAATAGCAGCCAGAGC |  |  |  |  |  |  |  |
| Mito10 | 147392F | 147392 | GGGTAGCTACAAGCATAAACCGGATT | 150 | 150 | HinfI | 150 | 128, 22 | undulata |  |
|  | 147541R | 147541 | TTCGGACTGTCTTGTTTTCAGGC |  |  |  |  |  |  |  |
| Mito11 | 158637F | 158637 | AGTACGGAACGAGCCTTGTCTAC | 422 | 418 | HpaII | 305, 117 | 187, 114, 117 | sylvestris |  |
|  | 159058R | 159058 | CTCCATAAGCATCCAAAGCTGCC |  |  |  |  |  |  |  |
| Mito12 | 173767F | 173768 | TGTACTGTGCCGTATCAGACCAG | 323 | 323 | BamHI | 237, 86 | 323 | undulata |  |
|  | 174089R | 174090 | GGGTTTACAGGAGATCCCAGAGG |  |  |  |  |  |  |  |
| Mito13 | 183muF | 183263 | ACCCGACCAGGGATGGAGGTAAAC | 1261 | 1251 | Sequencing | — | — | undulata |  |
|  | 184muR | 184523 | AGGTGCCTCTACATGAGCTTCGGG |  |  |  |  |  |  |  |
| Mito14 | 201muF | 201780 | CGCCTGGAAGTCCGAGGACCTTTA | 1286 | 1276 | Sequencing | — | — | undulata |  |
|  | 203muR | 203065 | CTCCGAAAGCGTTTTCCTTCCCCC |  |  |  |  |  |  |  |
| Mito15 | 203112F | 203112 | TACGGTGCGTCTTATCTGAAGGG | 467 | 467 | ApoI | 285, 128, 23, 16, 15 | 413, 23, 16, 15 | sylvestris |  |
|  | 203578R | 203578 | CACAAGTTTTGAATTCGCCGCTG |  |  |  |  |  |  |  |

TABLE S9-continued

Primers and restriction enzymes used to determine the genotype of 24 polymorphic loci in the GT19 mtDNA shown on FIG. 3. The genotype was determined by Sanger sequencing PCR products or running PCR products on an agarose gel with or without restriction enzyme digestion. Bold underlined nucleotides in primer sequences indicate a mismatch to the genomic DNA, introduced to change a restriction site for dCAPS analysis.

| Marker | Primer name | Primer start in *N. sylvestris* mtDNA (KT997964) | From top to bottom, the provided sequences are SEQ ID NOs: 214-261. Primer sequence | Fragment length in *N. sylvestris* (nt) | Fragment length in *N. undulata* (nt) | Restriction enzyme/ Sequencing/ Length polymorphism | Digested fragment sizes in *N. sylvestris* (nt) | Digested fragment sizes in *N. undulata* (nt) | GT19 genotype | Other amplification sites in repeats |
|---|---|---|---|---|---|---|---|---|---|---|
| Mito 16 | 220921F | 220921 | CATGCAAATTGATTTG TCCCCGAGAT | 150 | 150 | BglII | 150 | 128, 22 | *sylvestris* | |
| | 221070R | 221070 | AAAGGGGAGAGAAGAC GATAGCC | | | | | | | |
| Mito 17 | 270426F | 270426 | ATGATAAACATTCCTG AGGGAAAGTGC | 207 | 207 | HhaI | 180, 27 | 207 | *sylvestris* | |
| | 270632R | 270632 | GCATGTTTGGGATACG TTTGGTG | | | | | | | |
| Mito 18 | 306muF | 306541 | TGTATCACCGAGACAC CCGAAGGG | 1367 | 1367 | Sequencing | — | — | *undulata* | |
| | 307muR | 307907 | CGGATCGAATCAGAGT TCACGCCG | | | | | | | |
| Mito 19 | 309713F | 309713 | ATCTGGAGGAAGCATC TGGTCAC | 465 | 465 | BamHI | 247, 218 | 465 | *undulata* | |
| | 310177R | 310177 | TCTGTTGAAGGAAGAA GCCCCTC | | | | | | | |
| Mito 20 | 327muF | 327868 | AGTTGCTCTTTGCCCA AAGCCCTC | 1250 | 1250 | Sequencing | — | — | *undulata* | |
| | 329muR | 329117 | TGTTAGGCATTGAACC CCACCCCA | | | | | | | |
| Mito 21 | 356336F | 356336 | GAAGGAGTTAGGAGGA TGGAGCG | 374 | 262 | Length polym. | — | — | *undulata* | |
| | 356709R | 356709 | GACTCTTTGGCCTTTA GACTCGC | | | | | | | |
| Mito 22 | 360muF | 360645 | GCCATTGGTTACTGGT TGAGCCAC | 1339 | 1339 | Sequencing | — | — | *undulata* | |
| | 361muR | 361983 | GATGTCGTGACCGCTT AGGCTTGG | | | | | | | |
| Mito 23 | 381748F | 381748 | ATAGTGCTGCTACCAG AGAAGGC | 153 | 153 | EcoRV | 153 | 118, 35 | *undulata* | |
| | 381900R | 381900 | TCTTGTCTTGAATTTT TATAGAACGGCTTGAT | | | | | | | |
| Mito 24 | 393203F | 393203 | CGCCACTCCTTGGACG AAATAAG | 386 | 241 | Length polym. | — | — | *undulata* | |
| | 393588R | 393588 | TTATAACGCATGATAG CCGGCCC | | | | | | | |

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for effecting intercellular transfer of mitochondria in dicotyledonous plants for the creation of cytoplasmic male sterile (CMS) plants, comprising:
   a) joining a root stock of a first fertile plant and a scion from a second mitochondrial CMS plant under conditions suitable for graft formation, said first and second plants comprising distinct plastid and nuclear genetic markers; and
   b) culturing a graft region from said joined root stock and scion for a suitable period for grafting to occur;
      i) fragmenting or slicing the graft region to produce a fragment or slice and
      ii) transferring said fragment or slice to a plant regeneration medium and selecting for plant cells expressing both the nuclear and plastid genetic markers from said first and second plants and regenerating a plant from said selected plant cells; or,
   c) regenerating a shoot from the graft region and regenerating a plant from said shoot wherein cells in said plant express both the nuclear and plastid genetic markers from said first and second plants and
   d) selecting for a plant comprising mitochondria gene transfer events following step b) or step c) by selecting for the presence of altered plant morphology and/or visually detectable plastid-specific markers in said regenerated plants, wherein said mitochondria gene transfer events confer a CMS phenotype to said first fertile plant, wherein said first and second plants are selected from *Nicotiana* plants and solanaceous plants and said plant obtained in step d) is selected from tomato, potato, eggplant, pepper and tobacco.

2. The method of claim 1, further comprising characterization of the size and type of DNA transferred in the mitochondria gene transfer events.

3. The method of claim 1, wherein said first plant is *Nicotiana sylvestris* or *Nicotiana tabacum*.

4. The method of claim 1, wherein said first fertile plant is a tomato plant and said second CMS plant is a tobacco plant.

5. The method of claim 1, wherein said *Nicotiana* plants are selected from the group consisting of *Nicotiana tabacum, Nicotiana sylvestris*, and *Nicotiana benthamiana*, and said solanaceus plants are selected from the group consisting of potato, tomato, pepper and eggplant.

* * * * *